(12) United States Patent
Dacosta

(10) Patent No.: US 11,676,276 B2
(45) Date of Patent: Jun. 13, 2023

(54) COLLECTION AND ANALYSIS OF DATA FOR DIAGNOSTIC PURPOSES

(71) Applicant: UNIVERSITY HEALTH NETWORK, Toronto (CA)

(72) Inventor: Ralph Dacosta, Etobicoke (CA)

(73) Assignee: UNIVERSITY HEALTH NETWORK, Toronto (CA)

(*) Notice: Subject to any disclaimer, the term of this patent is extended or adjusted under 35 U.S.C. 154(b) by 230 days.

(21) Appl. No.: 16/593,174

(22) Filed: Oct. 4, 2019

(65) Prior Publication Data

US 2020/0104998 A1  Apr. 2, 2020

Related U.S. Application Data

(63) Continuation of application No. 15/328,214, filed as application No. PCT/CA2015/000444 on Jul. 24, 2015, now Pat. No. 10,438,356.

(60) Provisional application No. 62/028,386, filed on Jul. 24, 2014.

(51) Int. Cl.
| | | |
|---|---|---|
| G06T 7/00 | (2017.01) | |
| A61B 5/00 | (2006.01) | |
| G01N 21/64 | (2006.01) | |

(52) U.S. Cl.
CPC .......... *G06T 7/0016* (2013.01); *A61B 5/0071* (2013.01); *A61B 5/0077* (2013.01); *A61B 5/445* (2013.01); *G01N 21/6486* (2013.01); *G06T 2207/10016* (2013.01); *G06T 2207/10024* (2013.01); *G06T 2207/10048* (2013.01); *G06T 2207/10064* (2013.01); *G06T 2207/30088* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 4,556,057 A | 12/1985 | Hiruma et al. | |
| 4,740,459 A | 4/1988 | Chen et al. | |
| 5,306,144 A | 4/1994 | Hibst et al. | |
| 5,421,337 A | 6/1995 | Richards-Kortum et al. | |
| 5,456,260 A | 10/1995 | Kollias et al. | |
| 5,482,041 A | 1/1996 | Wilk et al. | |

(Continued)

FOREIGN PATENT DOCUMENTS

| | | |
|---|---|---|
| CA | 2360229 C | 5/2007 |
| CA | 2231799 C | 7/2007 |

(Continued)

OTHER PUBLICATIONS

Decision of Rejection in CN Application No. 2015800518278, dated Jul. 20, 2020.

(Continued)

*Primary Examiner* — Nancy Bitar
(74) *Attorney, Agent, or Firm* — Jones Robb, PLLC

(57) ABSTRACT

Systems and methods for obtaining diagnostic data of a target are disclosed. The systems include an imaging device and a drape. The imaging device includes at least one excitation light source for fluorescent imaging, and an optical sensor configured to detect signals responsive to illumination of the target with the excitation light. The drape is configured to reduce ambient light surrounding the target during imaging.

60 Claims, 42 Drawing Sheets

(56) References Cited

U.S. PATENT DOCUMENTS

| | | |
|---|---|---|
| 5,507,287 A | 4/1996 | Palcic et al. |
| 5,522,868 A | 6/1996 | Buckley et al. |
| 5,533,508 A | 7/1996 | Doiron |
| 5,552,134 A | 9/1996 | Morgan et al. |
| 5,562,100 A | 10/1996 | Kittrell et al. |
| 5,566,673 A | 10/1996 | Shiono et al. |
| 5,569,911 A | 10/1996 | Tomlinson, Jr. et al. |
| 5,572,996 A | 11/1996 | Doiron et al. |
| 5,579,773 A | 12/1996 | Vo-Dinh et al. |
| 5,588,428 A | 12/1996 | Smith et al. |
| 5,590,660 A | 1/1997 | MacAulay et al. |
| 5,605,152 A | 2/1997 | Slate et al. |
| 5,612,540 A | 3/1997 | Richards-Kortum et al. |
| 5,623,932 A | 4/1997 | Ramanujam et al. |
| 5,626,134 A | 5/1997 | Zuckerman |
| 5,628,310 A | 5/1997 | Rao et al. |
| 5,647,368 A | 7/1997 | Zeng et al. |
| 5,687,730 A | 11/1997 | Doiron et al. |
| 5,697,373 A | 12/1997 | Richards-Kortum et al. |
| 5,701,902 A | 12/1997 | Vari et al. |
| 5,760,407 A | 6/1998 | Margosiak et al. |
| 5,769,792 A | 6/1998 | Palcic et al. |
| 5,770,454 A | 6/1998 | Essenpreis et al. |
| 5,779,631 A | 7/1998 | Chance |
| 5,813,987 A | 9/1998 | Modell et al. |
| 5,820,558 A | 10/1998 | Chance |
| 5,849,595 A | 12/1998 | Alfano et al. |
| 5,851,181 A | 12/1998 | Talmor |
| 5,865,754 A | 2/1999 | Sevick-Muraca et al. |
| 5,879,294 A | 3/1999 | Anderson et al. |
| 5,935,075 A | 8/1999 | Casscells et al. |
| 5,952,664 A | 9/1999 | Wake et al. |
| 5,981,958 A | 11/1999 | Li et al. |
| 5,986,271 A | 11/1999 | Lazarev et al. |
| 6,002,137 A | 12/1999 | Hayashi |
| 6,008,889 A | 12/1999 | Zeng et al. |
| 6,014,204 A | 1/2000 | Prahl et al. |
| 6,021,344 A | 2/2000 | Lui et al. |
| 6,026,319 A | 2/2000 | Hayashi |
| 6,036,941 A | 3/2000 | Bottiroli et al. |
| 6,055,451 A | 4/2000 | Bambot et al. |
| 6,058,324 A | 5/2000 | Chance |
| 6,061,591 A | 5/2000 | Freitag et al. |
| 6,064,897 A | 5/2000 | Lindberg et al. |
| 6,064,899 A | 5/2000 | Fein et al. |
| 6,069,689 A | 5/2000 | Zeng et al. |
| 6,078,833 A | 6/2000 | Hueber |
| 6,081,612 A | 6/2000 | Gutkowicz-Krusin et al. |
| 6,081,739 A | 6/2000 | Lemchen |
| 6,088,087 A | 7/2000 | Graves et al. |
| 6,088,606 A | 7/2000 | Ignotz et al. |
| 6,091,984 A | 7/2000 | Perelman et al. |
| 6,091,985 A | 7/2000 | Alfano et al. |
| 6,095,982 A | 8/2000 | Richards-Kortum et al. |
| 6,104,939 A | 8/2000 | Groner et al. |
| 6,104,945 A | 8/2000 | Modell et al. |
| 6,122,042 A | 9/2000 | Wunderman et al. |
| 6,122,536 A | 9/2000 | Sun et al. |
| 6,124,597 A | 9/2000 | Shehada et al. |
| 6,128,516 A | 10/2000 | Macfarlane et al. |
| 6,128,525 A | 10/2000 | Zeng et al. |
| 6,129,664 A | 10/2000 | Macfarlane et al. |
| 6,135,965 A | 10/2000 | Turner et al. |
| 6,142,629 A | 11/2000 | Adel et al. |
| 6,148,227 A | 11/2000 | Wagnieres et al. |
| 6,161,031 A | 12/2000 | Hochman et al. |
| 6,167,297 A | 12/2000 | Benaron |
| 6,192,261 B1 | 2/2001 | Gratton et al. |
| 6,205,354 B1 | 3/2001 | Gellermann et al. |
| 6,212,425 B1 | 4/2001 | Irion et al. |
| 6,219,566 B1 | 4/2001 | Weersink et al. |
| 6,223,071 B1 | 4/2001 | Lundahl et al. |
| 6,236,871 B1 | 5/2001 | Tsuchiya |
| 6,236,881 B1 | 5/2001 | Zahler et al. |
| 6,238,348 B1 | 5/2001 | Crowley et al. |
| 6,241,662 B1 | 6/2001 | Richards-Kortum et al. |
| 6,256,530 B1 | 7/2001 | Wolfe |
| 6,258,576 B1 | 7/2001 | Richards-Kortum et al. |
| 6,272,367 B1 | 8/2001 | Chance |
| 6,272,376 B1 | 8/2001 | Marcu et al. |
| 6,280,386 B1 | 8/2001 | Alfano et al. |
| 6,289,236 B1 | 9/2001 | Koenig et al. |
| 6,304,766 B1 | 10/2001 | Colvin, Jr. |
| 6,317,624 B1 | 11/2001 | Kollias et al. |
| 6,343,227 B1 | 1/2002 | Crowley |
| 6,364,829 B1 | 4/2002 | Fulghum |
| 6,373,568 B1 | 4/2002 | Miller et al. |
| 6,385,484 B2 | 5/2002 | Nordstrom et al. |
| 6,393,315 B1 | 5/2002 | Aprahamian et al. |
| 6,422,994 B1 | 7/2002 | Kaneko et al. |
| 6,427,082 B1 | 7/2002 | Nordstrom et al. |
| 6,436,127 B1 | 8/2002 | Anderson et al. |
| 6,442,416 B1 | 8/2002 | Schultz |
| 6,465,968 B1 | 10/2002 | Sendai |
| 6,473,637 B1 | 10/2002 | Hayashi |
| 6,487,428 B1 | 11/2002 | Culver et al. |
| 6,496,719 B2 | 12/2002 | Hayashi |
| 6,510,338 B1 | 1/2003 | Irion et al. |
| 6,522,911 B1 | 2/2003 | Toida et al. |
| 6,526,309 B1 | 2/2003 | Chance |
| 6,542,772 B1 | 4/2003 | Chance |
| 6,549,801 B1 | 4/2003 | Chen et al. |
| 6,563,105 B2 | 5/2003 | Seibel et al. |
| 6,571,119 B2 | 5/2003 | Hayashi |
| 6,573,513 B2 | 6/2003 | Hayashi |
| 6,574,502 B2 | 6/2003 | Hayashi |
| 6,577,394 B1 | 6/2003 | Zavislan |
| 6,577,884 B1 | 6/2003 | Boas |
| 6,580,941 B2 | 6/2003 | Webb |
| 6,582,363 B2 | 6/2003 | Adachi et al. |
| 6,584,342 B1 | 6/2003 | Trushin et al. |
| 6,590,651 B1 | 7/2003 | Bambot et al. |
| 6,597,932 B2 | 7/2003 | Tian et al. |
| 6,600,947 B2 | 7/2003 | Averback et al. |
| 6,603,126 B2 | 8/2003 | Yamada et al. |
| 6,603,552 B1 | 8/2003 | Cline et al. |
| 6,615,063 B1 | 9/2003 | Ntziachristos et al. |
| 6,622,032 B1 | 9/2003 | Robinson et al. |
| 6,631,286 B2 | 10/2003 | Pfeiffer et al. |
| 6,631,289 B2 | 10/2003 | Alfano et al. |
| 6,636,759 B2 | 10/2003 | Robinson |
| 6,639,668 B1 | 10/2003 | Trepagnier |
| 6,640,124 B2 | 10/2003 | Elsner et al. |
| 6,640,130 B1 | 10/2003 | Freeman et al. |
| 6,640,131 B1 | 10/2003 | Irion et al. |
| 6,652,836 B2 | 11/2003 | Luiken |
| 6,665,556 B1 | 12/2003 | Alfano et al. |
| 6,667,803 B1 | 12/2003 | Flessland et al. |
| 6,668,186 B1 | 12/2003 | Zavislan et al. |
| 6,678,398 B2 | 1/2004 | Wolters et al. |
| 6,690,466 B2 | 2/2004 | Miller et al. |
| 6,694,158 B2 | 2/2004 | Polak |
| 6,697,652 B2 | 2/2004 | Georgakoudi et al. |
| 6,697,657 B1 | 2/2004 | Shehada et al. |
| 6,697,666 B1 | 2/2004 | Richards-Kortum et al. |
| 6,701,168 B1 | 3/2004 | Wilson et al. |
| 6,709,446 B2 | 3/2004 | Lundahl et al. |
| 6,711,429 B1 | 3/2004 | Gilboa et al. |
| 6,721,582 B2 | 4/2004 | Trepagnier et al. |
| 6,730,113 B2 | 5/2004 | Eckhardt et al. |
| 6,738,659 B2 | 5/2004 | Hsu |
| 6,748,259 B1 | 6/2004 | Benaron et al. |
| 6,750,964 B2 | 6/2004 | Levenson et al. |
| 6,751,490 B2 | 6/2004 | Esenaliev et al. |
| 6,757,554 B2 | 6/2004 | Rubinstein et al. |
| 6,763,262 B2 | 7/2004 | Hohla et al. |
| 6,766,184 B2 | 7/2004 | Utzinger et al. |
| 6,768,918 B2 | 7/2004 | Zelenchuk |
| 6,778,846 B1 | 8/2004 | Martinez et al. |
| 6,800,057 B2 | 10/2004 | Tsujita et al. |
| 6,806,089 B1 | 10/2004 | Lakowicz et al. |
| 6,818,903 B2 | 11/2004 | Schomacker et al. |
| 6,821,289 B2 | 11/2004 | Bode et al. |
| 6,826,424 B1 | 11/2004 | Zeng et al. |

(56) References Cited

U.S. PATENT DOCUMENTS

| | | |
|---|---|---|
| 6,865,407 B2 | 3/2005 | Kimball et al. |
| 6,868,285 B2 | 3/2005 | Muller-Dethlefs |
| 6,870,620 B2 | 3/2005 | Faupel et al. |
| 6,873,716 B1 | 3/2005 | Bowker et al. |
| 6,912,412 B2 | 6/2005 | Georgakoudi et al. |
| 6,914,250 B2 | 7/2005 | Seville |
| 6,922,523 B2 | 7/2005 | Merola et al. |
| 6,922,576 B2 | 7/2005 | Raskas |
| 6,930,773 B2 | 8/2005 | Cronin et al. |
| 6,933,154 B2 | 8/2005 | Schomacker et al. |
| 6,936,004 B2 | 8/2005 | Utsui |
| 6,970,729 B2 | 11/2005 | Hartmann |
| 6,975,898 B2 | 12/2005 | Seibel |
| 6,975,899 B2 | 12/2005 | Faupel et al. |
| 6,984,228 B2 | 1/2006 | Anderson et al. |
| 6,992,762 B2 | 1/2006 | Long |
| 7,006,223 B2 | 2/2006 | Mullani |
| 7,016,714 B2 | 3/2006 | Colvin, Jr. |
| 7,016,717 B2 | 3/2006 | Demos et al. |
| 7,027,153 B2 | 4/2006 | Mullani |
| 7,062,311 B1 | 6/2006 | Sendai et al. |
| 7,102,142 B2 | 9/2006 | Sendai |
| 7,103,401 B2 | 9/2006 | Schomacker et al. |
| 7,107,116 B2 | 9/2006 | Geng |
| 7,113,814 B2 | 9/2006 | Ward et al. |
| 7,127,282 B2 | 10/2006 | Nordstrom et al. |
| 7,130,672 B2 | 10/2006 | Pewzner et al. |
| 7,139,598 B2 | 11/2006 | Hull et al. |
| 7,139,603 B2 | 11/2006 | Chance |
| 7,149,567 B2 | 12/2006 | Demos et al. |
| 7,151,270 B2 | 12/2006 | Birk et al. |
| 7,167,243 B2 | 1/2007 | Mullani |
| 7,167,244 B2 | 1/2007 | Mullani |
| 7,197,355 B2 | 3/2007 | Nelson |
| 7,202,947 B2 | 4/2007 | Liu et al. |
| 7,209,773 B2 | 4/2007 | Iuliano |
| 7,212,848 B1 | 5/2007 | Wake et al. |
| 7,218,822 B2 | 5/2007 | Treado et al. |
| 7,224,468 B2 | 5/2007 | Fouquet |
| RE39,672 E | 6/2007 | Shehada et al. |
| 7,236,815 B2 | 6/2007 | Richards-Kortum et al. |
| 7,242,997 B2 | 7/2007 | Geng |
| 7,248,182 B2 | 7/2007 | Dudda et al. |
| 7,257,437 B2 | 8/2007 | Demos et al. |
| 7,277,210 B2 | 10/2007 | Lipson |
| 7,282,723 B2 | 10/2007 | Schomacker et al. |
| 7,283,858 B2 | 10/2007 | Sendai |
| 7,286,224 B2 | 10/2007 | Curry et al. |
| 7,289,836 B2 | 10/2007 | Colvin, Jr. |
| 7,310,547 B2 | 12/2007 | Zelenchuk |
| 7,317,938 B2 | 1/2008 | Lorenz et al. |
| 7,321,791 B2 | 1/2008 | Levenson et al. |
| 7,324,608 B1 | 1/2008 | Chiodini et al. |
| 7,353,055 B2 | 4/2008 | Hogan |
| 7,359,748 B1 | 4/2008 | Drugge |
| 7,365,844 B2 | 4/2008 | Richards-Kortum et al. |
| 7,366,365 B2 | 4/2008 | Carver |
| 7,368,694 B2 | 5/2008 | Goulas et al. |
| 7,376,346 B2 | 5/2008 | Merola et al. |
| 7,376,451 B2 | 5/2008 | Mahony et al. |
| 7,378,056 B2 | 5/2008 | Black |
| 7,389,132 B2 | 6/2008 | Wang et al. |
| 7,403,812 B2 | 7/2008 | Rice et al. |
| 7,404,929 B2 | 7/2008 | Fulghum, Jr. |
| 7,454,046 B2 | 11/2008 | Chhibber et al. |
| 7,477,393 B2 | 1/2009 | Sendai |
| 7,477,767 B2 | 1/2009 | Chhibber et al. |
| 7,477,931 B2 | 1/2009 | Hoyt |
| 7,479,990 B2 | 1/2009 | Imaizumi et al. |
| 7,491,956 B2 | 2/2009 | Knoche et al. |
| 7,495,233 B2 | 2/2009 | Pfister et al. |
| 7,496,392 B2 | 2/2009 | Alarcon et al. |
| 7,499,161 B2 | 3/2009 | Richards-Kortum et al. |
| 7,505,809 B2 | 3/2009 | Strommer et al. |
| 7,508,524 B2 | 3/2009 | Mahadevan-Jansen et al. |
| 7,510,699 B2 | 3/2009 | Black et al. |
| 7,515,952 B2 | 4/2009 | Balas et al. |
| 7,519,411 B2 | 4/2009 | Long |
| 7,522,797 B2 | 4/2009 | Treado et al. |
| 7,526,329 B2 | 4/2009 | Hogan et al. |
| 7,536,213 B2 | 5/2009 | Lipson et al. |
| 7,539,530 B2 | 5/2009 | Caplan et al. |
| 7,555,332 B2 | 6/2009 | Rice et al. |
| 7,558,619 B2 | 7/2009 | Ferguson et al. |
| 7,564,550 B2 | 7/2009 | Yaroslavsky et al. |
| 7,570,359 B2 | 8/2009 | Fox |
| 7,570,984 B2 | 8/2009 | Katsuda et al. |
| 7,580,185 B2 | 8/2009 | Haisch et al. |
| 7,583,993 B2 | 9/2009 | Sendai |
| 7,587,236 B2 | 9/2009 | Demos et al. |
| 7,590,437 B2 | 9/2009 | Rubinstein et al. |
| 7,598,088 B2 | 10/2009 | Balas |
| 7,599,065 B2 | 10/2009 | Sendai |
| 7,599,731 B2 | 10/2009 | Rice et al. |
| 7,599,732 B2 | 10/2009 | Sevick-Muraca et al. |
| 7,603,031 B1 | 10/2009 | Viaud et al. |
| 7,609,814 B2 | 10/2009 | Baumgart |
| 7,610,082 B2 | 10/2009 | Chance |
| 7,613,504 B2 | 11/2009 | Rowe |
| 7,613,505 B2 | 11/2009 | Mazuir et al. |
| 7,633,621 B2 | 12/2009 | Thornton |
| 7,646,002 B2 | 1/2010 | Sendai |
| 7,652,763 B2 | 1/2010 | Matousek et al. |
| 7,653,424 B2 | 1/2010 | March |
| 7,672,702 B2 | 3/2010 | Hwang et al. |
| 7,697,966 B2 | 4/2010 | Monfre et al. |
| 7,697,975 B2 | 4/2010 | Zeng |
| 7,702,381 B2 | 4/2010 | Gaeta et al. |
| 7,722,537 B2 | 5/2010 | Sterling et al. |
| 7,729,732 B2 | 6/2010 | Ohashi |
| 7,729,749 B2 | 6/2010 | Roessler et al. |
| 7,734,325 B2 | 6/2010 | Vizard et al. |
| 7,738,032 B2 | 6/2010 | Kollias et al. |
| 7,749,217 B2 | 7/2010 | Podhajsky |
| 7,761,126 B2 | 7/2010 | Gardner et al. |
| 7,764,303 B2 | 7/2010 | Pote et al. |
| 7,785,277 B2 | 8/2010 | Babaev et al. |
| 7,787,928 B2 | 8/2010 | Frisch et al. |
| 7,794,925 B2 | 9/2010 | Cullen |
| 7,798,955 B2 | 9/2010 | Ishihara et al. |
| 7,804,991 B2 | 9/2010 | Abovitz et al. |
| 7,812,945 B2 | 10/2010 | Fortier et al. |
| 7,817,267 B2 | 10/2010 | Carver |
| 7,821,640 B2 | 10/2010 | Koenig et al. |
| 7,822,450 B2 | 10/2010 | Colvin, Jr. et al. |
| 7,826,878 B2 | 11/2010 | Alfano et al. |
| 7,843,572 B2 | 11/2010 | Tearney et al. |
| 7,860,554 B2 | 12/2010 | Leonardi et al. |
| 7,865,231 B2 | 1/2011 | Tearney et al. |
| 7,872,759 B2 | 1/2011 | Tearney et al. |
| 7,888,659 B2 | 2/2011 | Scholz et al. |
| 7,889,348 B2 | 2/2011 | Tearney et al. |
| 7,899,518 B2 | 3/2011 | Trepagnier et al. |
| 7,899,624 B2 | 3/2011 | Cualing et al. |
| 7,904,140 B2 | 3/2011 | Pilon et al. |
| 7,909,253 B2 | 3/2011 | Sherman |
| 7,912,534 B2 | 3/2011 | Grinvald et al. |
| 7,914,442 B1 | 3/2011 | Gazdzinski |
| 7,916,283 B2 | 3/2011 | Fukutani et al. |
| 7,925,333 B2 | 4/2011 | Weir et al. |
| 7,935,055 B2 | 5/2011 | Burckhardt |
| 7,945,077 B2 | 5/2011 | Demos |
| 7,960,707 B2 | 6/2011 | Hall et al. |
| 7,962,200 B2 | 6/2011 | Ntziachristos et al. |
| 7,966,060 B2 | 6/2011 | Smit et al. |
| 7,973,925 B2 | 7/2011 | Lipson et al. |
| 7,977,650 B2 | 7/2011 | Laidevant et al. |
| 7,979,107 B2 | 7/2011 | Lin et al. |
| 7,983,736 B2 | 7/2011 | Villard et al. |
| 7,983,740 B2 | 7/2011 | Culver et al. |
| 7,986,342 B2 | 7/2011 | Yogesan et al. |
| 7,986,987 B2 | 7/2011 | Bazin et al. |
| 7,996,068 B2 | 8/2011 | Telischak et al. |
| 8,000,775 B2 | 8/2011 | Pogue et al. |

(56) References Cited

U.S. PATENT DOCUMENTS

| | | |
|---|---|---|
| 8,005,527 B2 | 8/2011 | Zelenchuk |
| 8,026,942 B2 | 9/2011 | Payonk et al. |
| 8,031,924 B2 | 10/2011 | Can et al. |
| 8,039,816 B2 | 10/2011 | Morishita et al. |
| 8,041,162 B2 | 10/2011 | Wang et al. |
| 8,045,153 B2 | 10/2011 | Mimura et al. |
| 8,045,263 B2 | 10/2011 | Yaroslavsky et al. |
| 8,050,735 B2 | 11/2011 | Feke et al. |
| 8,055,035 B2 | 11/2011 | Okugawa et al. |
| 8,078,243 B2 | 12/2011 | Ediger et al. |
| 8,078,263 B2 | 12/2011 | Zeman et al. |
| 8,078,264 B2 | 12/2011 | Basilion |
| 8,078,265 B2 | 12/2011 | Mahmood et al. |
| 8,082,024 B2 | 12/2011 | Alfano et al. |
| 8,107,696 B2 | 1/2012 | Pote et al. |
| 8,108,022 B2 | 1/2012 | Balberg et al. |
| 8,118,206 B2 | 2/2012 | Zand et al. |
| 8,121,671 B2 | 2/2012 | Hull et al. |
| 8,125,623 B2 | 2/2012 | Munger et al. |
| 8,129,105 B2 | 3/2012 | Zuckerman |
| 8,131,332 B2 | 3/2012 | Maynard et al. |
| 8,131,349 B2 | 3/2012 | Okawa et al. |
| 8,135,449 B2 | 3/2012 | Wilson et al. |
| 8,139,211 B2 | 3/2012 | Yaroslavsky et al. |
| 8,140,147 B2 | 3/2012 | Maynard et al. |
| 8,145,295 B2 | 3/2012 | Boyden et al. |
| 8,149,418 B2 | 4/2012 | Tearney et al. |
| 8,157,807 B2 | 4/2012 | Ferren et al. |
| 8,158,919 B2 | 4/2012 | Maeda et al. |
| 8,160,680 B2 | 4/2012 | Boyden et al. |
| 8,180,421 B2 | 5/2012 | Phillips et al. |
| 8,180,436 B2 | 5/2012 | Boyden et al. |
| 8,185,180 B2 | 5/2012 | Diab et al. |
| 8,188,446 B2 | 5/2012 | Ohno |
| 8,189,201 B2 | 5/2012 | Haisch et al. |
| 8,189,887 B2 | 5/2012 | Kollias et al. |
| 8,190,231 B2 | 5/2012 | Miwa et al. |
| 8,190,242 B2 | 5/2012 | Demos et al. |
| 8,204,579 B2 | 6/2012 | Nielsen et al. |
| 8,213,005 B2 | 7/2012 | Masilamani et al. |
| 8,218,143 B2 | 7/2012 | Gupta |
| 8,224,427 B2 | 7/2012 | Kopriva |
| 8,227,766 B2 | 7/2012 | Chapman |
| 8,228,368 B2 | 7/2012 | Zhao et al. |
| 8,229,548 B2 | 7/2012 | Frangioni |
| 8,231,526 B2 | 7/2012 | Yabe et al. |
| 8,238,993 B2 | 8/2012 | Maynard et al. |
| 8,243,269 B2 | 8/2012 | Matousek et al. |
| 8,246,611 B2 | 8/2012 | Paithankar et al. |
| 8,255,040 B2 | 8/2012 | Goldman et al. |
| 8,260,010 B2 | 9/2012 | Chhibber et al. |
| 8,270,689 B2 | 9/2012 | Liang et al. |
| 8,279,275 B2 | 10/2012 | Gono et al. |
| 8,280,140 B2 | 10/2012 | Levenson et al. |
| 8,280,471 B2 | 10/2012 | Rainone et al. |
| 8,285,015 B2 | 10/2012 | Demos |
| 8,285,353 B2 | 10/2012 | Choi et al. |
| 8,289,522 B2 | 10/2012 | Tearney et al. |
| 8,294,081 B2 | 10/2012 | Rosenheimer et al. |
| 8,295,901 B2 | 10/2012 | Tobola et al. |
| 8,311,607 B2 | 11/2012 | Zelenchuk |
| 8,320,650 B2 | 11/2012 | Demos et al. |
| 8,326,404 B2 | 12/2012 | Zeng et al. |
| 8,326,406 B2 | 12/2012 | Ntziachristos et al. |
| 8,330,087 B2 | 12/2012 | Domenicali |
| 8,332,006 B2 | 12/2012 | Naganuma et al. |
| 8,335,550 B2 | 12/2012 | Segman |
| 8,346,329 B2 | 1/2013 | Xu et al. |
| 8,351,026 B2 | 1/2013 | Stern |
| 8,351,041 B2 | 1/2013 | Leveque et al. |
| 8,358,821 B2 | 1/2013 | Yamaguchi et al. |
| 8,380,268 B2 | 2/2013 | Georgakoudi et al. |
| 8,385,615 B2 | 2/2013 | Levenson et al. |
| 8,391,961 B2 | 3/2013 | Levenson et al. |
| 8,403,862 B2 | 3/2013 | Grinvald et al. |
| 8,417,324 B2 | 4/2013 | Mycek et al. |
| 8,423,127 B2 | 4/2013 | Mahmood et al. |
| 8,452,357 B2 | 5/2013 | Rebec et al. |
| 8,452,384 B2 | 5/2013 | Ince |
| 8,463,006 B2 | 6/2013 | Prokoski |
| 8,467,857 B2 | 6/2013 | Kim et al. |
| 8,491,120 B2 | 7/2013 | Kahn et al. |
| 8,496,695 B2 | 7/2013 | Kang et al. |
| 8,498,682 B2 | 7/2013 | Markle et al. |
| 8,504,140 B2 | 8/2013 | Feke et al. |
| 8,521,261 B2 | 8/2013 | Okawa et al. |
| 8,538,195 B2 | 9/2013 | Robinson |
| 8,538,504 B2 | 9/2013 | Kleen et al. |
| 8,540,393 B2 * | 9/2013 | Mizuno ................ A61B 1/05 362/231 |
| 8,543,180 B2 | 9/2013 | Bechtel et al. |
| 8,547,425 B2 | 10/2013 | Ishihara |
| 8,562,657 B2 | 10/2013 | Ferren et al. |
| 8,574,859 B2 | 11/2013 | Lin et al. |
| 8,581,970 B2 | 11/2013 | Yamazaki et al. |
| 8,588,893 B2 | 11/2013 | Jaeb et al. |
| 8,593,513 B2 | 11/2013 | Yamaguchi et al. |
| 8,598,540 B2 | 12/2013 | Moy et al. |
| 8,605,974 B2 | 12/2013 | Liang et al. |
| 8,609,358 B2 | 12/2013 | Sebastian et al. |
| 8,617,057 B2 | 12/2013 | Morishita et al. |
| 8,619,257 B2 | 12/2013 | Plowman et al. |
| 8,620,411 B2 | 12/2013 | Stamatas et al. |
| 8,626,271 B2 | 1/2014 | Dunki-Jacobs et al. |
| 8,634,607 B2 | 1/2014 | Levenson et al. |
| 8,639,043 B2 | 1/2014 | Levenson et al. |
| 8,644,663 B2 | 2/2014 | Viellerobe et al. |
| 8,644,900 B2 | 2/2014 | Balberg |
| 8,644,911 B1 | 2/2014 | Panasyuk et al. |
| 8,660,637 B2 | 2/2014 | Crowley |
| 8,676,283 B2 | 3/2014 | Matter et al. |
| 8,676,302 B2 | 3/2014 | Wang et al. |
| 8,705,042 B2 | 4/2014 | Haisch et al. |
| 8,718,737 B2 | 5/2014 | Diab et al. |
| 9,042,967 B2 * | 5/2015 | Dacosta ............. A61B 5/0059 600/476 |
| 9,675,238 B2 * | 6/2017 | Iida ..................... A61B 1/0638 |
| 10,200,625 B2 | 2/2019 | Marcelpoil et al. |
| 10,438,356 B2 * | 10/2019 | Dacosta ............. A61B 5/0071 |
| 11,154,198 B2 | 10/2021 | Dacosta et al. |
| 2001/0034477 A1 | 10/2001 | Mansfield et al. |
| 2001/0047136 A1 | 11/2001 | Domanik et al. |
| 2002/0058864 A1 | 5/2002 | Mansfield et al. |
| 2002/0091324 A1 | 7/2002 | Kollias et al. |
| 2002/0138008 A1 | 9/2002 | Tsujita et al. |
| 2002/0146160 A1 | 10/2002 | Parker et al. |
| 2003/0001104 A1 | 1/2003 | Sendai et al. |
| 2003/0049175 A1 | 3/2003 | Buechler et al. |
| 2003/0055341 A1 | 3/2003 | Banerjee |
| 2003/0068274 A1 | 4/2003 | Jungmann et al. |
| 2003/0082105 A1 | 5/2003 | Fischman et al. |
| 2003/0109787 A1 | 6/2003 | Black |
| 2003/0113934 A1 | 6/2003 | Kwon |
| 2003/0123056 A1 | 7/2003 | Barnes et al. |
| 2003/0135122 A1 | 7/2003 | Bambot et al. |
| 2003/0158470 A1 * | 8/2003 | Wolters ............... A61B 5/0084 600/317 |
| 2003/0195401 A1 | 10/2003 | Tian et al. |
| 2003/0206301 A1 | 11/2003 | Cline et al. |
| 2003/0216626 A1 | 11/2003 | Tsujita et al. |
| 2004/0006276 A1 | 1/2004 | Demos et al. |
| 2004/0034292 A1 | 2/2004 | Mansfield et al. |
| 2004/0064053 A1 | 4/2004 | Chang et al. |
| 2004/0073120 A1 | 4/2004 | Motz et al. |
| 2004/0077951 A1 | 4/2004 | Lin et al. |
| 2004/0143190 A1 | 7/2004 | Schnitzer |
| 2004/0147843 A1 | 7/2004 | Bambot et al. |
| 2004/0148141 A1 | 7/2004 | Tsujita et al. |
| 2004/0186382 A1 | 9/2004 | Modell et al. |
| 2004/0186383 A1 | 9/2004 | Rava et al. |
| 2004/0196463 A1 | 10/2004 | Cline et al. |
| 2004/0225222 A1 | 11/2004 | Zeng et al. |
| 2004/0236229 A1 | 11/2004 | Freeman et al. |
| 2004/0260365 A1 | 12/2004 | Groseth et al. |

(56) References Cited

U.S. PATENT DOCUMENTS

| | | |
|---|---|---|
| 2005/0021235 A1 | 1/2005 | Bar-Or et al. |
| 2005/0064602 A1 | 3/2005 | Kaufman et al. |
| 2005/0119548 A1 | 6/2005 | Lin et al. |
| 2005/0131304 A1 | 6/2005 | Stamatas et al. |
| 2005/0143662 A1 | 6/2005 | Marchitto et al. |
| 2006/0004292 A1 | 1/2006 | Beylin |
| 2006/0013454 A1 | 1/2006 | Flewelling et al. |
| 2006/0030761 A1 | 2/2006 | Raskas |
| 2006/0077581 A1 | 4/2006 | Schwiegerling et al. |
| 2006/0089556 A1 | 4/2006 | Bambot et al. |
| 2006/0135869 A1 | 6/2006 | Farina |
| 2006/0151709 A1 | 7/2006 | Hahl |
| 2006/0241495 A1 | 10/2006 | Kurtz |
| 2006/0241499 A1 | 10/2006 | Irion et al. |
| 2006/0249690 A1 | 11/2006 | Pfister et al. |
| 2006/0253261 A1 | 11/2006 | Maier et al. |
| 2006/0270919 A1 | 11/2006 | Brenner |
| 2007/0004972 A1 | 1/2007 | Cole et al. |
| 2007/0024946 A1 | 2/2007 | Panasyuk et al. |
| 2007/0038124 A1 | 2/2007 | Fulghum et al. |
| 2007/0038126 A1 | 2/2007 | Pyle et al. |
| 2007/0049809 A1 | 3/2007 | Bechtel et al. |
| 2007/0060804 A1 | 3/2007 | Thompson et al. |
| 2007/0073156 A1 | 3/2007 | Zilberman et al. |
| 2007/0073158 A1 | 3/2007 | Sendai |
| 2007/0080305 A1 | 4/2007 | Maitrejean et al. |
| 2007/0093700 A1 | 4/2007 | Wang et al. |
| 2007/0093703 A1 | 4/2007 | Sievert et al. |
| 2007/0129613 A1 | 6/2007 | Rochester et al. |
| 2007/0129615 A1 | 6/2007 | Backman et al. |
| 2007/0135873 A1 | 6/2007 | Johansson et al. |
| 2007/0149868 A1 | 6/2007 | Blank et al. |
| 2007/0149882 A1 | 6/2007 | Wedel |
| 2007/0156036 A1 | 7/2007 | Pilon et al. |
| 2007/0167836 A1 | 7/2007 | Scepanovic et al. |
| 2007/0167838 A1 | 7/2007 | Hubble et al. |
| 2007/0179366 A1 | 8/2007 | Pewzner et al. |
| 2007/0212038 A1 | 9/2007 | Asai et al. |
| 2007/0213618 A1 | 9/2007 | Li et al. |
| 2007/0223797 A1 | 9/2007 | Kaneko |
| 2007/0239031 A1 | 10/2007 | Lee et al. |
| 2007/0239034 A1 | 10/2007 | Knoche et al. |
| 2007/0244395 A1 | 10/2007 | Wang et al. |
| 2007/0276199 A1 | 11/2007 | Ediger et al. |
| 2008/0013166 A1 | 1/2008 | Haisch et al. |
| 2008/0013960 A1 | 1/2008 | Tearney et al. |
| 2008/0045799 A1 | 2/2008 | Whitehead et al. |
| 2008/0051664 A1 | 2/2008 | Demos et al. |
| 2008/0051665 A1 | 2/2008 | Xu et al. |
| 2008/0058587 A1 | 3/2008 | Boyden et al. |
| 2008/0058785 A1 | 3/2008 | Boyden et al. |
| 2008/0058795 A1 | 3/2008 | Boyden et al. |
| 2008/0076985 A1 | 3/2008 | Matousek et al. |
| 2008/0082000 A1 | 4/2008 | Thoms |
| 2008/0086038 A1 | 4/2008 | Thornton |
| 2008/0091110 A1 | 4/2008 | Zelenchuk |
| 2008/0097225 A1 | 4/2008 | Tearney et al. |
| 2008/0103355 A1* | 5/2008 | Boyden ............... A61B 5/0084 600/103 |
| 2008/0103375 A1 | 5/2008 | Kiani |
| 2008/0103384 A1 | 5/2008 | Pfister |
| 2008/0119832 A1 | 5/2008 | Cronin |
| 2008/0132793 A1 | 6/2008 | Kollias et al. |
| 2008/0154102 A1 | 6/2008 | Frangioni et al. |
| 2008/0161699 A1 | 7/2008 | Zeng et al. |
| 2008/0177140 A1 | 7/2008 | Cline et al. |
| 2008/0183059 A1 | 7/2008 | LaPlante et al. |
| 2008/0188727 A1 | 8/2008 | Benaron et al. |
| 2008/0188736 A1 | 8/2008 | Bambot et al. |
| 2008/0194968 A1 | 8/2008 | Drugge |
| 2008/0221416 A1 | 9/2008 | Baker |
| 2008/0228049 A1 | 9/2008 | Black |
| 2008/0249381 A1 | 10/2008 | Muller et al. |
| 2008/0269617 A1 | 10/2008 | Kohler et al. |
| 2008/0300493 A1 | 12/2008 | Gatto et al. |
| 2008/0312540 A1 | 12/2008 | Ntziachristos |
| 2009/0018418 A1 | 1/2009 | Markle et al. |
| 2009/0043296 A1 | 2/2009 | Foster et al. |
| 2009/0060304 A1 | 3/2009 | Gulfo et al. |
| 2009/0073439 A1 | 3/2009 | Tearney et al. |
| 2009/0075391 A1 | 3/2009 | Fulghum, Jr. |
| 2009/0118600 A1 | 3/2009 | Ortiz et al. |
| 2009/0118622 A1 | 5/2009 | Durkin et al. |
| 2009/0124854 A1 | 5/2009 | Yamaguchi et al. |
| 2009/0131800 A1 | 5/2009 | Liang |
| 2009/0137908 A1 | 5/2009 | Patwardhan |
| 2009/0137952 A1 | 5/2009 | Ramamurthy et al. |
| 2009/0163819 A1 | 6/2009 | De Kok et al. |
| 2009/0187108 A1 | 7/2009 | Tang et al. |
| 2009/0192349 A1 | 7/2009 | Berguer et al. |
| 2009/0209866 A1 | 8/2009 | Abovitz et al. |
| 2009/0234234 A1 | 9/2009 | Machida |
| 2009/0236541 A1 | 9/2009 | Lomnes et al. |
| 2009/0247881 A1 | 10/2009 | Maeda et al. |
| 2009/0249500 A1 | 10/2009 | Zhao et al. |
| 2009/0264772 A1 | 10/2009 | Van Der Brug et al. |
| 2009/0268011 A1 | 10/2009 | Scott et al. |
| 2009/0270702 A1 | 10/2009 | Zeng et al. |
| 2009/0289200 A1 | 11/2009 | Ishii |
| 2009/0299196 A1 | 12/2009 | Bawendi et al. |
| 2010/0010340 A1 | 1/2010 | Godavarty et al. |
| 2010/0016688 A1 | 1/2010 | Debreczeny et al. |
| 2010/0041998 A1 | 2/2010 | Postel |
| 2010/0069758 A1 | 3/2010 | Barnes et al. |
| 2010/0140461 A1 | 6/2010 | Sprigle et al. |
| 2010/0160752 A1 | 6/2010 | Chance |
| 2010/0168586 A1 | 7/2010 | Hillman et al. |
| 2010/0174160 A1 | 7/2010 | Chance |
| 2010/0185099 A1 | 7/2010 | Johansson et al. |
| 2010/0217129 A1 | 8/2010 | El-Deiry et al. |
| 2010/0234739 A1 | 9/2010 | Nakaoka et al. |
| 2010/0234740 A1 | 9/2010 | Roessler et al. |
| 2010/0241055 A1 | 9/2010 | Dacey, Jr. et al. |
| 2010/0256469 A1 | 10/2010 | Cook et al. |
| 2010/0256504 A1 | 10/2010 | Moreau-Gaudry et al. |
| 2010/0268091 A1 | 10/2010 | Takaoka |
| 2010/0331705 A1 | 12/2010 | Het Hooft et al. |
| 2010/0331706 A1 | 12/2010 | Hasegawa |
| 2010/0331707 A1 | 12/2010 | Fukutani et al. |
| 2011/0015591 A1 | 1/2011 | Hanson et al. |
| 2011/0042580 A1 | 2/2011 | Wilson et al. |
| 2011/0063427 A1 | 3/2011 | Fengler et al. |
| 2011/0085714 A1* | 4/2011 | Yan .................... G06T 7/174 382/128 |
| 2011/0087111 A1 | 4/2011 | Ntziachristos |
| 2011/0098575 A1 | 4/2011 | Stamnes et al. |
| 2011/0102566 A1 | 5/2011 | Zakian et al. |
| 2011/0117025 A1 | 5/2011 | Dacosta et al. |
| 2011/0124989 A1 | 5/2011 | Edgar et al. |
| 2011/0144504 A1 | 6/2011 | Tearney et al. |
| 2011/0184260 A1 | 7/2011 | Robinson et al. |
| 2011/0201940 A1 | 8/2011 | Wang et al. |
| 2011/0213252 A1 | 9/2011 | Fulghum |
| 2011/0224553 A1 | 9/2011 | Stothers et al. |
| 2011/0237909 A1 | 9/2011 | Black |
| 2011/0275899 A1 | 11/2011 | Tearney et al. |
| 2011/0275900 A1 | 11/2011 | Gilhuly et al. |
| 2011/0295125 A1 | 12/2011 | Lin et al. |
| 2011/0313296 A9 | 12/2011 | Johnson et al. |
| 2012/0004508 A1 | 1/2012 | McDowall et al. |
| 2012/0004557 A1 | 1/2012 | McDowall et al. |
| 2012/0016230 A1 | 1/2012 | Kishima et al. |
| 2012/0029348 A1 | 2/2012 | Yaroslavsky et al. |
| 2012/0053429 A1 | 3/2012 | Trepagnier et al. |
| 2012/0059254 A1 | 3/2012 | Lifan et al. |
| 2012/0065484 A1 | 3/2012 | Hull et al. |
| 2012/0071764 A1 | 3/2012 | Yaroslavsky et al. |
| 2012/0078075 A1 | 3/2012 | Maynard et al. |
| 2012/0089031 A1 | 4/2012 | Ince |
| 2012/0108982 A1 | 5/2012 | Hoyt et al. |
| 2012/0197096 A1 | 8/2012 | Ridder et al. |
| 2012/0197134 A1 | 8/2012 | Okawa et al. |
| 2012/0220880 A1 | 8/2012 | Zuluaga |
| 2012/0226167 A1 | 9/2012 | Zuluaga |

(56) References Cited

U.S. PATENT DOCUMENTS

| | | |
|---|---|---|
| 2012/0265078 A1 | 10/2012 | Goldman et al. |
| 2012/0277558 A1 | 11/2012 | Barber et al. |
| 2012/0283531 A1 | 11/2012 | Maynard et al. |
| 2012/0302892 A1 | 11/2012 | Lue et al. |
| 2013/0018236 A1 | 1/2013 | Altshuler et al. |
| 2013/0033589 A1 | 2/2013 | Demos |
| 2013/0066215 A1 | 3/2013 | Tearney et al. |
| 2013/0072769 A1 | 3/2013 | Zuckerman |
| 2013/0100455 A1 | 4/2013 | Tearney et al. |
| 2013/0131488 A1 | 5/2013 | Zeng et al. |
| 2013/0148106 A1 | 6/2013 | Tearney et al. |
| 2013/0217985 A1 | 8/2013 | Dvorsky et al. |
| 2013/0237860 A1 | 9/2013 | Ince |
| 2013/0302746 A1 | 11/2013 | Liang et al. |
| 2014/0031647 A1 | 1/2014 | Lin et al. |
| 2014/0050667 A1 | 2/2014 | Wang et al. |
| 2014/0055605 A1 | 2/2014 | Moy et al. |
| 2014/0058220 A1 | 2/2014 | LeBoeuf et al. |
| 2014/0073885 A1 | 3/2014 | Frangioni |
| 2014/0128730 A1 | 5/2014 | Wang et al. |
| 2014/0207003 A1* | 7/2014 | Gilhuly ............ A61B 5/0088 600/476 |
| 2015/0182196 A1* | 7/2015 | Ninomiya ............ A61B 8/462 600/437 |
| 2017/0236281 A1 | 8/2017 | Dacosta |
| 2018/0242848 A1 | 8/2018 | Dacosta et al. |
| 2018/0325377 A1 | 11/2018 | Dacosta et al. |
| 2021/0259552 A1 | 8/2021 | Dacosta et al. |

FOREIGN PATENT DOCUMENTS

| | | |
|---|---|---|
| CA | 2306795 C | 1/2009 |
| CA | 2343401 C | 1/2009 |
| CA | 2305721 C | 2/2009 |
| CA | 2190374 C | 7/2010 |
| CA | 2371886 C | 1/2012 |
| CA | 2544204 C | 7/2013 |
| CA | 2331090 C | 10/2013 |
| CA | 2533621 C | 12/2013 |
| CA | 2489915 C | 1/2014 |
| CA | 2501098 C | 4/2014 |
| CA | 2685000 C | 4/2014 |
| CN | 1623001 A | 6/2005 |
| CN | 1652012 A | 8/2005 |
| CN | 101943661 A | 1/2011 |
| CN | 102099671 A | 6/2011 |
| EP | 694165 B1 | 3/1998 |
| EP | 930916 B1 | 9/2001 |
| EP | 864864 B1 | 1/2003 |
| EP | 850018 B1 | 4/2003 |
| EP | 779508 B1 | 6/2003 |
| EP | 1239771 B1 | 10/2004 |
| EP | 1089067 B1 | 12/2004 |
| EP | 783867 B1 | 2/2006 |
| EP | 1026999 B1 | 6/2006 |
| EP | 1161924 B1 | 12/2006 |
| EP | 1519769 B1 | 2/2007 |
| EP | 765134 B1 | 7/2007 |
| EP | 1071473 B1 | 10/2007 |
| EP | 1692510 B1 | 1/2008 |
| EP | 1144049 B1 | 3/2008 |
| EP | 1383542 B1 | 4/2008 |
| EP | 1912059 A1 | 4/2008 |
| EP | 1314395 B1 | 6/2008 |
| EP | 1520508 B1 | 11/2008 |
| EP | 1304955 B1 | 12/2008 |
| EP | 1281405 B1 | 1/2009 |
| EP | 1217943 B1 | 4/2009 |
| EP | 1196088 B1 | 9/2009 |
| EP | 1778076 B1 | 9/2009 |
| EP | 1277436 B1 | 12/2009 |
| EP | 1830705 B1 | 12/2010 |
| EP | 2073706 B1 | 10/2011 |
| EP | 1617761 B1 | 1/2012 |
| EP | 1045717 B1 | 3/2012 |
| EP | 2291640 A4 | 12/2012 |
| EP | 1576181 B1 | 8/2013 |
| EP | 3171765 A4 | 5/2018 |
| GB | 2367125 A | 3/2002 |
| JP | S59-40830 A | 3/1984 |
| JP | H04-127039 A | 4/1992 |
| JP | 05337142 A | 12/1993 |
| JP | H10-96697 A | 4/1998 |
| JP | 10328129 A | 12/1998 |
| JP | 2001503645 A | 3/2001 |
| JP | 2004127039 A | 4/2004 |
| JP | 2004-237081 A | 8/2004 |
| JP | 2005233636 A | 9/2005 |
| JP | 2005-331889 A | 12/2005 |
| JP | 2006-122335 A | 5/2006 |
| JP | 2006-515065 A | 5/2006 |
| JP | 2006-187598 A | 7/2006 |
| JP | 2007050010 A | 3/2007 |
| JP | 2007515947 A | 6/2007 |
| JP | 2007-524389 A | 8/2007 |
| JP | 2007198845 A | 8/2007 |
| JP | 2007-526478 A | 9/2007 |
| JP | 4475923 | 6/2010 |
| JP | 2011103118 A | 5/2011 |
| JP | 2011521237 A | 7/2011 |
| WO | 1994/021816 | 9/1994 |
| WO | 1997015226 | 5/1997 |
| WO | 2000/025114 A1 | 5/2000 |
| WO | 2002/055729 A1 | 7/2002 |
| WO | 02061405 | 8/2002 |
| WO | 2004025556 | 3/2004 |
| WO | 2006/007715 A1 | 1/2006 |
| WO | 2006101736 A1 | 9/2006 |
| WO | 2007/035829 A2 | 3/2007 |
| WO | 2008028298 A1 | 3/2008 |
| WO | 2009140757 | 11/2009 |
| WO | 2012-083349 A1 | 6/2012 |
| WO | 012075028 | 6/2012 |
| WO | 2016011534 A1 | 1/2016 |
| WO | 2017079844 | 5/2017 |

OTHER PUBLICATIONS

Song, et al., "Pork Freshness Detecting Method Based on the Change of Germ Area," Journal of Agricultural Mechanization Research, May 31, 2009.

Kang UK et al., "Fluorescence video dermatoscope," SOI—Korea Center of Korean Electrotechnology Research Institute (KERI), Seoul, Korean Republic, published in J. Opt. Technol. 75 (1), Jan. 2008.

Gupta et al., "Wood's lamp," Department of Dermatology, Venereology &Leprology, Dr. S. N. Medical College, Jodhpur,India, published in Indian J Dermatol Venereol Leprol, Mar.-Apr. 2004, vol. 70, Issue 2.

F. Fisher et al.,"An Affordable, Portable Fluorescence Imaging Device for Skin Lesion Detection Using a Dual Wavelength Approach for Image Contrast Enhancement and Aminolaevulinic Acid-induced Protoporphyrin IX. Part I. Design, Spectral and Spatial Characteristics," Department of Chemistry and Chemical Engineering, Royal Military College of Canada, published in Lasers Med Sci 2001 16:199-206.

Notice of Allowance in U.S. Appl. No. 16/027,775, dated Oct. 29, 2020.

Office Action in U.S. Appl. No. 14/719,493, dated Dec. 22, 2020.

Dietel et al., "5-Aminolaevulinic acid (ALA) induced formation of different fluorescent porphyrins: A study of the biosynthesis of porphyrins by bacteria of the human digestive tract", Journal of Photochemistry and Photobiology B: Biology 86:77-86, (2007) (10 pages).

Bissonette et al., "Current status of photodynamic therapy in dermatology." Dermatol Clin. Jul. 1997, 15(3):507-519 (Abstract 1 page).

Carruth, "Clinical applications of photodynamic therapy.", Int. J. Clin. Pract. Jan.-Feb. 1998; 52(1):39-42 (Abstract 1 page).

(56) References Cited

OTHER PUBLICATIONS

Dougherty et al. "Photodynamic Therapy", Journal of the National Cancer Institute, vol. 90, No. 12, Jun. 17, 1998:889-905 (17 pages).
Jori et al., "Photodynamic Therapy in the Treatment of Microbial Infections: Basic Principles and Perspective Applications", Lasers in Surgery and Medicine Jun. 2006, 38(5):468-481 (14 pages).
Hamblin et al., "Photodynamic therapy: a new antimicrobial approach to infectious disease?", Photochem Photobiol Sci. May 2004; 3(5):436-450 (30 pages).
Gudgin et al., "On the role of protoporphyrin IX photoproducts in photodynamic therapy," Journal of Photochemistry and Photobiology B: Biology 29; 1995:91-93 (3 pages).
Konig et al., "In vivo photoproduct formation during PDT with ALA-induced endogenous porphyrins," J Photochem. Photobiol. B: Biol., 18 (1993):287-290 (4 pages).
Georgakoudi et al., "The Mechanism of Photofrin Photobleaching and Its Consequences for Photodynamic Dosimetry," Photochemistry and Photobiology, 1997, 65(1):135-144 (10 pages).
Grossweiner, "Optical Dosimetry in Photodynamic Therapy," Lasers in Surgery and Medicine, 1986; 6:462-466 (5 pages).
Jongen et al., "Mathematical description of photobleaching in vivo describing the influence of tissue optics on measured fluorescence signals", Phys. Med. Biol. 42, 1997:1701-1716 (17 pages).
Rhodes et al., "Iontophoretic Delivery of ALA Provides a Quantitative Model for ALA Pharmacokinetics and PpIX Phototoxicity in Human Skin," The Society for Investigative Dermatology, Inc. 1997; 108:87-91 (6 pages).
Robinson et al., "Fluorescence Photobleaching of ALA-induced Protoporphyrin IX during Photodynamic Therapy of Normal Hairless Mouse Skin: The Effect of Light Dose and Irradiance and the Resulting Biological Effect," Photochemistry and Photobiology, 1998, 67(1):140-149 (10 pages).
Rotomskis et al., "Spectroscopic studies of photobleaching and photoproduct formation of porphyrins used in tumor therapy," Journal of Photochemistry and Photobiology B:Biology 33, 1996:61-67 (7 pages).
Grossweiner, "PDT light dosimetry revisited," Journal of Photochemistry and Photobiology B:Biology 38, 1997:258-268 (11 pages).
Tonnesen et al., "Angiogenesis in Wound Healing," The Society for Investigative Dermatology, Inc. 2000; 5(1):40-46 (7 pages).
Chwirot et al., "Detection of Melanomas by Digital Imaging of Spectrally Resolved Ultraviolet Light-induced Autofluorescence of Human Skin," European Journal of Cancer, vol. 34, No. 11:1730-1734, 1998 (5 pages).
Bishop, "Burn wound assessment and surgical management." Crit Care Nurs Clin North Am. 2004; 16(1):145-177 (Abstract 1 page).
Charles, "Radon exposure of the skin: II. Estimation of the attributable risk for skin cancer incidence," Journal of Radiological Protection 2007, 27(3):253-274 (23 pages).
Pretty, "Caries detection and diagnosis: Novel technologies," Journal of Dentistry 2006, 34(10):727-739 (13 pages).
Kois et al., "Detecting oral cancer: a new technique and case reports." Dent Today, Oct. 2006; 25(10):94 and 96-97 (Abstract 1 page).
Bogaards et al., "Increased Brain Tumor Resection Using Fluorescence Image Guidance in a Preclinical Model," Lasers in Surgery and Medicine 2004; 35:181-190 (10 pages).
Kingsley, "The Wound Infection Continuum and its Application to Clinical Practice," Ostomy Wound Management, Jul. 2003, 49(7A Suppl):1-7 (8 pages).
Sibbald et al., "Increased Bacterial Burden and Infection: The Story of Nerds and Stones," Advances In Skin & Wound Care, Oct. 2006; 19:447-461 (15 pages).
Bauer et al., "Angiogensis, Vasculogenesis, and Induction of Healing in Chronic Wounds," Vascular and Endovascular Surgery vol. 39, No. 4, 2005:293-306 (14 pages).
Brem et al., "Cellular and molecular basis of wound healing in diabetes," The Journal of Clinical Investigation, May 2007, vol. 117, No. 5:1219-1222 (4 pages).
Badiavas et al., "Treatment of Chronic Wounds With Bone Marrow-Derived Cells," Arch Dermatol, Apr. 2003, vol. 139 (4):510-516 (7 pages).
Phillips, "Biologic skin substitutes." J Dermatol Surg Oncol. Aug. 1993, 19(8):794-800 (Abstract 1 page).
European Communication dated Apr. 3, 2020 in connection with European Application No. 15824466.5, 9 pages.
Chinese Office Action, with English language translation, dated Mar. 3, 2020 in connection with Chinese Application No. 201580051827. 8, 15 pages.
Examination Report for IN Application No. 201717005984 dated Feb. 23, 2021.
Notice of Allowance in U.S. Appl. No. 16/027,775, dated Mar. 2, 2021.
U.S. Appl. No. 17/193,318, filed Mar. 5, 2021.
Treuillet, S. et al. "Three-Dimensional Assessment of Skin Wounds Using a Standard Digital Camera", IEEE Transactions on Medical Imaging, May 2009, vol. 28, No. 5, pp. 752-762.
Hanibuchi et al., "Autofluorescence bronchoscopy, a novel modality for the early detection of bronchial premalignant and malignant lesions", The Journal of Medical Investigation 2007, vol. 54:261-266 (6 pages).
Poh et al., "Direct Fluorescence Visualization of Clinically Occult High-Risk Oral Premalignant Disease Using a Simple Hand-Held Device", Head & Neck—DOI, Jan. 2007; 29(1):71-76 (6 pages).
DaCosta et al., "New optical technologies for earlier endoscopic diagnosis of premalignant gastrointestinal lesions", Journal of Gastroenterology and Hepatology (2002) 17 (Suppl.) S85-S104 (20 pages).
DaCosta et al., "Molecular Fluorescence Excitation-Emission Matrices Relevant to Tissue Spectroscopy", Photochemistry and Photobiology Oct. 2003, 78(4):384-392 (9 pages).
Kingsley et al., "A proactive approach to wound infection", Nursing Standard Apr. 2001; 15(30): 50-54, 56 & 58 (6 pages).
Falanga et al., "Workshop on the Pathogenesis of Chronic Wounds," J. Invest Dermatol 1994, 102(1):125-127 (4 pages).
Gardner et al., "Diagnostic Validity of Semiquantitative Swab Cultures," Wounds Feb. 2007; vol. 19, Issue 2:31-38 (8 pages).
Serena et al., "The Lack of Reliability of Clinical Examination in the Diagnosis of Wound Infection: Preliminary Communication," The International Journal of Lower Extremity Wounds, V7(1); Mar. 2008:32-35 (4 pages).
Perednia, "What dermatologists should know about digital imaging," J Am Acad Dermatol 1991, 25:89-108 (20 pages).
Winter, "Formation of the Scab and the Rate of Epithelization of Superficial Wounds in the Skin of the Young Domestic Pig," Nature, Jan. 20, 1962, 193:293-294 (2 pages).
Dow et al., "Infection in chronic wounds: controversies in diagnosis and treatment.", Ostomy/VVound Management 1999, 45:23-40 (Abstract—1 page).
Bowler et al., "Wound Microbiology and Associated Approaches to Wound Management," Clinical Microbiology Reviews 2001, 14:244-269 (27 pages).
Yasui et al., "Determination of collagen fiber orientation in human tissue by use of polariztation measurement of molecular second-harmonic-generation light", Applied Optics May 10, 2004; vol. 43, No. 14:2861-2867 (7 pages).
D'Hallewin et al., "Fluorescence Detection of Bladder Cancer: A Review", European Urology 2002, 42(5):417-425 (9 pages).
Falanga et al., "Wounding of Bioengineered Skin: Cellular and Molecular Aspects After Injury," J. Invest Dermatol 2002, 119(3):653-660 (8 pages).
Galpin et al., "Sepsis Associated with Decubitus Ulcers," The American Journal of Medicine, Sep. 1976, vol. 61 pp. 346-350 (5 pages).
Broer et al. "Laser-induced Fluorescence Spectroscopy for Real-Time Tissue Differentiation", Medical Laser Application 19:45-53, 2004 (9 pages).
DaCosta, et al., "Autofluorescence characterisation of isolated whole crypts and primary cultured human epithelial cells from normal, hyperplastic, and adenomatous colonic mucosa", J Clin Pathol 2005; 58:766-774 (10 pages).

(56) References Cited

OTHER PUBLICATIONS

Andersson-Engels, et al. "In vivo fluorescence imaging for tissue diagnostics", Phys. Med. Biol. 42 (1997):815-824 (10 pages).
Zhu, "Thesis: Non-invasive Optical Technologies to Monitor Wound Healing", Drexel University, Dec. 2007.
Jacques et al., "PDT with ALA/PPIX is enhanced by prolonged light exposure putatively by targeting mitochondria." SPIE Proceedings, vol. 2972, Optical Methods for Tumor Treatment and Detection, ed T. Dougherty, San Jose, Feb. 1997 (5 pages).
Website http://www.iec.ch/online news/etech/arch_2006/etech_0906/focus.htm.
International Search Report for PCT/CA2015/000444 dated Oct. 30, 2015.
Notice of Grounds of Rejection in corresponding JP Application No. 2017-503917, dated May 7, 2019.
First Office Action—Search Report in corresponding CN Application No. 2015800518278, dated Apr. 26, 2019.
Non-Final Office Action dated Apr. 3, 2018 in connection with U.S. Appl. No. 15/328,214, 11 pages.
Cutting et al., Journal of Wound Care, 1994, pp. 198-201.
Ayton M., "Wound Care: wounds that won't heal", Nurs Times, Nov. 1985; 81(46): suppl 16-19, 1 page.
Grocott P., "The palliative management of fungating malignant wounds", J Wound Care, May 1995; 4(5): 240-2, 1 page.
Collier M., The assessment of patients with malignant fungating woulds—holistic approach: Part 1, Nurs Times, Oct. 29-Nov. 4, 1997; 93(44): suppl 1-4, 1 page.
Grocott P., "The management of fungating wounds", J Wound Care, May 1999; 8(5):232-4, 1 page.
Young T., "The challenge of managing fungating wounds", Community Nurse, Oct. 1997; 3(9):41-4, 1 page.
Notice of Allowance dated Dec. 18, 2018 in connection with U.S. Appl. No. 15/328,214, 21 pages.
Notice of Allowance dated Mar. 27, 2019 in connection with U.S. Appl. No. 15/328,214, 88 pages.
Japanese Office Action dated Jan. 21, 2020 in connection with Japanese Application No. 2017-503917, 5 pages.
Notice of Allowance dated Jan. 30, 2019 in connection with U.S. Appl. No. 15/328,214, 6 pages.
Extended European Search Report in European Application No. 15 824 466.5, dated Apr. 19, 2018, 13 pages.
Office Action dated Jun. 29, 2022 in Canadian Patent Application No. 2,955,976.
Office Action dated Jul. 19, 2022 in Japanese Patent Application No. 2020-159809, 3 pages.
Decision Of Reexamination dated Aug. 24, 2022 in Chinese Patent Application No. 2015800518278, 26 pages.

*Adiuvo Diagnostics Private Limited* Vs. *University Health Network*, Evidence by way of an Affidavit on behalf of the opponent, 13 pages.
Hiram C. Polk, Jr "Early Detection of Pseudomonas Burn Infection", Clinical Experience with Wood's Light Fluorescence, Arch Surg/vol. 98, Mar. 1969, 3 pages.
S Veeranna, "Wood's lamp: A modified method of examination" Indian J Dermatol Venereol Leprol Sep.-Oct. 2005 vol. 71 Issue 5, 2 pages.
Ev Vogeley, MD, JD, "Experience With Wood Lamp Illumination and Digital Photography in the Documentation of Bruises on Human Skin", vol. 156, Mar. 2002, www.archpediatrics.com, 4 pages.
Final Additional Submission in reply to statement filed Jun. 15, 2022 related to pre-grant opposition. Indian Patent Application No. 9067/DELNP/2010, 417 pages.
Adiuvo Diagnostics private limited Pre-grant opposition filed Jan. 3, 2021 for Pre-grant Opposition Indian patent Application: 9067/DELNP/2010, 640 pages.
Final Office Action dated Jun. 14, 2021 in related U.S. Appl. No. 14/719,493, 28 pages.
Office Action dated Jun. 29, 2021 in related U.S. Appl. No. 15/965,462, 16 pages.
Office Action in CA Application No. 2,955,976 dated Aug. 11, 2021.
U.S. Appl. No. 17/407,870, filed Aug. 20, 2021.
U.S. Appl. No. 17/408,027, filed Aug. 20, 2021.
Cutting et al., Journal of Wound Care 1994, 3:198-201.
JP Office Action in JP Application No. 2020-159809 dated Sep. 28, 2021, 7 pages.
Office Action dated Oct. 5, 2021 in related U.S. Appl. No. 17/193,318, 24 pp.
Wieringa, F. P., Mastik, F., Cate, F. J., Neumann, H. A., & van der Steen, A. F. (2006). Remote non-invasive stereoscopic imaging of blood vessels: first in-vivo results of a new multispectral contrast enhancement technology. Annals of biomedical engineering, 34(12), 1870-1878. (Year: 2006).
U.S. Appl. No. 17/509,914, filed Oct. 25, 2021.
Notice of Allowance dated Nov. 12, 2021 for U.S. Appl. No. 15/965,462, 15 pp.
Notice of Allowance dated Nov. 26, 2021 for U.S. Appl. No. 14/719,493.
Office Action dated Jan. 27, 2022 for U.S. Appl. No. 17/193,318.
European Search report dated Jan. 13, 2022 for EP Patent Application No. 21187101.7.
Examination Report dated Mar. 10, 2022 in CN App No. 2015-800518278.
Final Office Action dated Jan. 31, 2023 in counterpart Japanese Application No. 2020-159809.

* cited by examiner

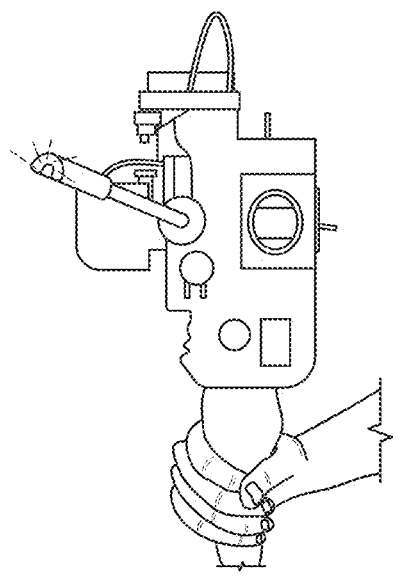 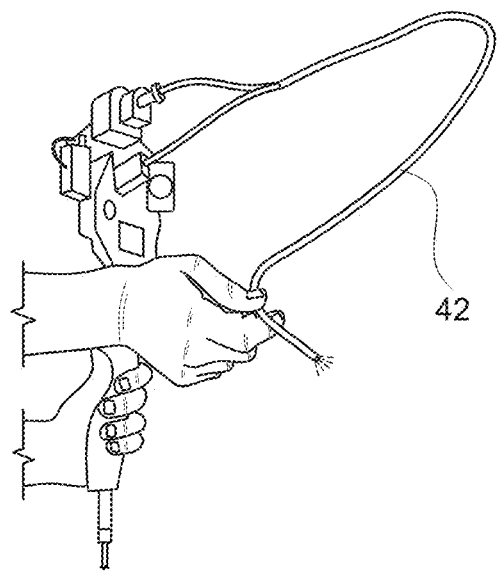
a                b
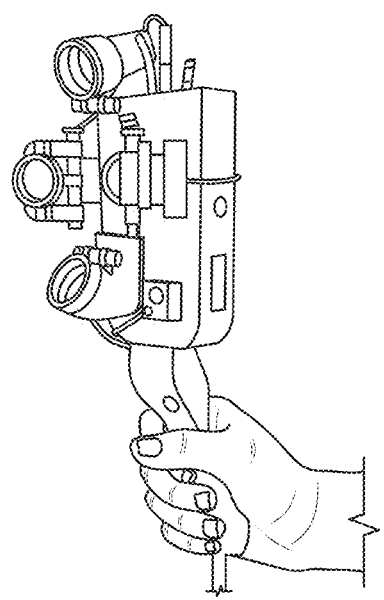 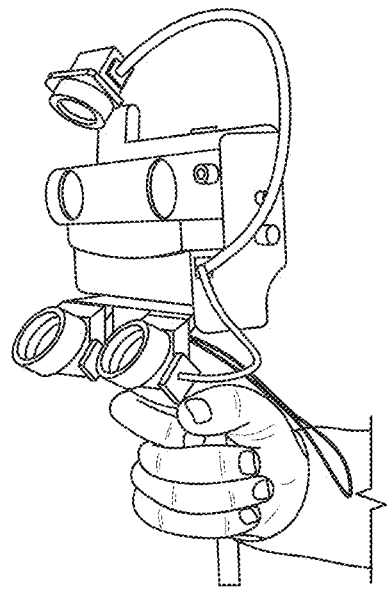
c                d
FIG. 5B

|  | Chronic wound in diabetic patient | Wound in diabetic mouse/rat |
|---|---|---|
| Macromolecular | | |
| Nerve count | ↓ | ↓ |
| Angiogenesis | ↓ | ↓ |
| Granulation tissue formation | ↓ | ↓ |
| Collagen content | ↓ | ↓ |
| Enzyme activity | | |
| NEP | ↑ | ↑ |
| NOS | ↑ | ↓ |
| Arginase | ↑ | ↑ (mouse, chronic) ↓ (rat) |
| MMPs | ↑ | ↑ |
| TIMP concentration | ↓ | ---- |
| Neutrophil elastase | ↑ | ---- |
| Cathepsin G | ↑ | ---- |
| Growth factors and receptors | | |
| IGF-1 | ↓ | ↓ |
| IGF-2 | ↑ | ↑ (mRNA) |
| IGF-RI (mRNA) | ---- | ↓ |
| TGF-β1 | ↓ | ↓ |
| TGF-β2 | ↑ | ---- |
| TGF-β3 | ↑ | ---- |
| TGF-βR1 and -R2 | ↓ | ---- |
| PDGF | ↓ | ↓ |
| PDGF-R | ---- | ↓ |
| KGF (mRNA) | ---- | ↓ |
| aFGF (mRNA) | ---- | ↓ |
| bFGF (mRNA) | ---- | ↓ |
| FGF-R1, -2, -3 (mRNA) | ---- | ↓ |
| IL-6 | ---- | ↓ |
| VEGF | ---- | ↓ |
| NGF | ---- | ↓ |
| MIP-2 | ---- | ↑ |
| MCP-1 | ---- | ↑ |
| TNFα (mRNA) | ---- | ↑ |
| IL-1β (mRNA) | ---- | ↑ |
| Other | | |
| GSH | ↓ | ↓ |

FIG. 34

COLLECTION AND ANALYSIS OF DATA FOR DIAGNOSTIC PURPOSES

This application is a continuation of U.S. application Ser. No. 15/328,214, filed Jan. 23, 2017, which is a U.S. national stage application under 35 U.S.C. § 371(c) of International Application No. PCT/CA2015/000444, filed on Jul. 24, 2015, which claims priority to U.S. Provisional Application No. 62/028,386, filed Jul. 24, 2014, the entire contents of each of which are incorporated by reference herein.

TECHNICAL FIELD

Devices and methods for collecting data for diagnostic purposes are disclosed. In particular, the devices and methods of the present application may be suitable for evaluating and tracking bacterial load in a wound over time.

BACKGROUND

Wound care is a major clinical challenge. Healing and chronic non-healing wounds are associated with a number of biological tissue changes including inflammation, proliferation, remodeling of connective tissues and, a common major concern, bacterial infection. A proportion of wound infections are not clinically apparent and contribute to the growing economic burden associated with wound care, especially in aging populations. Currently, the gold-standard wound assessment includes direct visual inspection of the wound site under white light combined with indiscriminate collection of bacterial swabs and tissue biopsies resulting in delayed, costly and often insensitive bacteriological results. This may affect the timing and effectiveness of treatment. Qualitative and subjective visual assessment only provides a gross view of the wound site, but does not provide information about underlying biological and molecular changes that are occurring at the tissue and cellular level. A relatively simple and complementary method that collects and analyzes 'biological and molecular' information in real-time to provide early identification of such occult change and guidance regarding treatment of the same is desirable in clinical wound management. Early recognition of high-risk wounds may guide therapeutic intervention and provide response monitoring over time, thus greatly reducing both morbidity and mortality due especially to chronic wounds.

SUMMARY

In accordance with one aspect of the present disclosure, a system for obtaining diagnostic data of a target comprises an imaging device and a drape. The imaging device includes at least one excitation light source configured to directly illuminate a portion of the target with excitation light and an optical sensor configured to detect signals responsive to illumination of the target with the excitation light. The drape is configured to reduce ambient light surrounding the target during imaging.

In accordance with another aspect of the present disclosure, a method of obtaining diagnostic data of a target comprises reducing ambient light in an environment surrounding the target, and while the target is within the reduced ambient light environment: directly illuminating the target with excitation light emitted by at least one excitation light source of a handheld imaging device, the at least one excitation light source emitting at least one wavelength or wavelength band configured to cause at least one biomarker in the target to fluoresce, and collecting bacterial autofluorescence data regarding the illuminated target with the handheld imaging device. The method further comprises analyzing the collected bacterial autofluorescence data with a processor of the handheld imaging device and using pixel intensity to determine bacterial load of the illuminated target.

In accordance with yet another aspect of the present disclosure, an adaptor for configuring a mobile device for fluorescent imaging of a target comprises a housing configured to be removably coupled to the mobile device, at least one excitation light source configured to emit excitation light to directly illuminate the target with the excitation light, an emissions filter configured to permit signals responsive to illumination of the target with the excitation light to pass through the filter, and a power source for the at least one excitation light source.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

The accompanying drawings, which are incorporated in and constitute a part of this specification, illustrate embodiments of the disclosure and together with the description, serve to explain the principles of the disclosure.

BRIEF DESCRIPTION OF DRAWINGS

At least some features and advantages will be apparent from the following detailed description of embodiments consistent therewith, which description should be considered with reference to the accompanying drawings, wherein:

FIGS. 5A and 5B show alternate exemplary embodiments of a handheld device for obtaining white light and fluorescent light data from a target in accordance with the present disclosure;

FIG. 34 is a table showing examples of tissue, cellular and molecular biomarkers known to be associated with wound healing;

Figure 1:
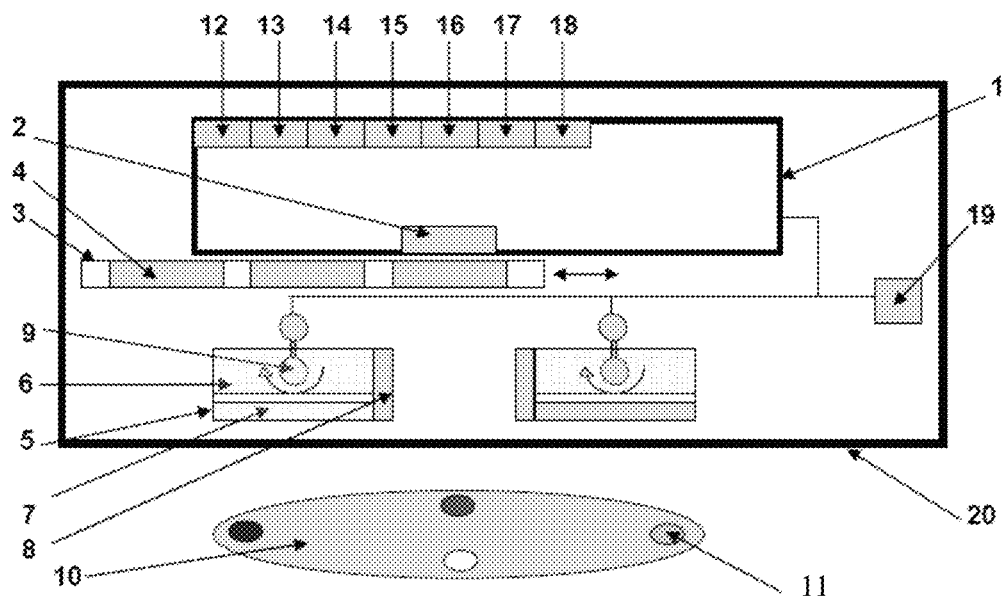
FIG. 1 is a schematic diagram of an exemplary device for fluorescence-based monitoring in accordance with the present disclosure.

Although the following detailed description makes reference to illustrative embodiments, many alternatives, modifications, and variations thereof will be apparent to those skilled in the art. Accordingly, it is intended that the claimed subject matter be viewed broadly.

DETAILED DESCRIPTION

Reference will now be made in detail to various embodiments, examples of which are illustrated in the accompanying drawings. The various exemplary embodiments are not intended to limit the disclosure. To the contrary, the disclosure is intended to cover alternatives, modifications, and equivalents.

Conventional clinical assessment methods of acute and chronic wounds continue to be suboptimal. Such assessment methods usually are based on a complete patient history, qualitative and subjective clinical assessment with simple visual appraisal using ambient white light and the 'naked eye,' and can sometimes involve the use of color photography to capture the general appearance of a wound under white light illumination. Regular re-assessment of progress toward healing and appropriate modification of the intervention is also necessary. Wound assessment terminology is non-uniform, many questions surrounding wound assessment remain unanswered, agreement has yet to be reached on the key wound parameters to measure in clinical practice, and the accuracy and reliability of available wound assessment techniques vary.

Visual assessment is frequently combined with swabbing and/or tissue biopsies for bacteriological culture for diagnosis. Bacterial swabs are collected at the time of wound examination and have the noted advantage of providing identification of specific bacterial/microbial species. However, multiple swabs and/or biopsies often are collected randomly from the wound site, and some swabbing techniques may in fact spread the microorganisms around with the wound during the collection process thus affecting patient healing time and morbidity. This may be a problem especially with large chronic (non-healing) wounds where the detection yield for bacterial presence using current swabbing and biopsy protocols is suboptimal (diagnostically insensitive), despite many swabs being collected.

Thus, current methods for obtaining swabs or tissue biopsies from the wound site for subsequent bacteriological culture are based on a non-targeted or 'blind' swabbing or punch biopsy approach, and have not been optimized to minimize trauma to the wound or to maximize the diagnostic yield of the bacteriology tests. In addition, bacteriological culture results often take about 2-3 days to come back from the laboratory and can be inconclusive, thus delaying accurate diagnosis and treatment. Thus, conventional methods of obtaining bacterial swabs do not necessarily provide relevant data regarding the wound and cannot provide real-time detection of infectious status of wounds. The lack of a non-invasive method to objectively and rapidly evaluate wound repair at a biological level (which may be at greater detail than simply appearance or morphology based), and to aid in targeting of the collection of swab and tissue biopsy samples for bacteriology is a major obstacle in clinical wound assessment and treatment. An alternative method is highly desirable.

As wounds (chronic and acute) heal, a number of key biological changes occur at the wound site at the tissue and cellular level. Wound healing involves a complex and dynamic interaction of biological processes divided into four overlapping phases—haemostasis, inflammation, cellular proliferation, and maturation or remodeling of connective tissues—which affect the pathophysiology of wound healing. A common major complication arising during the wound healing process, which can range from days to months, is infection caused by bacteria and other microorganisms. This can result in a serious impediment to the healing process and lead to significant complications. All wounds contain bacteria at levels ranging from contamination, through colonization, critical colonization to infection, and diagnosis of bacterial infection is based on clinical symptoms and signs (e.g., visual and odorous cues).

The most commonly used terms for wound infection have included wound contamination, wound colonisation, wound infection and, more recently, critical colonisation. Wound contamination refers to the presence of bacteria within a wound without any host reaction; wound colonisation refers to the presence of bacteria within the wound which do multiply or initiate a host reaction; and critical colonisation refers to multiplication of bacteria causing a delay in wound healing, usually associated with an exacerbation of pain not previously reported but still with no overt host reaction. Wound infection refers to the deposition and multiplication of bacteria in tissue with an associated host reaction. In practice the term 'critical colonisation' can be used to describe wounds that are considered to be moving from colonisation to local infection. The challenge within the clinical setting, however, is to ensure that this situation is quickly recognized with confidence and for the bacterial bioburden to be reduced as soon as possible, perhaps through the use of topical antimicrobials. Potential wound pathogens can be categorised into different groups, such as, bacteria, fungi, spores, protozoa and viruses depending on their structure and metabolic capabilities. Although viruses do not generally cause wound infections, bacteria can infect skin lesions formed during the course of certain viral diseases. Such infections can occur in several settings including in health-care settings (hospitals, clinics) and at home or chronic care facilities. The control of wound infections is increasingly complicated, yet treatment is not always guided by microbiological diagnosis. The diversity of micro-organisms and the high incidence of polymicrobic flora in most chronic and acute wounds give credence to the value of identifying one or more bacterial pathogens from wound cultures. The early recognition of causative agents of wound infections can assist wound care practitioners in taking appropriate measures. Furthermore, faulty collagen formation arises from increased bacterial burden and results in over-vascularized friable loose granulation tissue that usually leads to wound breakdown.

Accurate and clinically relevant wound assessment is an important clinical tool, but this process currently remains a substantial challenge. Current visual assessment in clinical practice only provides a gross view of the wound site (e.g., presence of purulent material and crusting). Current best clinical practice fails to adequately use the critically important objective information about underlying key biological changes that are occurring at the tissue and cellular level (e.g., contamination, colonization, infection, matrix remodeling, inflammation, bacterial/microbial infection, and necrosis) since such indices are i) not easily available at the time of the wound examination and ii) they are not currently integrated into the conventional wound management process. Direct visual assessment of wound health status using white light relies on detection of color and topographical/textural changes in and around the wound, and thus may be incapable and unreliable in detecting subtle changes in tissue remodeling. More importantly, direct visual assessment of wounds often fails to detect the presence of bacterial infection, since bacteria are occult under white light illumination. Infection is diagnosed clinically with microbiological tests used to identify organisms and their antibiotic susceptibility. Although the physical indications of bacterial infection can be readily observed in most wounds using white light (e.g., purulent exudate, crusting, swelling, erythema), this is often significantly delayed, and the patient is already at increased risk of morbidity (and other complications associated with infection) and mortality. Therefore, standard white light direct visualization fails to detect the early presence of the bacteria themselves or identify the types of bacteria within the wound.

Wound progression is currently monitored manually. The National Pressure Ulcer Advisory Panel (NPUAP) developed the Pressure Ulcer Scale for Healing (PUSH) tool that outlines a five-step method of characterizing pressure ulcers. This tool uses three parameters to determine a quantitative score that is then used to monitor the pressure ulcer over time. The qualitative parameters include wound dimensions, tissue type, and the amount of exudate or discharge, and thermal readings present after the dressing is removed. A wound can be further characterized by its odor and color. Such an assessment of wounds currently does not include critical biological and molecular information about the wound. Therefore, all descriptions of wounds are somewhat subjective and noted by hand by either the attending physician or the nurse.

What is desirable is a robust, cost-effective non-invasive and rapid imaging-based method or device for collecting wound data and providing an analysis in real-time. The data and analysis can be used to objectively assess wounds for changes at the biological, biochemical and cellular levels and to rapidly, sensitively and non-invasively detecting the earliest presence of bacteria/microorganisms within wounds. Such a method or device for detection of critical biological tissue changes in wounds may serve an adjunctive role with conventional clinical wound management methods in order to guide key clinico-pathological decisions in patient care. Such a device may be compact, portable and capable of real-time non-invasive and/or non-contact interrogation of wounds in a safe and convenient manner, which may allow it to fit seamlessly into routine wound management practice and user friendly to the clinician, nurse and wound specialist. This may also include use of this device in the home-care environment (including self-use by a patient), as well as in military battlefield environments. In addition, such an image-based device may provide an ability to monitor wound treatment response and healing in real-time by incorporating valuable 'biologically-informed' image-guidance into the clinical wound assessment process. This may ultimately lead to potential new diagnosis, treatment planning, treatment response monitoring and thus 'adaptive' intervention strategies which may permit enhancement of wound-healing response at the individual patient level. Precise identification of the systemic, local, and molecular factors underlying the wound healing problem in individual patients may allow better tailored treatment.

In accordance with the present teachings, methods of analysis for data collected from a wound are provided. For example, the collection of fluorescence image data appears to be promising for improving clinical wound assessment and management. When excited by short wavelength light (e.g., ultraviolet or short visible wavelengths), most endogenous biological components of tissues (e.g., connective tissues such collagen and elastins, metabolic co-enzymes, proteins, etc.) produce fluorescence of a longer wavelength, in the ultraviolet, visible, near-infrared and infrared wavelength ranges.

Tissue autofluorescence imaging provides a unique means of obtaining biologically relevant information of normal and diseased tissues in real-time, thus allowing differentiation between normal and diseased tissue states, as well as the volume of the diseased tissue. This is based, in part, on the inherently different light-tissue interactions (e.g., abosption and scattering of light) that occur at the bulk tissue and cellular levels, changes in the tissue morphology and alterations in the blood content of the tissues. In tissues, blood is a major light absorbing tissue component (i.e., a chromophore). This type of technology is suited for imaging disease in hollow organs (e.g., GI tract, oral cavity, lungs, bladder) or exposed tissue surfaces (e.g., skin). An autofluorescence imaging device in accordance with the present disclosure may collect wound data that provides/allows rapid, non-invasive and non-contact real-time analysis of wounds and their composition and components, to detect and exploit the rich biological information of the wound to improve clinical care and management.

A device in accordance with the present disclosure: 1) provides image-guidance for tissue sampling, detecting clinically-significant levels of pathogenic bacteria and wound infection otherwise overlooked by conventional sampling and 2) provides image-guidance for wound treatment, accelerating wound closure compared with conventional therapies and quantitatively tracking long-term changes in bacterial bioburden and distribution in wounds.

U.S. Pat. No. 9,042,967 B2 to DaCosta et al., entitled "Device and Method for Wound Imaging and Monitoring," and issued on May 26, 2015, discloses at least some aspects of a device configured to collect data for objectively assessing wounds for changes at the biological, biochemical and cellular levels and for rapidly, sensitively and non-invasively detecting the earliest presence of bacteria/microorganisms within wounds. This patent claims priority to PCT Application No. PCT/CA2009/000680 filed on May 20, 2009, and to U.S. Provisional Patent Application No. 61/054,780, filed on May 20, 2008. The entire content of each of these above-identified patents, patent applications, and patent application publications is incorporated herein by reference.

In accordance with one aspect of the present teachings, a handheld portable device to examine skin and wounds in real-time is provided. The device instantly detects, visualizes, and analyzes bacteria and tissue composition. The device is a compact, handheld, device for noncontact and noninvasive imaging. It captures both white light (WL) and autofluorescence (AF) signals produced by tissue components and bacteria without the use of contrast agents. Although capable of detecting AF signals without use of contrast agents, one of ordinary skill in the art will understand that the devices disclosed herein can be used with contrast agents if desired. In addition to white light and fluorescence, the device also may capture thermal data from the imaged area. The device may be further configured to analyze the white light, fluorescence, and thermal data, correlate such data, and provide an output based on the correlation of the data, such as, for example, an indication of wound status, wound healing, wound infection, bacterial load, or other diagnostic information upon which an intervention strategy may be based.

The device may be configured to create and/or display composite images including green AF, produced by endogenous connective tissues (e.g., collagen, elastin) in skin, and red AF, produced by endogenous porphyrins in clinically relevant bacteria such as *Staphylococcus aureus*. Siderophores/pyoverdins in other species such as *Pseudomonas aruginosa* appear blue-green in color with in vivo AF imaging. The device may provide visualization of bacterial presence, types, distribution, amounts in and around a wound as well as key information surrounding tissue composition (collagen, tissue viability, blood oxygen saturation). For example, the device may provide imaging of collagen composition in and around skin in real-time (via AF imaging).

In accordance with various exemplary embodiments of the present disclosure, the device may be configured to accurately detect and measure bacterial load in wounds in real-time, guide treatment decisions, and track wound healing over the course of antibacterial treatment. Additionally, bioluminescence imaging (BLI) may be used to correlate absolute bacterial load with FL signals obtained using the handheld device. The device may produce a uniform illumination field on a target area to allow for imagining/quantification of bacteria, collagen, tissue viability, and oxygen saturation.

The device may produce high-quality, focused images. The device may include software that provides macro zoom correction, auto-focus, auto white balance, wide dynamic range, noise reduction, image stabilization, and FL image calibration. In some embodiments, the device operates at an ambient temperature between about 0-35° C.

The device may be independent and self-contained. It may interface with computers, printers and EMR systems.

In accordance with one exemplary embodiment of the present disclosure, the device is configured to image bacteria in real-time (via, for example, fluorescence imaging), permitting ready identification of bacteria types, their location, distribution and quantity in accepted units of measurement and allowing identification of and distinction between several different species of bacteria. For example, autofluorescence imaging may be used to visualize and differentiate *Pseudomonas aruginosa* (which fluoresces a greenish-blue colour when excited by 405 nm light from the device) from other bacteria (e.g., *Staphylococcus aureus*) that predominantly fluoresce a red/orange colour under the same excitation wavelength. In one exemplary embodiment the device's camera sensor and built in fluorescence multiband pass emission filter produce fluorescence images of bacteria (in wounds or normal skin) and *Pseudomonas aruginosa* appear greenish-blue in colour while other bacteria emit a red/orange colour. The device detects differences in the autofluorescence emission of different endogenous molecules (called fluorophores) between the different bacteria.

In accordance with another exemplary embodiment of the present disclosure, the device is configured to identify or provide an indication of tissue viability in real-time (via fluorescence imaging). For example, blood preferentially absorbs 405 nm light compared with other visible wavelengths. Tissues which are perfused by blood are considered viable and can be differentiated from devitalized (poorly perfused) tissues using fluorescence imaging. Using 405 nm light from a device in accordance with the present teachings to illuminate a wound, the device can be configured with a multiband pass emission filter to detect the amount of 405 nm light that is absorbed or reflected from the tissues. Viable tissue contains blood that highly absorbs 405 nm light resulting in an image with low levels of 405 nm light, whereas nonviable (or devitalized) tissues do not contain sufficient blood and 405 nm is less absorbed. Thus, in an image of a wound where viable and nonviable tissues are present, the user will recognize viable tissues (from nonviable tissues) based on the relative amount of 405 nm light in the image, the viable tissues appearing darker compared with the nonviable tissues. In addition, in the green fluorescence "channel" of the resultant image (of the wound), viable tissues will appear less green fluorescent compared with nonviable tissues because viable tissues will preferentially absorb more of the 405 nm excitation light due to more blood being present, compared with nonviable tissues. Thus, while both viable and nonviable tissues in a resultant image obtained by the device may contain similar amounts of green fluorescent connective tissues (i.e., collagens), viable tissue will have less 405 nm excitation light to stimulate the connective tissue autofluorescence than nonviable tissues. The result is that viable tissues will have less green connective tissue fluorescence than non-viable tissues in the same image. The user will appreciate this difference visually during imaging with the device.

In accordance with another aspect of the present disclosure, the device is configured to capture and generate images and videos that provide a map or other visual display of user selected parameters. Such maps or displays may correlate, overlay, co-register or otherwise coordinate data generated by the device based on input from one or more device sensors. Such sensors may include, for example, camera sensors configured to detect white light and/or fluorescent images and thermal sensors configured to detect heat signatures of a target. For example, the device may be configured to display color images, image maps, or other maps of user selected parameters such as, for example, bacteria location and/or biodistribution, collagen location, location and differentiation between live tissues and dead tissues, differentiation between bacterial species, location and extent of blood, bone, exudate, temperature and wound area/size. These maps or displays may be output by the device based on the received signals and may be produced on a single image with or without quantification displays. The user-selected parameters shown on the map may be correlated with one or more wound parameters, such as shape, size, topography, volume, depth, and area of the wound. For example, in accordance with one exemplary embodiment, it is possible to use a 'pseudo-coloured' display of the fluorescence images/videos of wounds to color-code bacteria fluorescence (one colour) and connective tissues (another colour) etc. This may be accomplished by, for example, using a pixel-by-pixel coloring based on the relative amount of 405 nm light in the Blue channel of the resultant RGB image, green connective tissue fluorescence in the Green channel, and red bacteria fluorescence in Red channel. Additionally and/or alternatively, this may be accomplished by displaying the number of pixels in a given image for each of the blue, green and red channels which would represent amount of blood in tissue, amount of connective tissues, and amount of bacteria, respectively.

In accordance with one aspect of the present disclosure, the device may be configured to create and output reports regarding the collected data. For example, in accordance with one exemplary embodiment, the device user can generate a wound status report, which may include, for example, date/time, patient ID, images, etc. The user can export or print images, to a selected network, computer, printer when connected to cradle, and/or via USB to computer. The reports may be generated by the handheld device, by exporting data to a computer for processing and generation of reports, or by a combination of the two. Further, such reports, or the data contained therein, may form the basis of recommended intervention or treatment strategies. Reports may include, for example, medical reports, digital reports, reports that encompass handwritten input from clinicians (e.g., via tablet input, etc.). The reports may include various types of data including, for example, the identification of wound parameters and the tracking of these parameters over time. For example, the reports may identify and track changes in wound size, wound shape, wound topography, wound volume, wound area, bacterial load of the wound, location of bacteria within the wound, presence of exposed bone, blood, connective and other tissues, wound temperature, location of the wound on the patient, number of wounds on the patient, date of wound examination, patient identification, medications administered to the patient, interventional strategies and therapies as administered and as changed over time in response to changing wound parameters, etc. For example, the device may generate a report that tracks a patient's wound and skin status changes, including for example, wound size and bacterial burden over time. Further, the data collected may be used to generate a database that provides clinical data regarding wound parameters and the efficacy of various wound intervention/treatment strategies. Additionally, the device may be configured to integrate collected data/images/videos into the reports and, alternatively or additionally, include such reports and data/images/videos into a patient's electronic medical record (EMR). This process may be wirelessly, via the use of transfer cables, and the system also may be configured to upload the reports automatically.

The device has a memory sufficient to store several images/videos. In addition to internal memory, the device may include a Micro SD card interface for additional storage and firmware development. The device can inform the user of low memory capacity. The device may also include a data safeguard that will prompt a user to export files in the case of low memory availability.

In accordance with one aspect of the present disclosure, a method and device for fluorescence-based imaging and monitoring is disclosed. One exemplary embodiment of the device is a portable optical digital imaging device. The device may utilize a combination of white light, tissue fluorescence and reflectance imaging, and thermal imaging, and may provide real-time wound imaging, assessment, recordation/documentation, monitoring and/or care management. The device may be handheld, compact and/or lightweight. This device and method may be suitable for monitoring of wounds in humans and animals.

The device may generally comprise: i) one or more excitation/illumination light sources and ii) a detector device (e.g., a digital imaging detector device), which may be combined with one or more optical emission filters, or spectral filtering mechanisms, and which may have a view/control screen (e.g., a touch-sensitive screen), image capture and zoom controls. The device may also have: iii) a wired and/or wireless data transfer port/module, iv) an electrical power source and power/control switches, and/or v) an enclosure, which may be compact and/or light weight, and which may have a mechanism for attachment of the detector device and/or a handle grip. The excitation/illumination light sources may be LED arrays emitting light at about 405 nm (e.g., +/−5 nm), and may be coupled with additional band-pass filters centered at about 405 nm to remove/minimize the side spectral bands of light from the LED array output so as not to cause light leakage into the imaging detector with its own optical filters. The digital imaging detector device may be a digital camera, for example having at least an ISO800 sensitivity, but more preferably an ISO3200 sensitivity, and may be combined with one or more optical emission filters, or other equally effective (e.g., miniaturized) mechanized spectral filtering mechanisms (e.g., acousto-optical tunable filter or liquid crystal tunable filter). The digital imaging detector device may have a touch-sensitive viewing and/or control screen, image capture and zoom controls. The enclosure may be an outer hard plastic or polymer shell, enclosing the digital imaging detector device, with buttons such that all necessary device controls may be accessed easily and manipulated by the user. Miniature heat sinks or small mechanical fans, or other heat dissipating devices may be embedded in the device to allow excess heat to be removed from the excitation light sources if required. The complete device, including all its embedded accessories and attachments, may be powered using standard AC/DC power and/or by rechargeable battery pack. As discussed further below, the battery pack may be recharged with a charging stand.

The complete device may also be attached or mounted to an external mechanical apparatus (e.g., tripod, or movable stand with pivoting arm) allowing mobility of the device within a clinical room with hands-free operation of the device. Alternatively, the device may be provided with a mobile frame such that it is portable. The device may be cleaned using moist gauze wet with water, while the handle may be cleansed with moist gauze wet with alcohol. Additional appropriate cleaning methods will be apparent to those of ordinary skill in the art. The device may include software allowing a user to control the device, including control of imaging parameters, visualization of images, storage of image data and user information, transfer of images and/or associated data, and/or relevant image analysis (e.g., diagnostic algorithms). The device may also include one or more buttons/switches allowing a user to switch between white light and fluorescent light imaging.

A schematic diagram of an example of the device is shown in FIG. 1. The device is shown positioned to image a target object 10 or target surface. In the example shown, the device has a digital image acquisition device 1, such as digital camera, video recorder, camcorder, cellular telephone with built-in digital camera, 'Smart' phone with a digital camera, personal digital assistant (PDA), laptop/PC with a digital camera, or a webcam. The digital image acquisition device 1 has a lens 2, which may be aligned to point at the target object 10 and may detect the optical signal that emanates from the object 10 or surface. The device has an optical filter holder 3 which may accommodate one or more optical filters 4. Each optical filter 4 may have different discrete spectral bandwidths and may be band-pass filters. These optical filters 4 may be selected and moved in from of the digital camera lens to selectively detect specific optical signals based on the wavelength of light. The device may include light sources 5 that produce excitation light to illuminate the object 10 in order to elicit an optical signal (e.g., fluorescence) to be imaged with, for example, blue light (e.g., 400-450 nm), or any other combination of single or multiple wavelengths (e.g., wavelengths in the ultraviolet/visible/near infrared/infrared ranges). The light source 5 may comprise a LED array, laser diode and/or filtered lights arranged in a variety of geometries. The device may include a method or apparatus 6 (e.g., a heatsink or a cooling fan) to dissipate heat and cool the illumination light sources 5. The device may include a method or apparatus 7 (e.g., an optical band-pass filter) to remove any undesirable wavelengths of light from the light sources 5 used to illuminate the object 10 being imaged. The device may include a method or apparatus 8 to use an optical means (e.g., use of compact miniature laser diodes that emit a collimated light beam) to measure and determine the distance between the imaging device and the object 10. For example, the device may use two light sources, such as two laser diodes, as part of a triangulation apparatus to maintain a constant distance between the device and the object 10. Other light sources may be possible. The device may also use ultrasound, or a physical measure, such as a ruler, to determine a constant distance to maintain. In accordance with another exemplary embodiment, the device may use a rangefinder to determine the appropriate position of the device relative to the wound to be imaged. The device may also include a method or apparatus 9 (e.g., a pivot) to permit the manipulation and orientation of the excitation light sources 5, 8 so as to manoeuvre these sources 5,8 to change the illumination angle of the light striking the object 10 for varying distances.

The target object 10 may be marked with a mark 11 to allow for multiple images to be taken of the object and then being co-registered for analysis. The mark 11 may involve, for example, the use of exogenous fluorescence dyes of different colours which may produce multiple distinct optical signals when illuminated by the light sources 5 and be detectable within the image of the object 10 and thus may permit orientation of multiple images (e.g., taken over time) of the same region of interest by co-registering the different colours and the distances between them. The digital image acquisition device 1 may include one or more of: an interface 12 for a head-mounted display; an interface 13 for an external printer; an interface 14 for a tablet computer, laptop computer, desk top computer or other computer device; an interface 15 for the device to permit wired or wireless transfer of imaging data to a remote site or another device; an interface 16 for a global positioning system (GPS) device; an interface 17 for a device allowing the use of extra memory; and an interface 18 for a microphone.

The device may include a power supply 19 such as an AC/DC power supply, a compact battery bank, or a rechargeable battery pack. Alternatively, the device may be adapted for connecting to an external power supply. The device may have a housing 20 that houses all the components in one entity. The housing 20 may be equipped with a means of securing any digital imaging device within it. The housing 20 may be designed to be handheld, compact, and/or portable. The housing 20 may be one or more enclosures. The housing 20 may be comprised of a rugged material so that the device is tough and resistant to inadvertent drops by a user. Additionally, the housing 20 may include covers for any external ports of the device.

Figure 2A:
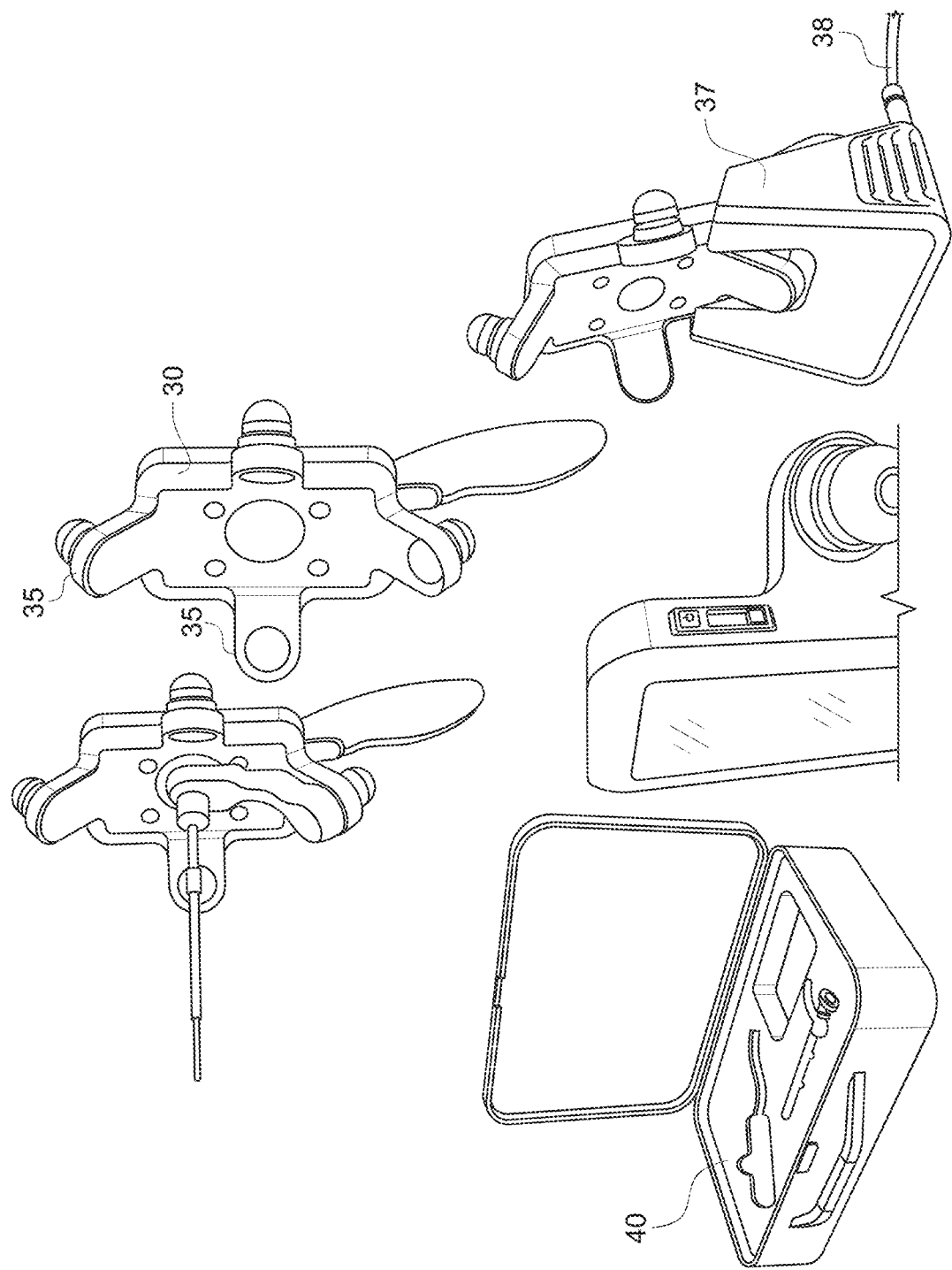
FIG. 2A shows an exemplary charging stand for use with a device for fluorescence-based monitoring in accordance with the present disclosure.

In accordance with one exemplary embodiment, the device may be charged while it is stationed in a charging stand, such as charging stand 30 shown in FIG. 2A. The charging stand 30 may include, for example, one or more arms 35 to receive and securely hold the device. Additionally, the charging stand 30 may be attached to a docking port 37, which may include a cable 38 that is plugged into an outlet for charging the device and/or recharging a battery pack in the device. The device, charging stand 30, and/or docking port 37 may be stored in a case, such as case 40 shown in FIG. 2A.

Figure 2B:
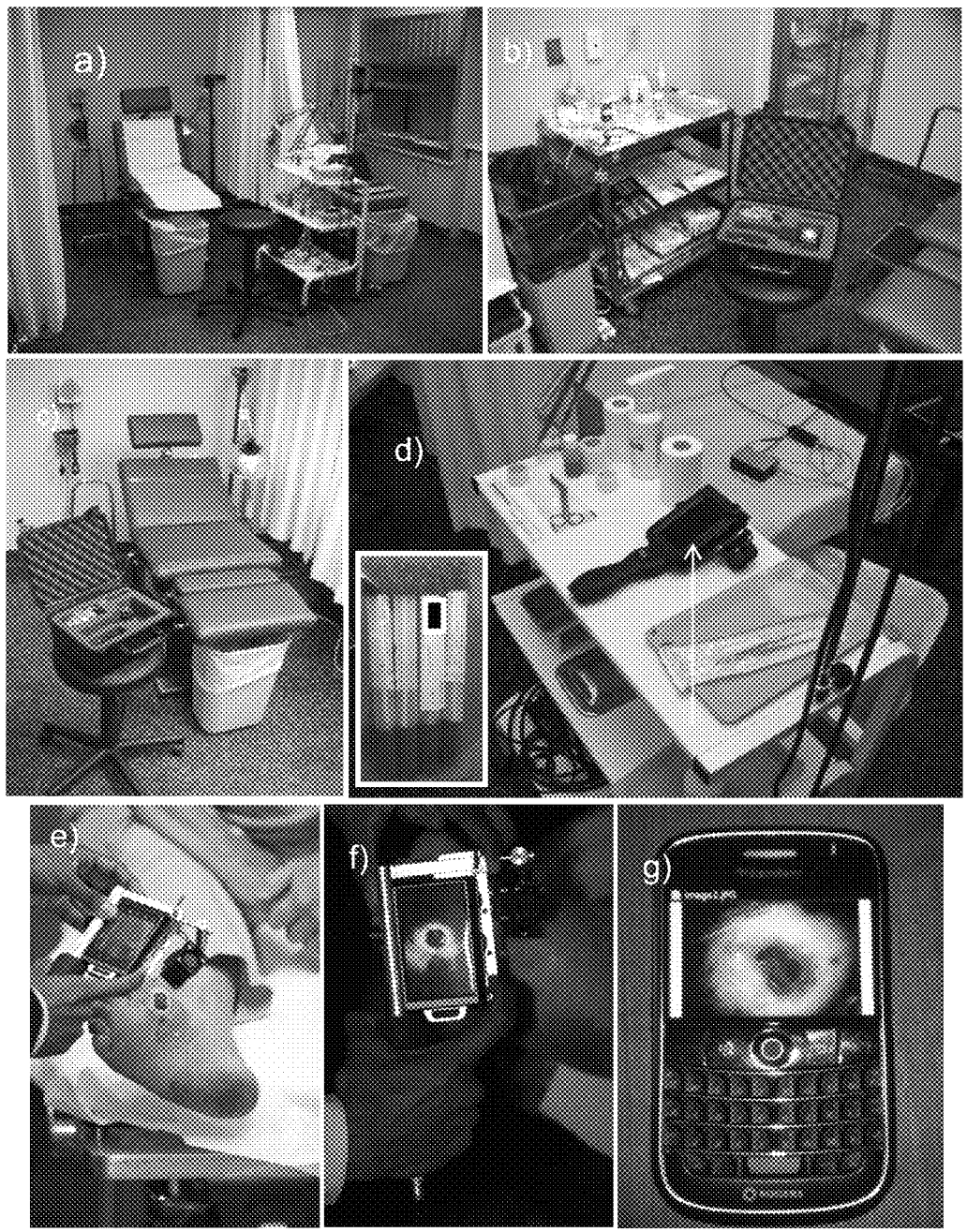
FIG. 2B shows an example of a clinical wound care facility using a device for fluorescence-based monitoring in accordance with the present disclosure.

FIG. 2B shows an example of a device in accordance with the present disclosure in a typical wound care facility. Inset a) shows a typical clinical wound care facility, showing the examination chair and accessory table. Insets b-c) show an example of the device in its hard-case container, similar to the case 40 as shown in FIG. 2A. The device may be integrated into the facility's routine wound care practice allowing real-time imaging of a patient. Inset d) shows an example of the device (arrow) placed on the "wound care cart" to illustrate the size of the device. Inset e) shows that the device may be used to image under white light illumination, while inset f) shows the device being used to take fluorescence images of a wound under dimmed room lights. Inset g) shows that the device may be used in telemedicine/telehealth infrastructures, for example fluorescence images of a patient's wounds may be sent by email to a wound care specialist at another hospital, via a wireless communication device, such as a Smartphone, using a wireless/WiFi internet connection. Using this device, high-resolution fluorescence images may be sent as email attachments to wound care specialists from remote wound care sites for immediate consultation with clinical experts, microbiologists, etc. at specialized clinical wound care and management centers.

An example of a device for fluorescence-based monitoring in accordance with the present disclosure is described below. All examples are provided for the purpose of illustration only and are not intended to be limiting. Parameters such as wavelengths, dimensions, and incubation time described in the examples may be approximate and are provided as examples only.

In this example, the device uses two violet/blue light (e.g., 405 nm+/−10 nm emission, narrow emission spectrum) LED arrays (Opto Diode Corporation, Newbury Park, Calif.), each situated on either side of the imaging detector assembly as the excitation or illumination light sources. These arrays have an output power of approximately 1 Watt each, emanating from a 2.5×2.5 cm$^2$, with a 70-degree illuminating beam angle. The LED arrays may be used to illuminate the tissue surface from a distance of about 10 cm, which means that the total optical power density on the skin surface is about 0.08 W/cm$^2$. At such low powers, there is no known potential harm to either the target wound or skin surface, or the eyes from the excitation light. However, it may be inadvisable to point the light directly at any individual's eyes during imaging procedures. It should also be noted that 405 nm light does not pose a risk to health according to international standards formulated by the International Electrotechnical Commission (IEC), as further detailed on the website:

http://www.iec.ch/online_news/etech/arch_2006/etech_0906/focus.htm

The one or more light sources may be articulated (e.g., manually) to vary the illumination angle and spot size on the imaged surface, for example by using a built-in pivot, and are powered for example through an electrical connection to a wall outlet and/or a separate portable rechargeable battery pack. Excitation/illumination light may be produced by sources including, but not limited to, individual or multiple light-emitting diodes (LEDs) in any arrangement including in ring or array formats, wavelength-filtered light bulbs, or lasers. Selected single and multiple excitation/illumination light sources with specific wavelength characteristics in the ultraviolet (UV), visible (VIS), far-red, near infrared (NIR) and infrared (IR) ranges may also be used, and may be composed of a LED array, organic LED, laser diode, or filtered lights arranged in a variety of geometries. Excitation/illumination light sources may be 'tuned' to allow the light intensity emanating from the device to be adjusted while imaging. The light intensity may be variable. The LED arrays may be attached to individual cooling fans or heat sinks to dissipate heat produced during their operation. The LED arrays may emit narrow 405 nm light, which may be spectrally filtered using a commercially available band-pass filter (Chroma Technology Corp, Rockingham, Vt., USA) to reduce potential 'leakage' of emitted light into the detector optics. When the device is held above a tissue surface (e.g., a wound) to be imaged, the illuminating light sources may shine a narrow-bandwidth or broad-bandwidth violet/blue wavelength or other wavelength or wavelength band of light onto the tissue/wound surface thereby producing a flat and homogeneous field within the region-of-interest. The light may also illuminate or excite the tissue down to a certain shallow depth. This excitation/illumination light interacts with the normal and diseased tissues and may cause an optical signal (e.g., absorption, fluorescence and/or reflectance) to be generated within the tissue.

By changing the excitation and emission wavelengths accordingly, the imaging device may interrogate tissue components (e.g., connective tissues and bacteria in a wound) at the surface and at certain depths within the tissue (e.g., a wound). For example, by changing from violet/blue (~400-500 nm) to green (~500-540 nm) wavelength light, excitation of deeper tissue/bacterial fluorescent sources may be achieved, for example in a wound. Similarly, by detecting longer wavelengths, fluorescence emission from tissue and/or bacterial sources deeper in the tissue may be detected at the tissue surface. For wound assessment, the ability to interrogate surface and/or sub-surface fluorescence may be useful, for example in detection and potential identification of bacterial contamination, colonization, critical colonization and/or infection, which may occur at the surface and often at depth within a wound (e.g., in chronic non-healing wounds). In one example, referring to FIG. 3, inset c) shows the detection of bacteria below the skin surface (i.e., at depth) after wound cleaning. This use of the device for detecting bacteria at the surface and at depth within a wound and surrounding tissue may be assessed in the context of other clinical signs and symptoms used conventionally in wound care centers.

Figure 4:
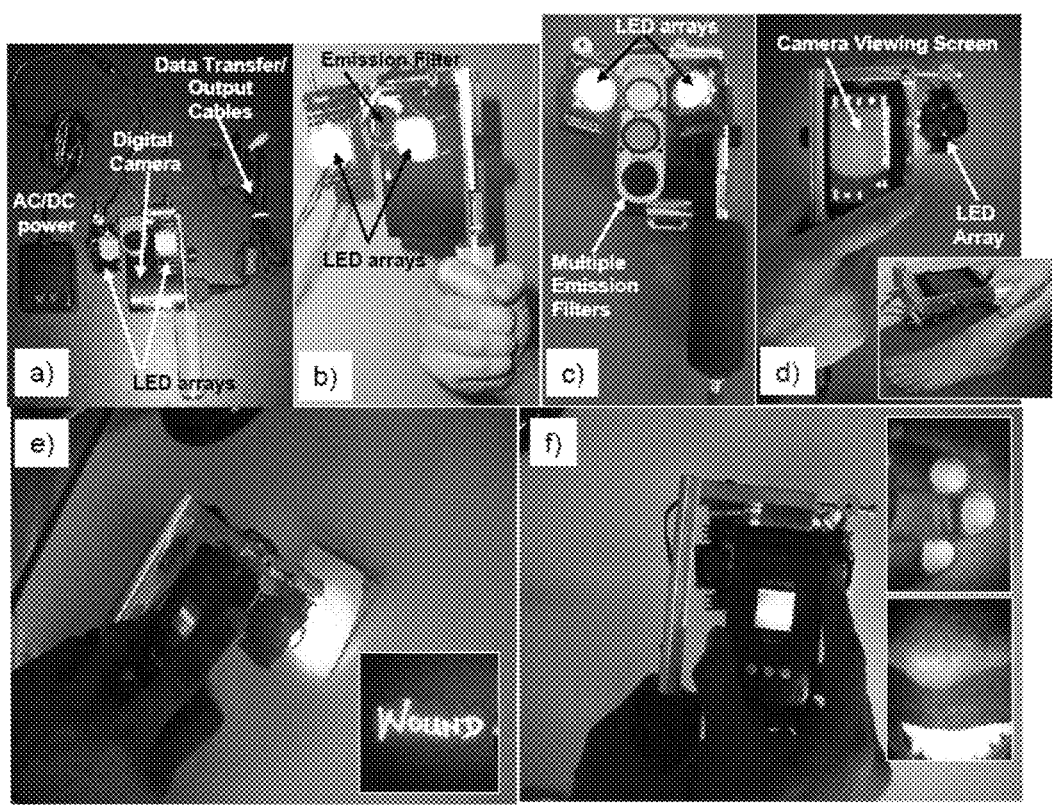
FIG. 4 shows images of an exemplary handheld embodiment of a device for fluorescence-based monitoring in accordance with the present disclosure.

Example embodiments of the device are shown in FIG. 4. The device may be used with any standard compact digital imaging device (e.g., a charge-coupled device (CCD) or complementary metal-oxide-semiconductor (CMOS) sensors) as the image acquisition device. The example device shown in a) has an external electrical power source, the two LED arrays for illuminating the object/surface to be imaged, and a commercially available digital camera securely fixed to light-weight metal frame equipped with a convenient handle for imaging. A multi-band filter is held in front of the digital camera to allow wavelength filtering of the detected optical signal emanating from the object/surface being imaged. The camera's video/USB output cables allow transfer of imaging data to a computer for storage and subsequent analysis. This example uses a commercially-available 8.1-megapixel Sony digital camera (Sony Cybershot DSC-T200 Digital Camera, Sony Corporation, North America). This camera may be suitable because of i) its slim vertical design which may be easily integrated into the enclosure frame, ii) its large 3.5-inch widescreen touch-panel LCD for ease of control, iii) its Carl Zeiss 5× optical zoom lens, and iv) its use in low light (e.g., ISO 3200). The device may have a built-in flash which allows for standard white light imaging (e.g., high-definition still or video with sound recording output). Camera interface ports may support both wired (e.g., USB) or wireless (e.g., Bluetooth, WiFi, and similar modalities) data transfer or 3$^{rd}$ party add-on modules to a variety of external devices, such as: a head-mounted display, an external printer, a tablet computer, laptop computer, personal desk top computer, a wireless device to permit transfer of imaging data to a remote site/other device, a global positioning system (GPS) device, a device allowing the use of extra memory, and a microphone. The digital camera is powered by rechargeable batteries, or AC/DC powered supply. The digital imaging device may include, but is not limited to, digital cameras, webcams, digital SLR cameras, camcorders/video recorders, cellular telephones with embedded digital cameras, Smartphones™, personal digital assistants (PDAs), and laptop computers/tablet PCs, or personal desk-top computers, all of which contain/or are connected to a digital imaging detector/sensor.

This light signal produced by the excitation/illumination light sources may be detected by the imaging device using optical filter(s) (e.g., those available from Chroma Technology Corp, Rockingham, Vt., USA) that reject the excitation light but allow selected wavelengths of emitted light from the tissue to be detected, thus forming an image on the display. There is an optical filter holder attached to the enclosure frame in front of the digital camera lens which may accommodate one or more optical filters with different discrete spectral bandwidths, as shown in insets b) and c) of FIG. 4. Inset b) shows the device with the LED arrays turned on to emit bright violet/blue light, with a single emission filter in place. Inset c) shows the device using a multiple-optical filter holder used to select the appropriate filter for desired wavelength-specific imaging. Inset d) shows the device being held in one hand while imaging the skin surface of a foot.

These band-pass filters may be selected and aligned in front of the digital camera lens to selectively detect specific optical signals from the tissue/wound surface based on the wavelength of light desired. Spectral filtering of the detected optical signal (e.g., absorption, fluorescence, reflectance) may also be achieved, for example, using a liquid crystal tunable filter (LCTF), or an acousto-optic tunable filter (AOTF) which is a solid-state electronically tunable spectral band-pass filter. Spectral filtering may also involve the use of continuous variable filters, and/or manual band-pass optical filters. These devices may be placed in front of the imaging detector to produce multispectral, hyperspectral, and/or wavelength-selective imaging of tissues.

The device may be modified by using optical or variably oriented polarization filters (e.g., linear or circular combined with the use of optical wave plates) attached in a reasonable manner to the excitation/illumination light sources and the imaging detector device. In this way, the device may be used to image the tissue surface with polarized light illumination and non-polarized light detection or vice versa, or polarized light illumination and polarized light detection, with either white light reflectance and/or fluorescence imaging. This may permit imaging of wounds with minimized specular reflections (e.g., glare from white light imaging), as well as enable imaging of fluorescence polarization and/or anisotropy-dependent changes in connective tissues (e.g., collagens and elastin) within the wound and surrounding normal tissues. This may yield useful information about the spatial orientation and organization of connective tissue fibers associated with wound remodeling during healing.

All components of the imaging device may be integrated into a single structure, such as an ergonomically designed enclosed structure with a handle, allowing it to be comfortably held with one or both hands. The device may also be provided without any handle. The device may be light weight, portable, and may enable real-time digital imaging (e.g., still and/or video) of any target surface (for example, the skin and/or oral cavity, which is also accessible) using white light, fluorescence and/or reflectance imaging modes. The device may be scanned across the body surface for imaging by holding it at variable distances from the surface, and the device may be used in a lit environment/room to image white light reflectance/fluorescence. The device may also be used in a dim or dark environment/room to optimize the tissue fluorescence signals and to minimize background signals from room lights. The device may be used for direct (e.g., with the unaided eye) or indirect (e.g., via the viewing screen of the digital imaging device) visualization of wounds and surrounding normal tissues.

The device may also be embodied as not being handheld or portable, for example as being attached to a mounting mechanism (e.g., a tripod or stand) for use as a relatively stationary optical imaging device for white light, fluorescence and reflectance imaging of objects, materials, and surfaces (e.g., a body). This may allow the device to be used on a desk or table or for 'assembly line' imaging of objects, materials and surfaces. In some embodiments, the mounting mechanism may be mobile.

Other features of this device may include the capability of digital image and video recording, possibly with audio, methods for documentation (e.g., with image storage and analysis software), and wired or wireless data transmission for remote telemedicine/E-health needs.

In some embodiments, the image acquisition device may be a mobile device, such as a cellular telephone or smartphone. In these embodiments, the mobile device is used to obtain the white light and/or fluorescent images. As discussed further below, the image acquisition device may also include an adaptor for attachment to the mobile device. The insets e) and f) of FIG. 4 show an embodiment where the image acquisition device is a mobile communication device, such as, for example, a cellular telephone. The cellular telephone used in this example is a Samsung Model A-900, which is equipped with a 1.3 megapixel digital camera. As illustrated in FIG. 4, the telephone is fitted into the holding frame for convenient imaging. Inset e) shows the use of the device to image a piece of paper with fluorescent ink showing the word "Wound". Inset f) shows imaging of fluorescent ink stained fingers, and detection of the common skin bacteria *P. acnes*. The images from the cellular telephone (or smartphone) may be sent wirelessly to another cellular telephone, (smartphone) or wirelessly (e.g., via Bluetooth connectivity) to a personal computer for image storage and analysis. This demonstrates the capability of the device to perform real-time handheld fluorescence imaging and wireless transmission to a remote site/person as part of a telemedicine/E-health wound care infrastructure.

In order to demonstrate the capabilities of the image acquisition device in wound care and other relevant applications, a number of feasibility experiments were conducted using the particular example described above. It should be noted that all fluorescence imaging experiments used a Sony camera (Sony Cybershot DSC-T200 Digital Camera, Sony Corporation, North America) as described above. The camera settings were set so that images were captured without a flash, and with the 'Macro' imaging mode set. Images were captured at 8 megapixels. The flash was used to capture white light reflectance images. All images were stored on the xD memory card for subsequent transfer to a personal computer for long-term storage and image analysis.

In one exemplary embodiment, white light reflectance and fluorescence images/movies captured with the device were imported into Adobe Photoshop for image analysis. However, image analysis software was designed using MatLab™ (Mathworks) to allow a variety of image-based spectral algorithms (e.g., red-to-green fluorescence ratios, etc.) to be used to extract pertinent image data (e.g., spatial and spectral data) for quantitative detection/diagnostic value. Image post-processing also included mathematical manipulation of the images.

Figure 5A:
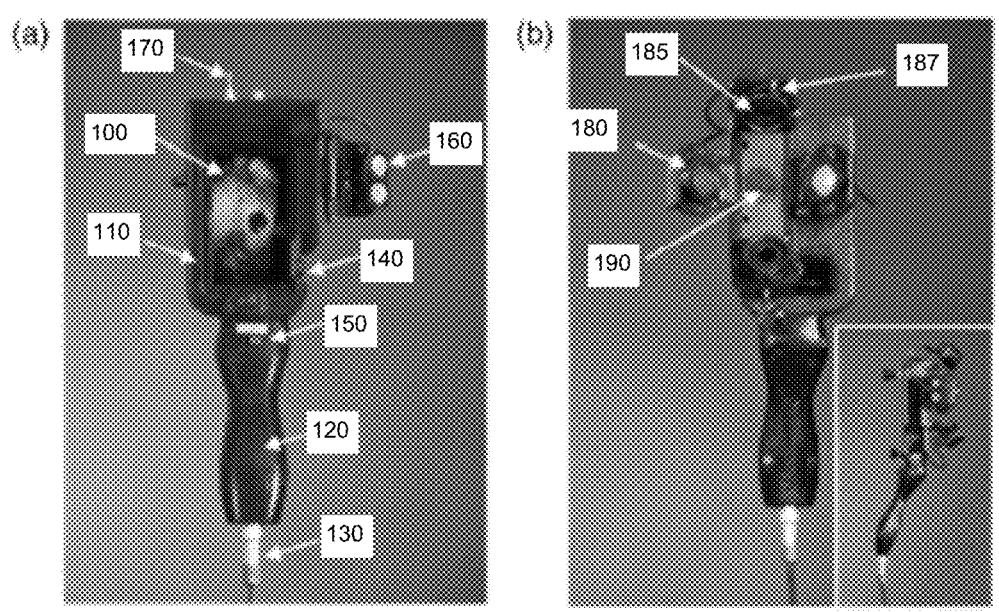

In accordance with another exemplary embodiment of the present disclosure, a handheld device for collection of data from a wound includes a low-cost, consumer-grade, Super HAD™ charge-coupled device (CCD) sensor-based camera (Model DSC-T900, Sony Corp., Japan), with a 35 to 140 mm equivalent 4x zoom lens housed in a plastic body and powered by rechargeable batteries. An exemplary embodiment of this handheld imaging device is shown in FIG. 5A. Inset (a) of FIG. 5A is a view of the user-facing side of the device showing a wound fluorescence (FL) image displayed in real time on a liquid-crystal (LC) display screen 100 in high definition. As shown in inset (a) of FIG. 5A, the device includes a housing 110 attached to a handle 120. The housing 110 may be plastic, or any conventional material well-known in the art. Additionally, the handle 120 may be connected to a power cable 130 for power, as discussed above. The housing 110 may include an image capture button 140, to control the image captured on the display screen 100, and an on/off switch 150. As shown in inset (a) of FIG. 5A, the device may also include heat dissipating fans 160 to allow excess heat to be removed from the device, if required. Furthermore, a toggle switch 170 may be provided so that a user can switch between white light imaging and fluorescent imaging.

Inset (b) of FIG. 5A is a view of the patient-facing side of the device showing a dual excitation LED array assembly 180 that includes an optical filter. The LED array assembly 180 may be white light (WL) and 405-nm LED arrays that provide illumination of the wound. The WL LEDs may be broadband LEDs that are electrically powered by a standard AC 125V source and that provide illumination during WL imaging. The FL LEDs may be two monochromatic violet/blue ($\lambda$=405 nm+/−20 nm) LED arrays that provide 4 Watt excitation light power during FL imaging. WL and FL images are detected by a high-sensitivity CCD sensor mounted with a dual band FL filter in front of the camera lens to block excitation light reflected from the skin surface. Additionally, the device may include a dual white light LED array 185 coupled to an iris 187. A FL emission filter 190 may also be disposed on the back side of the device. The FL emission filter 190 may be placed in front of the CCD sensor.

The device of FIG. 5A is configured to collect high-resolution 12.1 Mpixels color WL and AF images (or videos) in real time (<1 s), which are displayed in red-green-blue (RGB) format on a 3.5-in. touch-sensitive color liquid-crystal display (LCD) screen of the device. The device includes broadband white light-emitting diodes (LEDs), electrically powered by a standard AC125V source, configured to provide illumination during WL imaging. The two arrays 180, 187 may be monochromatic violet-blue ($\lambda_{exc}$=405_20 nm) LED arrays (Model LZ4, LedEngin, San Jose, Calif.) to provide 4-W excitation light power during FL imaging (bright, uniform illumination area ~700 cm2 at 10 cm distance from skin surface). The WL and FL images are detected by a high-sensitivity CCD sensor mounted with a dual band FL filter ($\lambda_{emiss}$=500 to 550 and 590 to 690 nm) (Chroma Technologies Corp., Vermont) in front of the camera lens to block excitation light reflected from the skin surface. The FL emission filter 190 is configured to spectrally separate tissue and bacteria AF. The device is configured to display the spectrally separated tissue and bacterial AF as a composite RGB image without image processing or color-correction, thus allowing the user to see the bacteria distribution within the anatomical context of the wound and body site. The CCD image sensor is sensitive across ultraviolet (<400 nm), visible (400 to 700 nm), and near-infrared (700 to 900 nm) wavelengths to AF of tissues and bacteria, in the absence of exogenous contrast agents.

FIG. 5B shows another exemplary embodiment of the device in use with an endoscope 42. Endoscope 42 may be flexible or rigid. As shown in FIG. 5B, endoscope 42 may be attached to the device to obtain FL and/or white light images of anatomically-constrained locations (e.g., hard to reach locations located in the head and neck), such as within body lumens of a patient. The device, when used with endoscope 42, may include multiple excitation LED arrays configured, for example, for sequenced 405 nm, 532 nm, etc, illumination for multiplexed read out of the microarray bioassay. Endoscope 42 may also provide 3D stereoscopic fluorescence imaging that may provide, for example, topography-specific information about bacterial infection of curved surfaces.

Figure 6A:
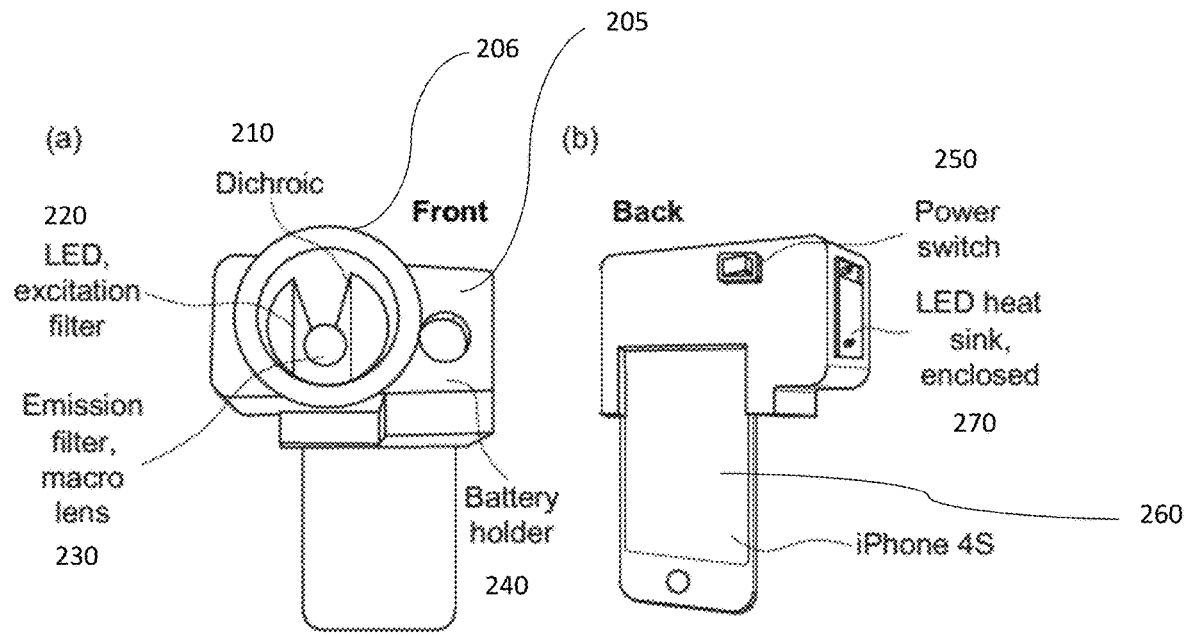
FIGS. 6A-6D show alternative exemplary embodiments of a handheld device for obtaining data regarding a target, the handheld device incorporating an iPhone.

In another exemplary embodiment, the image acquisition device is a handheld device that is incorporated with a mobile device to take both white light images and fluorescent images. It is also contemplated that in some embodiments, the handheld device takes only white light images or only fluorescent images when incorporated with the mobile device. The mobile device may be a mobile communication device, such as a smartphone, mobile phone, iPod, iPhone, or other such device having existing image-capturing capabilities such as the CCD sensor. Although described herein with regard to usage with the iPod touch or iPhone, it should be understood that other platforms (e.g., Android, etc.) may be used. For example, as shown in FIG. 6A, the device incorporates an iPhone 4S. The handheld device may also have one or more downloadable applications, enabling the user to take the white light and/or fluorescent images. Those of ordinary skill in the art will understand that the mobile communication devices described and illustrated herein are exemplary only, and that various other types and/or configurations of image acquisition devices, handheld devices, and/or mobile communication devices are contemplated without departing from the scope of the present disclosure and claims.

A mobile imaging device adaptor 200 is shown in FIG. 6A. The adaptor 200 is a handheld imaging adaptor for a mobile device that provides point-of-care, real-time wound care assessment and management. The adaptor 200, when used with the mobile device, is a non-invasive device that allows clinicians and nurses to collect white light and/or fluorescence digital images. In some embodiments, the adaptor 200 is configured to collect both white light and fluorescent images. Thus, the adaptor 200 may include a toggle switch to switch between the white light and fluorescent imaging modes. In other embodiments, the adaptor 200 is configured to collect fluorescent images and white light images are captured by the mobile device when the adaptor is removed from the mobile device.

FIG. 6A shows an embodiment in the which the adaptor 200 is configured for fluorescence imaging and is coupled to a mobile device. When in the fluorescence imaging mode, the mobile device and adaptor 200 detect the presence of clinically relevant bacteria in, for example, a wound bed, wound periphery, and off-site area while also enabling visualization of connective tissue to provide important anatomical context to the user with respect to the location of the bacteria. In this manner, contrast agents are not required when using the mobile device and adaptor.

Inset (a) of FIG. 6A shows a front view of the device, showing the optical components and battery holder of the accessory adaptor, which is mounted onto a standard iPhone 4S smart phone. As shown in inset (a), the front side of the adaptor 200 includes a dichroic mirror 210, an LED excitation filter 220, an emission filter and macro lens 230, and a battery holder 240. Inset (b) of FIG. 6A shows a back view of the device, showing the on/off power switch 250 and the LCD display screen 260 on the mobile device, on which the WL and FL images are viewed by the user. Additionally, the adaptor 200 may include an LED heat sink 270.

White light imaging allows the user to capture an image of a patient wound, and the fluorescence imaging allows the user to capture a corresponding image highlighting the presence of bacteria on the image. Both white light images and fluorescence images are viewed on the display screen 260 of the mobile device. Thus, the display screen 260 may be coupled to a camera on the mobile device. The display screen 260 may range between about 4-inches (diagonal) and about 7-inches (diagonal) widescreen display with Multi-Touch IPS technology. Other size displays may be used based on user needs. In one example, the display quality settings are 1136×640-pixel resolution at 326 pixels per inch; 800:1 contrast ratio; and 500 cd/m2 max brightness. The display may have a fingerprint-resistant oleophobic coating. The resolution of the camera may be about 5 Megapixels and may have resolutions higher than 5 Megapixels, such as up to about 24 Megapixels, depending upon availability, amount of storage available, etc. The selection of the lens design allows the production of high-quality images, specifically in the red and green spectra. In one exemplary embodiment, a five-element lens is used (as iPod touch design). The user can tap to focus video and/or still images. The camera has optimal performance in the dark. The camera has an LED flash and shutter speeds are high.

Figure 6B:
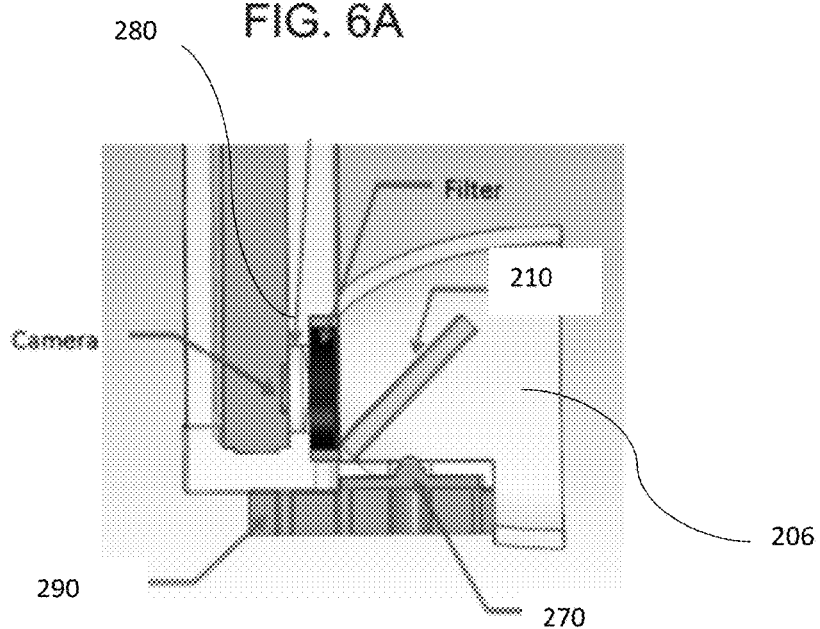

As shown in FIGS. 6A and 6B, the exemplary embodiment of the handheld device integrates a consumer grade mobile phone camera with a custom optical platform. The image acquisition occurs on the mobile phone camera and functions independently of the device housing, electronics and optics. The images are displayed on the phone's LCD touch screen and are stored on the phone itself. The customized optical design includes one violet 405 nm LED 270 positioned at a 45-degree angle to the dichroic mirror 210, which is fixed in front of the camera sensor. The dichroic mirror 210 reflects violet light while transmitting all greater wavelengths to produce fluorescence excitation illumination that is coaxial to the camera sensor. A macro lens 280 is situated in front of the camera sensor to allow for focused close-up imaging of wounds (<10 cm). A specific combination of excitation and emission filters are used to capture the red and green fluorescence data that is indicative of bacteria and connective tissues respectively. Emission filters may be used to block excitation light from a camera sensor of the phone. The adaptor may include a 9V battery to power the violet LED 270, which is triggered by the user through an external power switch. A heat sink 290 is attached to the back of the device for the LED printed circuit board with thermal paste to effectively transfer and dissipate the heat generated by the 5 W violet LED 270.

The adaptor includes a fluorescent light source as discussed above. The fluorescent light source may be a violet light source that may emit excitation light in the range of about 400 nm-about 450 nm. It is also contemplated that the fluorescent light source emits excitation light in the range of about 450 nm-about 500 nm, about 500 nm-about 550 nm, about 600 nm-about 650 nm, about 650 nm-about 700 nm, about 700 nm-about 750 nm, and combinations thereof.

In accordance with this exemplary embodiment, the housing 205 of the adaptor 200 may be made by 3D printing. Other types of suitable structures are disclosed herein, and variations thereof will be understood by those of ordinary skill in the art based on the present teachings. The housing 205 provides a means for aligning the optical components with a consumer grade camera and encasing both the electrical components used to drive the LED and the thermal solution while creating a user friendly and lightweight handheld design. As shown in FIGS. 6A and 6B, the housing 205 may include an extension portion 206 that extends outwardly from a patient-facing side of the adaptor. The dichroic mirror 210, the LED excitation filter 220, and the emission filter and macro lens 230 may be disposed within the extension portion 206. Furthermore, the extension portion 206 may be aligned with the camera (optical sensor) of the mobile device so that the fluorescent emissions of the target illuminated by the fluorescent excitation light are directed to the camera (optical sensor). Further, as shown in FIG. 6B, the use of the dichroic mirror 210 allows the fluorescent light source positioned below the camera (optical sensor) to be directed out of the extension 206 toward the target being imaged. The filter in front of the camera blocks the reflected excitation light while allowing other wavelengths of light to pass through to the camera. For example, the emission filter may be a dual band high transmission bandpass filter that is configured to pass emissions having wavelengths corresponding to the dual bands of the filter.

Figure 6C:
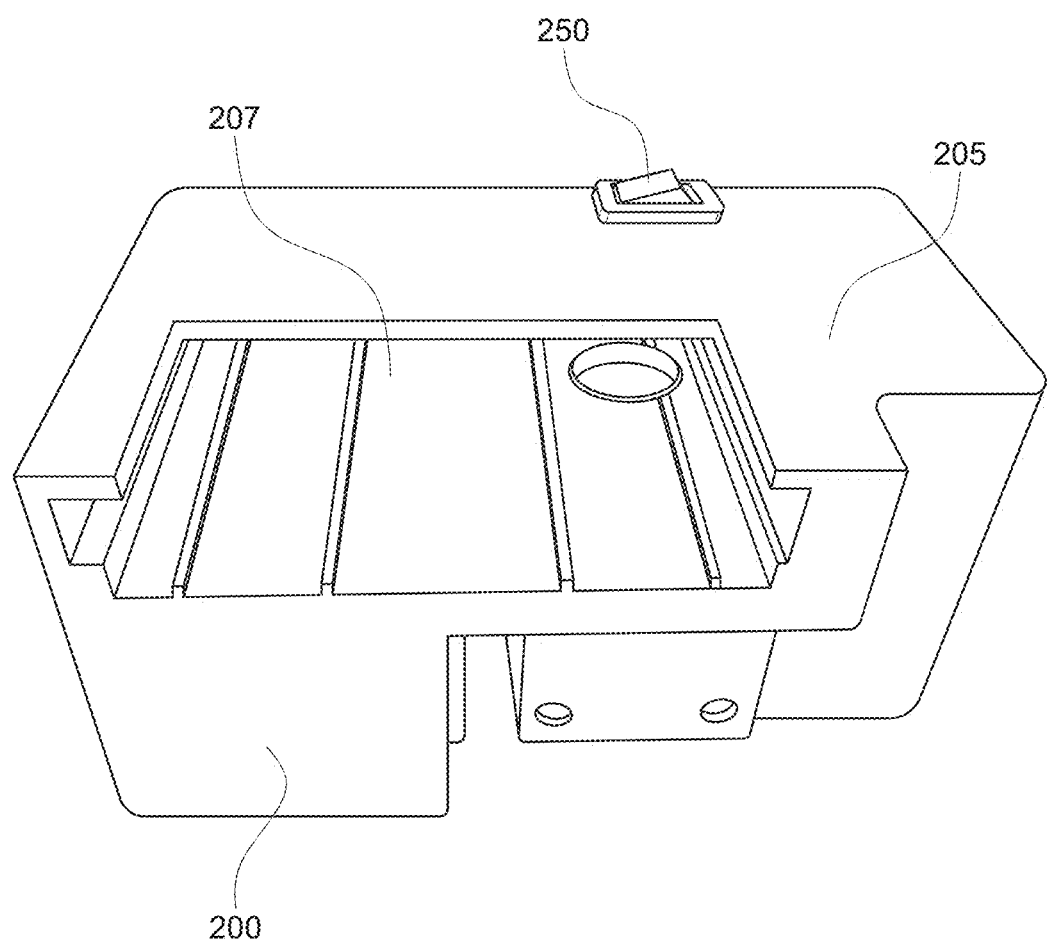

FIG. 6C shows a rear, perspective view of the adaptor 200 without the mobile device. As shown in FIG. 6C, the adaptor 200 includes an opening 207 so that the adaptor 200 is designed to slide onto the top of the mobile device, for example the iPhone 4s, and fit snuggly around the mobile device to remain fixed in place during imaging. The adaptor 200 is removable from the mobile device. Thus, in some embodiments, the adaptor 200 may be removed from the mobile device for white light imaging, in which the flash of the camera of the mobile device is used as the white light source for white light imaging. In accordance with another exemplary embodiment, the adaptor 200 may be permanently affixed to the mobile device, such as the iPhone 4s. In such an embodiment, a movable filter may be provided for switching between white light imaging and fluorescent imaging, in a manner similar to that described with regard to embodiments of the handheld device discussed in FIGS. 1 and 2. Thus, in this embodiment, a toggle switch may be provided to switch between the white light and fluorescent imaging.

As shown in FIG. 6C, the opening 207 of the adaptor 200 may be sized and configured to receive a mobile device such as a cellular phone. The opening may be sized for a specific mobile device, for example for the iPhone 4s. Thus, a top portion of the mobile device, including the camera on the mobile device, is slid into the opening 207 on the adaptor 200 to align the camera of the mobile device with the filters and the dichroic mirror 210 on the adaptor 200, as shown in FIG. 6B. The adaptor 200 in the embodiment of FIG. 6C also includes a switch 250 to turn on/off the LED excitation light. The switch 250 may also be used to switch between a white light imaging and a fluorescent imaging mode, as discussed above.

Figure 6D:
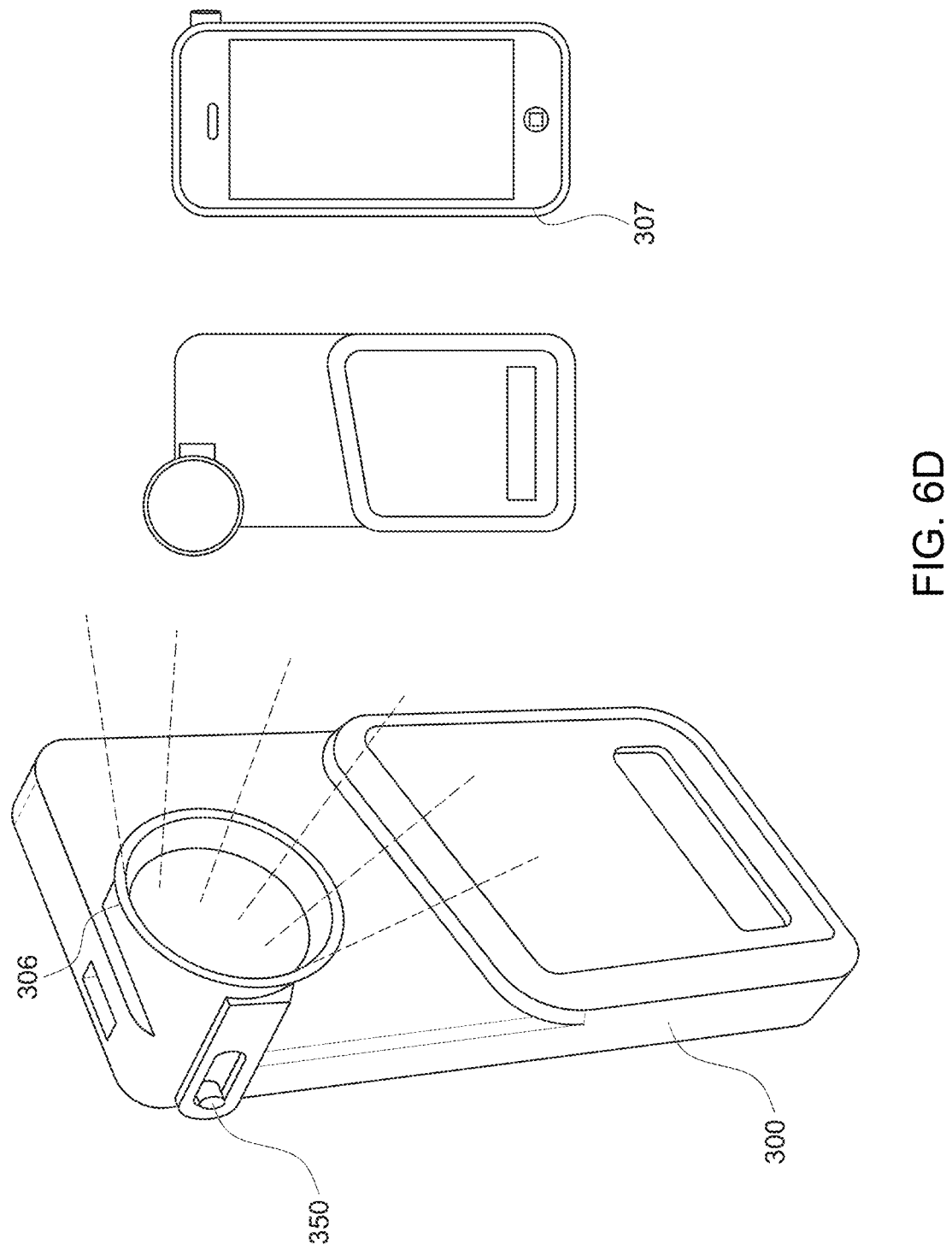

FIG. 6D shows another exemplary embodiment of an adaptor 300 for use with a mobile device, such as, for example, the iPhone 4s. As shown in FIG. 6D, the adaptor 300 includes an opening 307 that is sized to receive the entire mobile device. In this embodiment, the back and side portions of the mobile device are disposed in the opening 307 of the adaptor. An extension portion 306 is positioned over the camera (optical sensor) of the mobile device in order to align the camera (optical sensor) of the phone with the filter(s), to allow fluorescence excitation light produced by the fluorescent LED to be directed toward an imaging target, and to allow the camera sensor to receive the resultant fluorescence emissions. The embodiment of FIG. 6D also includes a toggle switch 350, to turn on/off the LED excitation light, as discussed above.

To perform fluorescence imaging using the adaptor 200, 300, the user switches on the violet LED using the toggle switch on the back of the device (FIGS. 6A, 6C, 6D). As the switch is moved to the 'on' position, the 9V battery sends power to the LED to drive the violet LED. The violet broad band LED, which is situated perpendicularly to the iPhone camera sensor and 45 degrees to the dichroic mirror, emits 405 nm light at the dichroic mirror. The dichroic mirror reflects almost 100% of the light at the 405 nm wavelength directly onto the target. The tissues and bacteria in the target absorb the 405 nm photons from the violet LED, and photons of a longer wavelength are then emitted by the bacteria and tissue to create fluorescence. The specific emission filter that is positioned in front of the mobile device's camera sensor controls the wavelengths of photons that are able to reach the camera sensor and effectively blocks the excitation light. The mobile device's camera sensor captures an RGB image of the emitted photons where bacteria is displayed as red (e.g. *S. aureus*) or very bright bluish-green (e.g. *Pseudomonas aruginosa*) and healthy connective tissues from skin or wounds are captured by a green fluorescence signal. The user may then use the fluorescence image (or video) stored on the mobile device to determine where bacteria are located within and around a wound.

Those of ordinary skill in the art will understand that the adaptors described and illustrated herein are exemplary only, and that various other types and/or configurations of adaptors are contemplated without departing from the scope of the present disclosure and claims.

EXAMPLES

The studies discussed herein aimed to determine the ability of the handheld device to accurately detect and measure bacterial wounds in real time, guide treatment decisions, and track wound healing over the course of antibacterial treatment.

In one example, a study using the handheld device described herein tracked patient wounds over time. The study was broken into two parts, the first part to establish the safety and feasibility of AF imaging to improve wound sampling by accurately detecting clinically-significant levels of pathogenic bacteria in chronic wound patients, compared to standard wound assessment (including swab-based methods). The second part to demonstrate the feasibility of AF image guidance for wound treatment and quantitative treatment response, compared to standard wound assessment (including swab-based methods). Swab cultures were used to compare AF imagining with WL examination, to determine sensitivity, specificity, and predictive values for FL imaging for detecting clinically-significant bacterial loads.

In the first part of the study, high resolution WL and FL images were taken of every patient's wound at each visit. A disposable length calibration scale (sticker) was placed near the wound during WL and FL imaging to track each patient's ID and date of the imaging. Regular room lighting was used during WL imaging, and the lights were turned off during FL imaging to eliminate any artifacts in the images. To preserve bacterial characteristics on the tissue, no swabs were taken of the wound until completion of both the WL and FL imaging. The process to capture a WL image took 1-2 min per wound, and subsequent FL imaging took 1-2 min per wound. The clinician also swabbed each suspicious marked area on the patient using the Levine sampling method, and swabs were sent for blinded microbiology testing (it is noted that the Levine sampling method is the most commonly used swabbing method and involves only sampling the center of the wound). Patients were treated and discharged according to standard protocols.

The location(s) of red and/or green AF were marked on printed images, as discussed further below. FL spectroscopy was used in some cases to characterize AF areas in/around the wound. Spectra were compared on a location basis with microbiology results. A complete data file for each patient's visit (CSS, WL and FL images, spectroscopy and microbiology) were stored in an electronic database according to Good Clinical Practice guidelines.

In the second part of the study, three sequential 2-month arms were used: non-guided treatment (control), FL guided treatment and non-guided treatment (control). In the first 2-month phase, wounds were assessed weekly by CSS and then treated at the discretion of the clinical team using best practice methods (ultrasonic and/or scalpel wound debridement, topical/systemic antibiotics, saline wash, dry or antimicrobial dressings or iodine). Corresponding WL and FL images were taken of each wound pre- and post-treatment as described previously. 2-month evaluation periods were selected based on established clinical data for venous leg ulcers showing that this is sufficient to detect a reliable and meaningful change in wound area, as a predictive indicator of healing. Wound swabs were collected by FL guidance. Clinicians were blinded to FL images during this first (control) phase. During the subsequent 2-month phase, wound assessment was performed normally but clinicians were shown FL images of the wound during treatment.

During the final 2-month phase, WL and FL imaging were performed and swabs were collected, with clinician blinding to the FL results during treatment delivery. Importantly, while the clinicians understood and could remember the meaning and characteristics of the red and green fluorescence signals, respectively, blinding them during treatment delivery in the control periods was possible because the fluorescence results for each wound examination and each patient were different. Thus, in the absence of real-time fluorescence guidance during wound treatment, previous knowledge of fluorescence characteristics did not substantively influence the treatment decisions during the control periods. WL and FL images were also taken after each treatment to analyze wound area.

Four blinded, trained clinical and/or research staff members independently measured the average wound size on WL images using digital tracing (MATLAB v.7.9.0, The Math-Works, Massachusetts, USA). The observers measured the wounds in separate sessions with a minimum of 7 days between sessions to minimize memory effect. An adhesive scale bar placed adjacent to the wound during imaging provided accurate length calibration within +0.5 mm. Room lights remained on during WL imaging, but were turned off during FL imaging. WL and FL images were collected with the handheld device held/positioned 10-15 cm from the wound. All imaging parameters (distance, exposure time, ISO setting, white balance, etc.) were kept constant between visits. For distances less than 5 cm from a wound (small diameter wounds), the camera's built-in macro mode was used. Automatic focusing allowed rapid (~1s) image acquisition. Images (or video) were captured in real-time and stored on the camera's memory card. Switching between WL and FL modes was substantially instantaneous using a built in "toggle switch." Devices were decontaminated between uses with 70% ethyl alcohol.

WL and AF images were transferred to a laptop. Regions of interest (ROIs) were identified from individual 1024×1024 pixel FL images of each wound at each clinic visit. RGB images were separated into individual channels. The green and red channels of the RGB image were representative of the true tissue and bacterial AF signals detected in vivo. To quantify bacterial levels from individual FL images, the following image processing procedures were used. Briefly, individual green and red image channels from each RGB image were converted to greyscale (the blue channel was not used) and pixels whose greyscale intensity was above a given histogram threshold (selected to reduce the background noise of the raw image) were counted. A red color mask for red FL bacteria was created by finding the local maxima in the color range 100-255 greyscale. Then, an inverted green color mask was used to remove the green FL. All pixels with red FL (above the histogram threshold) were binarized and the sum of all "1" pixels was calculated. This was repeated for the green channel of each image. These data gave an estimate of the amount of red (or green) bacteria in each image. The number of FL pixels was converted into a more useful pixel area measure (cm2) using the adhesive length calibration stickers, thereby providing the total amount of fluorescent bacteria as an area measurement. The Levine method was used to aseptically swab wounds for confirmation of bacterial presence, species typing, Gram signing, antibiograms, and semi-quantitative bacterial load.

Tissue AF produced by endogenous collagen or elastin in the skin appeared as green FL, and clinically-relevant bacterial colonies (e.g. *Staphylococcus aureus*) appeared as red FL (caused by endogenous porphyrins). Some bacteria (e.g. *Pseudomonus aeruginosa*) produced a blue-green signal, due to siderophores/pyoverdins, which was differentiated spectrally and texturally from dermis AF using image analysis software. WL and FL images were collected in less than 1 second by the high-sensitivity CCD sensor mounted with a dual band FL filter ($\lambda_{emiss}$=500-550 and 590-690 nm) (Chroma Technologies Corp, VT, USA). The CCD image sensor was sensitive across a broad wavelength range of –300-800 nm. The handheld device integrated easily into the routine clinical work flow. By combining tissue FL with bacterial FL in a single composite image, the clinician instantly visualized the distribution and extent of the bacterial load within the anatomical context of the wound and body site. Typically, FL imaging added approximately 1-3 minutes/patient to the wound assessment routine, depending on the number of wounds and the duration of FL-guided swabbing.

The variation in measurements of wound areas between images taken under WL and FL were compared. The correlation between change in average wound area and FL image-guided treatment using Pearson correlation coefficients was also calculated. Assessing changes in wound area between the first control, the second FL image-guided, and the third control periods were performed using a linear mixed effect model.

The accuracy of identifying clinically-significant bacterial load for AF image-guided was compared with swabbing techniques and WL imaging. A total of 490 swabs were collected, of which 36.9% were taken from wound beds, 30.2% from wound peripheries, and 32.9% from "off-site" areas. It was determined that the AF accurately determined 74.5% of wounds with clinically-significant bioburden, and that WL imaging only detected 52.5% of the wounds. The handheld device accurately determined clinically-significant bioburden 82.4% of the time in the wound periphery and 67.1% in other areas. WL examination was correct only 17.6% of the time in peripheries and 32.9% in other areas. The overall accuracy of judging the presence of clinically-significant bacterial in chronic wounds for AF was 74.5% versus 35.5% for traditional methods of WL and swab results.

AF imaging detected clinically significant bacterial load in 85% of wound peripheries missed by conventional methods. Thus, the Levine method for swabbing only the wound bed may be insufficient, possibly resulting in antibacterial treatment being inappropriately withheld. However, modifying standard sampling practices to include swabbing of the wound periphery of all wounds would be impractical and costly. AF imaging could help clinicians decide if and where wound margins require sampling. The handheld imaging device also identified clinically significant bioburden in surrounding locations close to wounds, which represent sites of potential re-infection, where traditional methods do not examine or swab.

Identifying and quantitating wound bacterial burden is an important determinant of infection and healing. Data on the visualization and quantitative tracking of bacterial load led to the identification of a new, simple method for image-guided debridement and topical application of antibiotic and antiseptic, which minimizes unnecessary trauma to the wound boundary and maximizes the contribution of debridement to reducing bacterial burden. Every wound has the potential for infection, but distinguishing true infection from critical colonization by best practice methods remains challenging and arbitrary, and can lead to over- and under-treatment.

The handheld imaging device identifies pathogenic microbes and differentiates between at least the two major pathogenic species (*P. aeruginosa* and *S. aureus*), and informs medical treatment decisions. The device also offers a quantitative and reproducible way to monitor the effectiveness of existing and emerging wound care treatments. Furthermore, the handheld imaging device can be used to diagnose critically colonized wounds.

Multiple variables including host response, local and systemic factors, malperfusion, immunosuppression, diabetes, and medications affect the risk of infection. Critically colonized wounds can be difficult to diagnose because they do not always display classical signs of infection or clearly elevated levels of bioburden. Indeed, the clinical relevance of differentiating critically colonized wounds from infected wounds remains controversial. Identifying a high bacterial load in asymptomatic patients before infection occurs using AF imaging may help prevent infections by prompting aggressive treatment. If a bacterial infection is suspected, antibiotic selection could be guided by the established clinical principles and by AF identification of heavy bacterial burden and differentiation between Gram negative *P. aeruginosa* and Gram positive *S. aureus*.

In another exemplary embodiment, image analysis may be carried out on the handheld device or WL and FL images may be transferred to a laptop for image processing. Image analysis and processing of image data may be performed using a processor of the handheld device, and the results of such analyses may be displayed on the display of the handheld device.

Figure 7A:
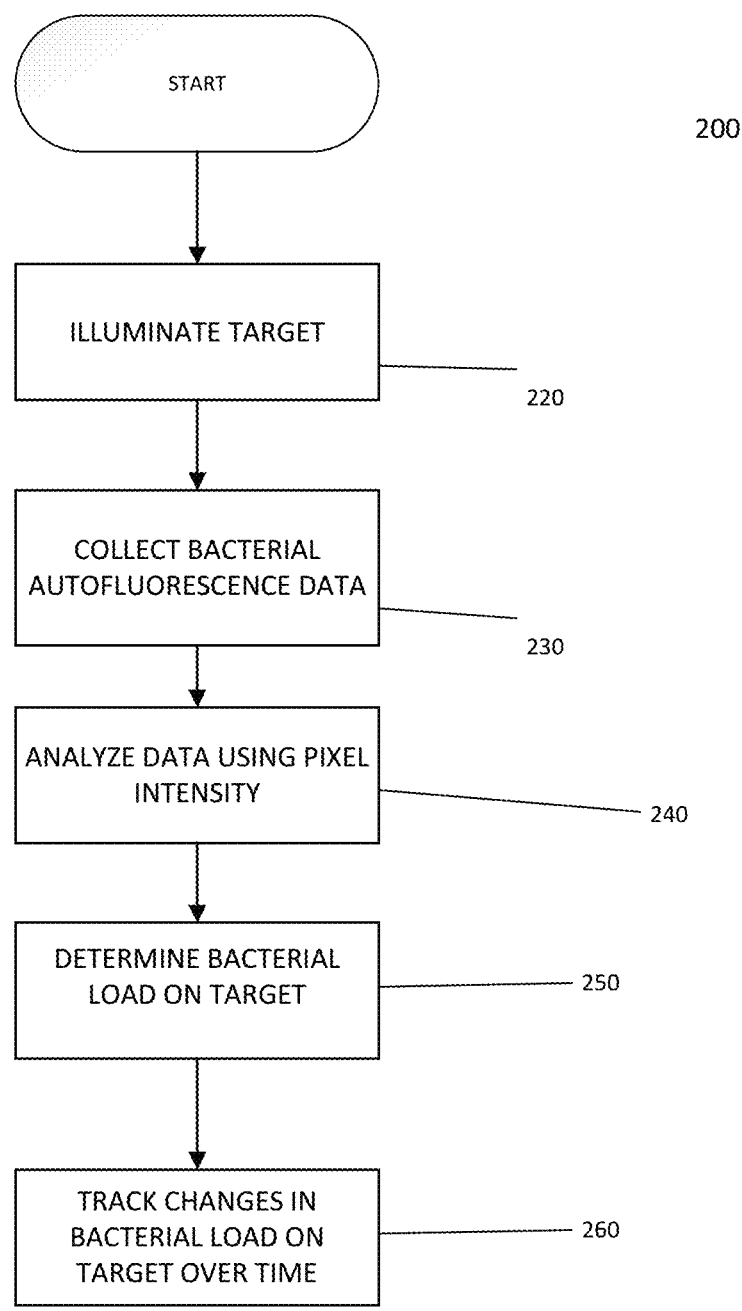
FIGS. 7A and 7B illustrate exemplary methods of determining bacterial load of a target in accordance with the present disclosure.
Figure 7B:
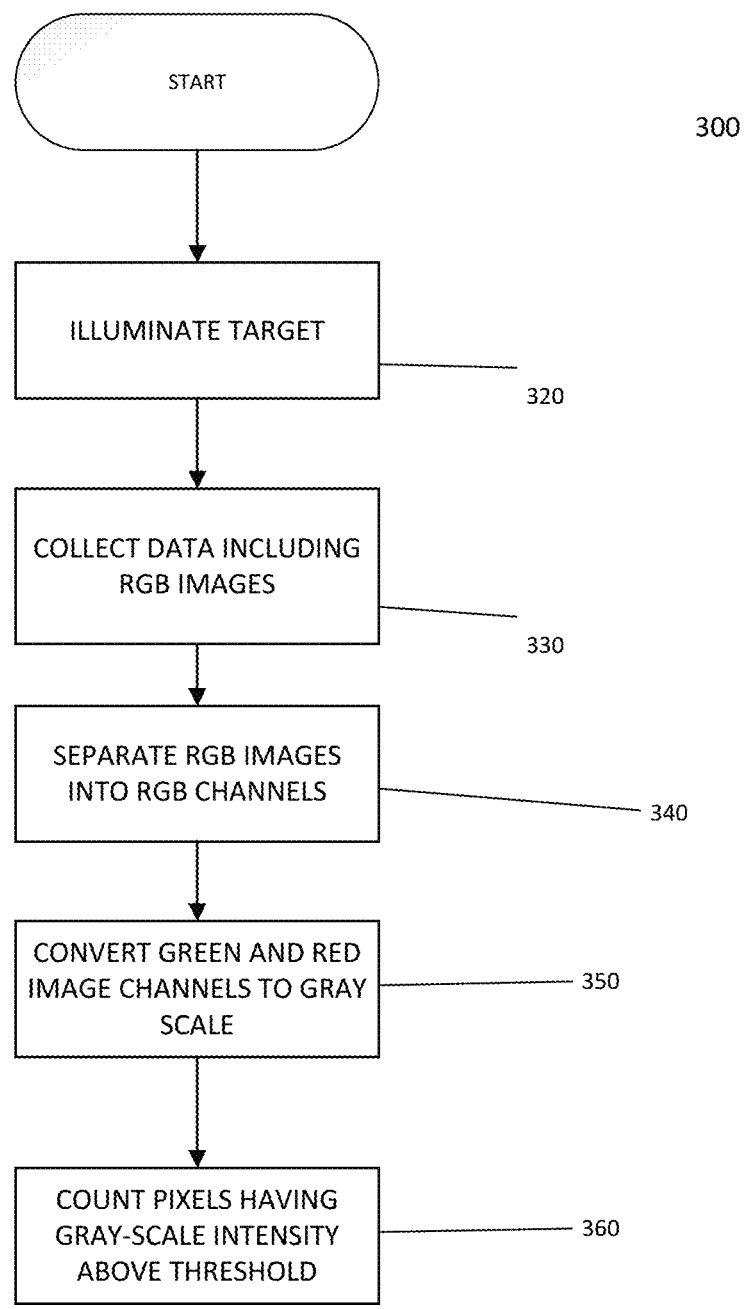

The following two exemplary programs may be used for image processing (for example, analysis of the data collected by the exemplary device using the Super HAD™ charge-coupled device (CCD) sensor-based camera (Model DSC-T900)) and portions of these processes are illustrated in FIGS. 7A and 7B: MATLAB software (Version 7.9.0, The MathWorks, Massachusetts) using a custom-written program and ImageJ Software (Version 1.45n). In the MATLAB program, regions of interests (ROIs) are identified from individual 1024×1024 pixel FL images of each wound. RGB images are separated into individual channels. Green (500 to 550 nm emission) and red AF (>590 nm) from tissue components and bacteria, respectively, detected by the CCD sensor are naturally aligned spectrally with the red and green filters on the Sony CCD image sensor. Thus, the green and red channels of the RGB image displayed on the handheld device's LCD screen are representative of the true tissue and bacterial AF signals detected in vivo. To quantify bacterial levels from individual FL images, the following image processing procedures may be used. Briefly, individual green and red image channels from each RGB image are converted to gray scale (the blue channel is not used) and pixels whose gray scale intensity is above a given histogram threshold (selected to reduce the background noise of the raw image) are counted. In certain embodiments, it is possible the blue channel would be used, for example, when imaging the amount of 405 nm excitation light that is absorbed by tissues/blood when imaging tissue vascularity/perfusion.

A red color mask for red FL bacteria is created by finding the local maxima in the color range 100 to 255 gray scale. Then, an inverted green color mask is used to remove the green FL. All pixels with red FL (above the histogram threshold) are binarized and the sum of all "1" pixels is calculated. This is repeated for the green channel of each image. These data give an estimate of the amount of red bacteria in each image. The number of FL pixels is converted into a more useful pixel area measure (cm2) by applying a ruler on the pixel image, thereby providing the total amount of fluorescent bacteria as an area measurement (cm2). The sizes of the wounds may be traced and measured similarly by converting pixel areas to cm2 of the circled wound area on the WL images. The resolution of the FL images is sufficient to localize bacteria based on regions of FL. ImageJ software may be used to separate FL images into red, green, and blue channels using the built-in batch processing function "Split Channels" located within the image menu and color submenu of the camera. Each resulting channel is displayed and saved in gray scale. For further analysis, an ROI may be identified in each corresponding red, green, and blue channel image. Under the built-in analysis menu, the "Set Measurement" function may be used to select and measure the following measurement parameters for each color channel image: pixel area, min. and max. gray scale intensity values, and mean gray intensity values. The average red channel intensity value may be determined as (bacterial) FL intensity per square pixel in each red channel image and then used for data analysis and comparison.

In one exemplary embodiment, a mouse skin wound model was used to correlate wound status with the progression of bacterial infection (n=5; 8 to 12 weeks; NCRNU-F). Correlation was based on data obtained using the exemplary handheld device described above, which incorporates the Super HAD™ charge-coupled device (CCD) sensor-based camera (Model DSC-T900. Daily WL and FL images were taken of the wounds as they became infected over time. Antibacterial treatment (topical Mupirocin three times daily, for a total of 1 day) was applied to the wound site when the red FL intensity peaked. The anti-microbial effect of the treatment was monitored over time using the handheld device to acquire daily WL and FL images of the wound after treatment. The wounds were monitored for a total of 10 days (see FIG. 8), after which the mice were sacrificed. Bacterial amounts from FL images and wound size from WL images were quantified using the MATLAB program described above and compared over time to determine the wound healing status.

Figure 8:
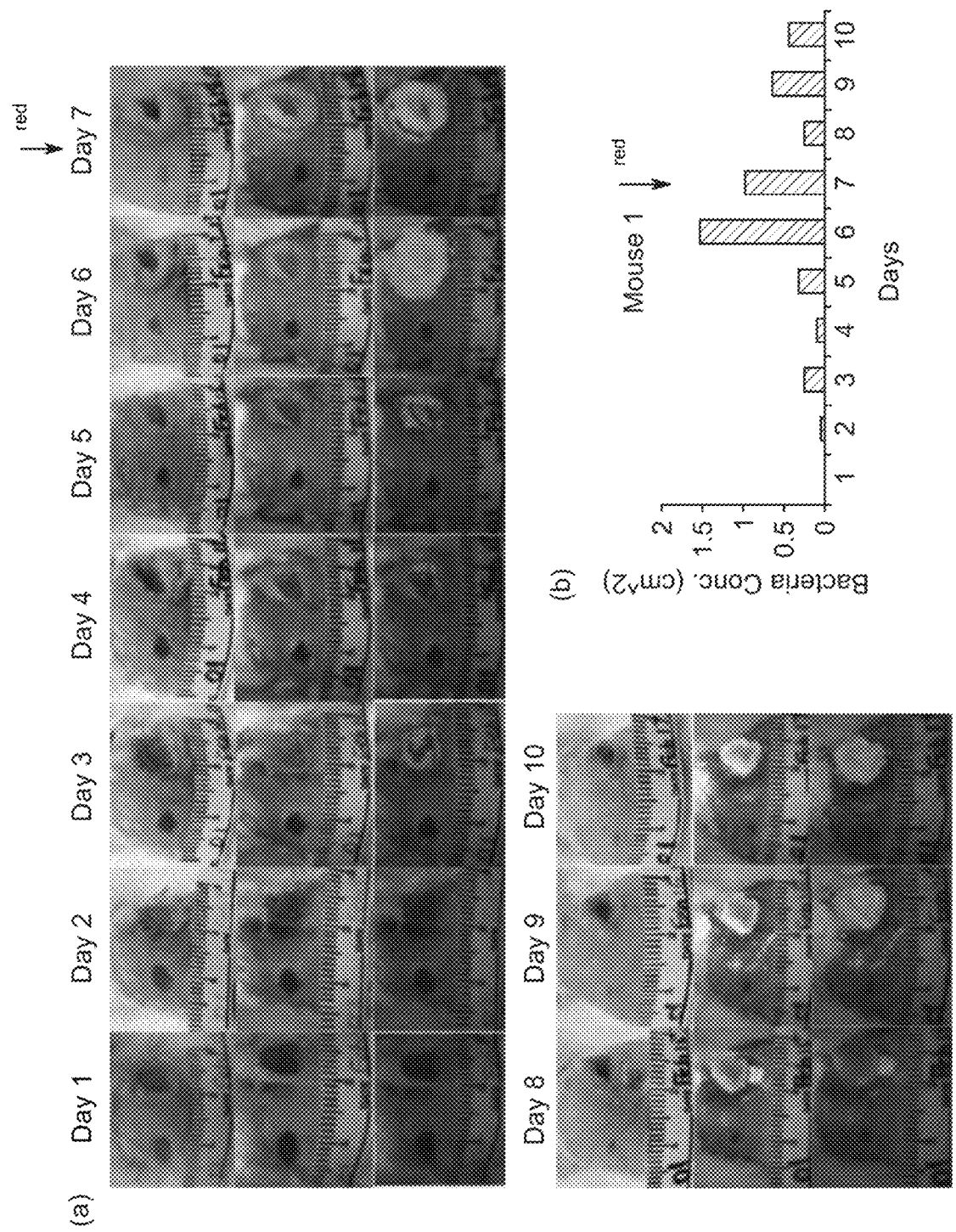
FIG. 8 shows representative white light (WL) and fluorescent (FL) images for a single mouse tracked over 10 days.

FIG. 8 shows representative WL and FL images for a single mouse tracked over 10 days. Inset (a) of FIG. 8 provides images taken with a handheld device in accordance with the present disclosure and showing the two equal-sized wounds on both sides of the spine. The right wound was inoculated with S. aureus in PBS and the left wound was inoculated with PBS only (control). The top row shows WL images, the middle row shows FL images, and the bottom row shows MATLAB quantified images, corresponding to bacterial areas and intensities. The FL imaging data demonstrated a significant increase in bacterial FL intensity in the wound inoculated with S. aureus, compared with the control wound, peaking on day 6. Mupirocin (day 7, red arrow) significantly decreased bacterial FL on day 8 to almost zero, indicating treatment effect. Bacteria increased again on days 9 and 10. Inset (b) of FIG. 8 provides a graph showing quantitative changes in bacterial load from FL images obtained in inset (a) of FIG. 8.

Figure 9:
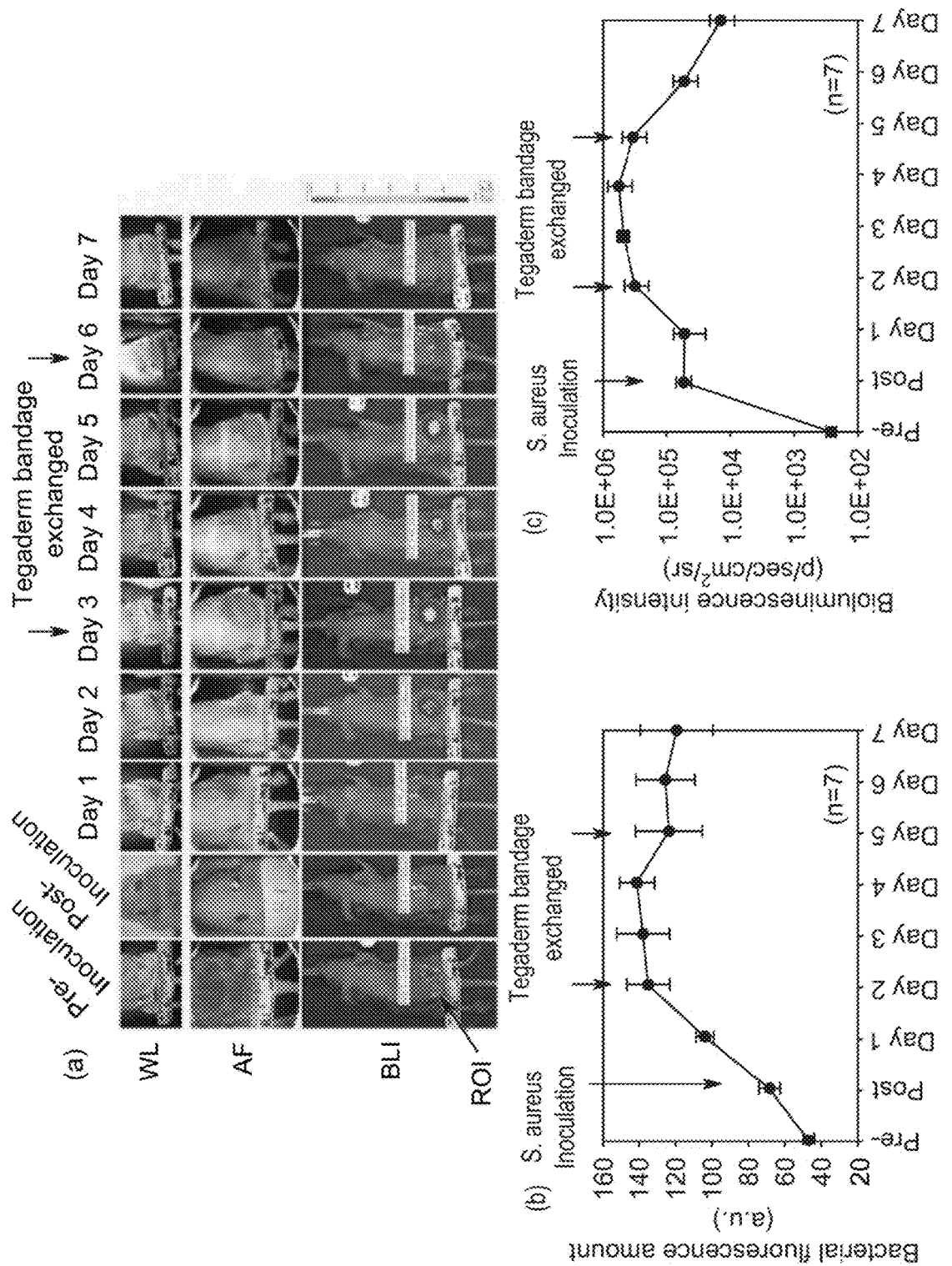
FIG. 9 illustrates preclinical data which show that pathogenic bacterial autofluorescence (AF) intensity correlates with bacterial load in vivo.

In accordance with another exemplary embodiment, BLI can be used to measure the absolute amount of bacteria in vivo, because it is one of the most sensitive and reliable screening tools for determining bacterial load. BLI collects the light emitted from the enzymatic reaction of luciferase and luciferin and therefore does not require excitation light. FL imaging using the handheld device (without any exogenous FL contrast agent administration) and BLI imaging of inoculated S. aureus bacteria were tracked over time and the FL and BLI intensities were compared (see FIG. 9) (n=7). The bacterial BLI signal did not contribute to the FL signal detected by the handheld device's consumer grade-CCD camera. Gram-positive bioluminescent S. aureus-Xen8.1 from the parental strain S. aureus 8325-4 (Caliper) was grown to mid-exponential phase the day before pathogen inoculation. Bacteria with the BLI cassette produce the luciferase enzyme and its substrate (luciferin), thereby emitting a 440 to 490 nm bioluminescent signal when metabolically active (FIG. 9). The bacteria (1010CFU) were suspended in 0.5 mL of PBS and injected into the wounds of female athymic nude mice (n=7; 8 to 12 weeks; NCRNU-F Homozygous). To detect S. aureus bioluminescence, BLI images of the wound were acquired before, immediately after, and 1, 2, 3, 4, 5, 6, and 7 days postinoculation inside the dark chamber of the Xenogen IVIS Spectrum Imaging System 100 (Caliper, Mass.), using an exposure time of 10 s. BLI images were captured using Living Image In Vivo Imaging software (Caliper, Mass.). ROIs were digitally circumscribed over the wound and the total luminescence intensity counts were measured within the ROIs for each time point imaged. The absolute amount of bacteria measured from the BLI signals was tested for correlation with the corresponding FL signals on the FL images taken over time of the same wound using the handheld device (as described above).

FIG. 9 provides preclinical data which show that pathogenic bacterial autofluorescence (AF) intensity correlates with bacterial load in vivo. Inset (a) of FIG. 9 shows a time course prototype device mobile images of skin wounds in a mouse prior to and after inoculation with bioluminescent S. aureus-Xen8.1 ($10^{10}$ CFU in 30 μL PBS). Representative WL (top row), AF (middle row), and bioluminescence (bottom row) images are shown for each time point to 7 days after inoculation in a wounded mouse. BLI imaging gives absolute bacterial amount in vivo. Red arrows show when the tegaderm bandage was exchanged, causing some bacteria to be removed from the surface. Inset (b) of FIG. 9 shows average red FL from S. aureus-Xen8.1 (n=7 nude mice) shown as a function of time demonstrating an increase in daily S. aureus bacterial FL (calculated from red channel of RGB images using ImageJ software). At days 2 and 7, tegaderm bandages were exchanged as per animal protocol. Average bacterial FL peaked at day 4 postinoculation. Inset (c) of FIG. 9 illustrates a corresponding time course bioluminescence data (calculated from ROI) show similar increase and peaking at day 4 in total bacterial load in the wound. Data indicates a strong positive correlation (Pearson correlation coefficient r=0.6889) between total bacterial AF in a wound and the bacterial load in vivo. Standard errors are shown. Scale bars: (a) WL 1.5 cm and AF, BLI 1 cm.

Imaging of Bacteriological Samples

Imaging devices in accordance with the present disclosure may be useful for imaging and/or monitoring in clinical microbiology laboratories. Such devices may be used for quantitative imaging of bacterial colonies and quantifying colony growth in common microbiology assays. Fluorescence imaging of bacterial colonies may be used to determine growth kinetics. Software may be used to provide automatic counting of bacterial colonies.

To demonstration the utility of such devices in a bacteriology/culture laboratory, live bacterial cultures were grown on sheep's blood agar plates. Bacterial species included Streptococcus pyogenes, Serratia marcescens, Staphylococcus aureus, Staphylococcus epidermidis, Escherichia coli, and Pseudomonas aeruginosa (American Type Culture Collection, ATCC). These were grown and maintained under standard incubation conditions at 37° C. and used for experimentation when during 'exponential growth phase'. Once colonies were detected in the plates (~24 h after inoculation), the device was used to image agar plates containing individual bacterial species in a darkened room. Using violet/blue (about 405 nm) excitation light, the device was used to image both combined green and red autofluorescence (about 490-550 nm and about 610-640 nm emission) and only red autofluorescence (about 635+/−10 nm, the peak emission wavelength for fluorescent endogenous porphyrins) of each agar plate. Fluorescence images were taken of each bacterial species over time for comparison and to monitor colony growth.

Figure 10:
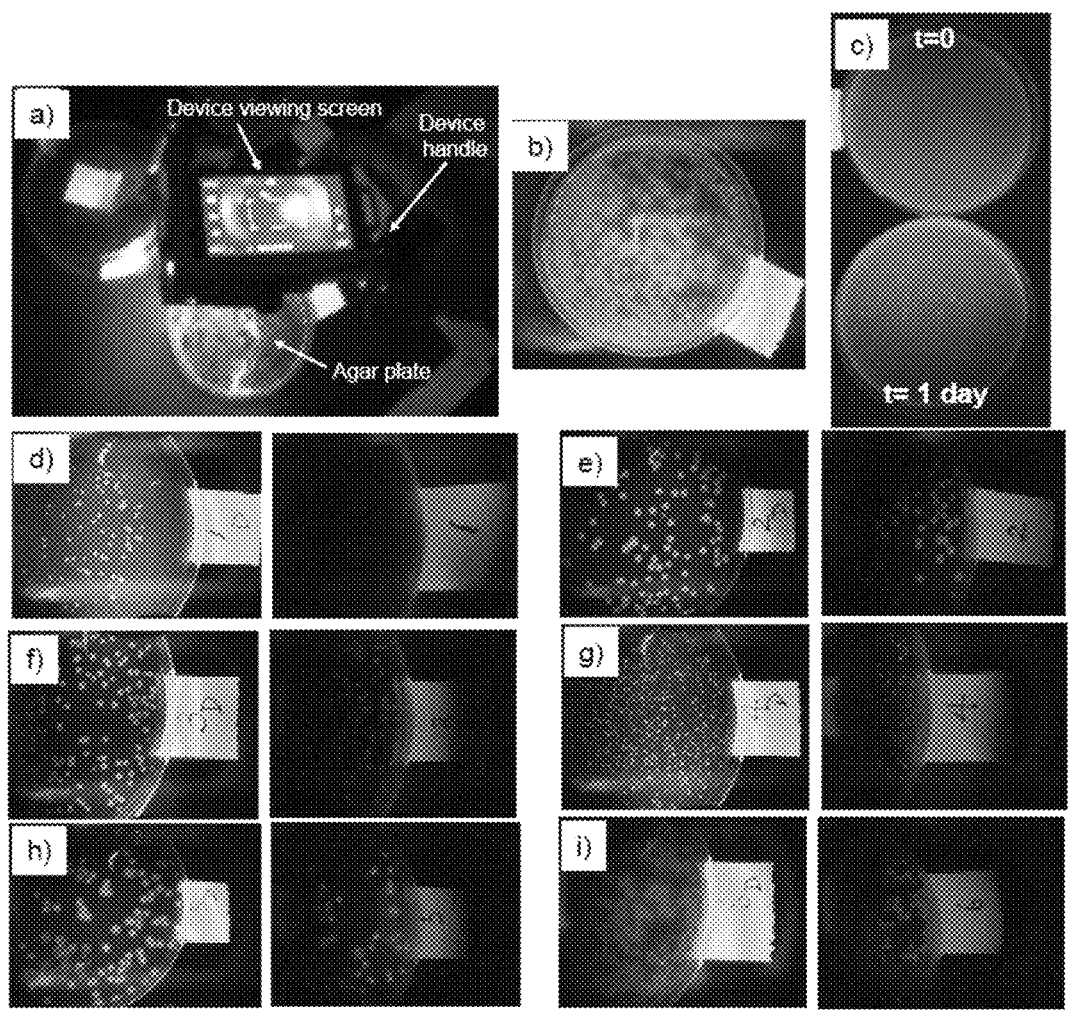
FIG. 10 shows images of live bacterial cultures captured using a device for fluorescence-based monitoring in accordance with the present disclosure.

Reference is now made to FIG. 10. Inset a) of FIG. 10 shows a device being used to image live bacterial cultures growing on sheep's blood agar plates to detect bacterial autofluorescence. Inset b) of FIG. 10 shows the image of autofluorescence emitted by Pseudomonas aruginosa. The device may also be used to detect, quantify and/or monitor bacterial colony growth over time using fluorescence, as demonstrated in inset c) of FIG. 10 with fluorescence imaging of the growth of autofluorescent Staphylococcus aureus on an agar plate 24 hours after innoculation. Note the presence of distinct single bacterial colonies in the lower image. Using violet/blue (e.g., 405 nm) excitation light, the device was used to detect both combined green and red (e.g., 490-550 nm+610-640 nm) and only red (e.g., 635+/−10 nm, the peak emission wavelength for fluorescent endogenous porphyrins) emission autofluorescence from several live bacterial species including Streptococcus pyogenes, shown in inset d) of FIG. 10; Serratia marcescens, shown in inset e) of FIG. 10; Staphylococcus aureus, shown in inset f) of FIG. 10; Staphylococcus epidermidis, shown in inset g) of FIG. 10; Escherichia coli, shown in inset h) of FIG. 10; and Pseudomonas aeruginosa, shown in inset i) of FIG. 10. Note that the autofluorescence images obtained by the device of the bacterial colonies may provide useful image contrast for simple longitudinal quantitative measurements of bacterial colonization and growth kinetics, as well as a means of potentially monitoring response to therapeutic intervention, with antibiotics, photodynamic therapy (PDT), low level light therapy, hyperbaric oxygen therapy (HOT), or advanced wound care products, as examples.

High spatial resolution of the camera detector combined with significant bacterial autofluorescence signal-to-noise imaging with the device allowed detection of very small (e.g., <1 mm diameter) colonies. The device provided a portable and sensitive means of imaging individual bacterial colonies growing in standard agar plates. This provided a means to quantify and monitor bacterial colony growth kinetics, as seen in inset c), as well as potentially monitoring response to therapeutic intervention, with antibiotics or photodynamic therapy (PDT) as examples, over time using fluorescence. Therefore, devices in accordance with the present disclosure may serve as a useful tool in the microbiology laboratory.

Figure 11:
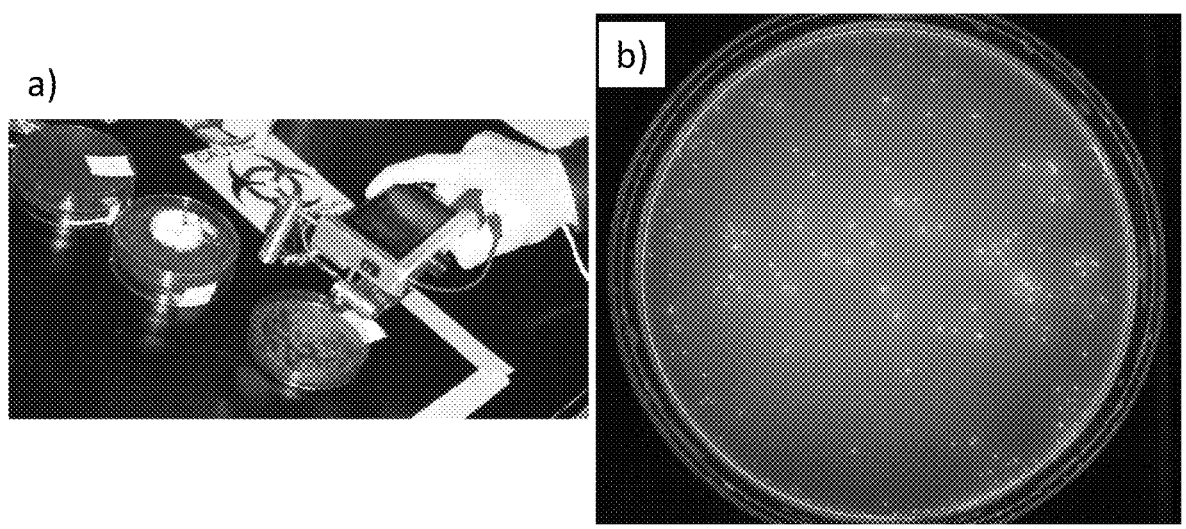
FIG. 11 shows an example of bacterial monitoring using a device for fluorescence-based monitoring in accordance with the present disclosure.

FIG. 11, inset a), shows an example of the use of an imaging device in standard bacteriology laboratory practice. In inset b) of FIG. 11, fluorescence imaging of a Petri dish containing Staphylococcus aureus combined with custom proprietary image analysis software allows bacterial colonies to be counted rapidly, and here the fluorescence image of the culture dish shows ~182 (+/−3) colonies (bright bluish-green spots) growing on agar at 37° C. (about 405 nm excitation, about 500-550 nm emission (green), about >600 nm emission (red)).

In addition to providing detecting of bacterial species, the device may be used for differentiating the presence and/or location of different bacterial species (e.g., Staphylococcus aureus or Pseudomonas aeguinosa), for example in wounds and surrounding tissues. This may be based on the different autofluorescence emission signatures of different bacterial species, including those within the 490-550 nm and 610-640 nm emission wavelength bands when excited by violet/blue light, such as light around 405 nm. Other combinations of wavelengths may be used to distinguish between other species on the images. This information may be used to select appropriate treatment, such as choice of antibiotic.

Such imaging of bacteriology samples may be applicable to monitoring of wound care.

Use in Monitoring of Wound Healing

Devices in accordance with the present disclosure may also be scanned above any wound (e.g., on the body surface) such that the excitation light may illuminate the wound area. The wound may then be inspected using the device such that the operator may view the wound in real-time, for example, via a viewer on the imaging device or via an external display device (e.g., heads-up display, a television display, a computer monitor, LCD projector or a head-mounted display). It may also be possible to transmit the images obtained from the device in real-time (e.g., via wireless communication) to a remote viewing site, for example for telemedicine purposes, or send the images directly to a printer or a computer memory storage. Imaging may be performed within the routine clinical assessment of patient with a wound.

Prior to imaging, fiduciary markers (e.g., using an indelible fluorescent ink pen) may be placed on the surface of the skin near the wound edges or perimeter. For example, four spots, each of a different fluorescent ink color from separate indelible fluorescent ink pens, which may be provided as a kit to the clinical operator, may be placed near the wound margin or boundary on the normal skin surface. These colors may be imaged by the device using the excitation light and a multispectral band filter that matches the emission wavelength of the four ink spots. Image analysis may then be performed, by co-registering the fiduciary markers for inter-image alignment. Thus, the user may not have to align the imaging device between different imaging sessions. This technique may facilitate longitudinal (i.e., over time) imaging of wounds, and the clinical operator may therefore be able to image a wound over time without the need for aligning the imaging device during every image acquisition.

In addition, to aid in intensity calibration of the fluorescence images, a disposable simple fluorescent standard 'strip' may be placed into the field of view during wound imaging (e.g., by using a mild adhesive that sticks the strip to the skin temporarily). The strip may be impregnated with one or several different fluorescent dyes of varying concentrations which may produce pre-determined and calibrated fluorescence intensities when illuminated by the excitation light source, which may have single (e.g., 405 nm) or multiple fluorescence emission wavelengths or wavelength bands for image intensity calibration. The disposable strip may also have the four spots as described above (e.g., each of different diameters or sizes and each of a different fluorescent ink color with a unique black dot placed next to it) from separate indelible fluorescent ink pens. With the strip placed near the wound margin or boundary on the normal skin surface, the device may be used to take white light and fluorescence images. The strip may offer a convenient way to take multiple images over time of a given wound and then align the images using image analysis. Also, the fluorescent 'intensity calibration' strip may also contain an added linear measuring apparatus, such as a ruler of fixed length to aid in spatial distance measurements of the wounds. Such a strip may be an example of a calibration target which may be used with the device to aid in calibration or measuring of image parameters (e.g., wound size, fluorescence intensity, etc.), and other similar calibration target may be used.

It may be desirable to increase the consistency of imaging results and to reproduce the distance between the device and the wound surface, since tissue fluorescence intensity may vary slightly if the distance changes during multiple imaging sessions. Therefore, in an embodiment, the device may have two light sources, such as low power laser beams, which may be used to triangulate individual beams onto the surface of the skin in order to determine a fixed or variable distance between the device and the wound surface. This may be done using a simply geometric arrangement between the laser light sources, and this may permit the clinical operator to easily visualize the laser targeting spots on the skin surface and adjust the distance of the device from the wound during multiple imaging sessions. Other methods of maintaining a constant distance may include the use of ultrasound, or the use of a physical measure, such as a ruler, or a range finder mechanism.

Use in White Light Imaging

Devices in accordance with the present disclosure may also be used to take white light images of the total wound with surrounding normal tissues using a measuring apparatus (e.g., a ruler) placed within the imaging field of view. This may allow visual assessment of the wound and calculation/determination of quantitative parameters such as the wound area, circumference, diameter, and topographic profile. Wound healing may be assessed by planimetric measurements of the wound area at multiple time points (e.g., at clinical visits) until wound healing. The time course of wound healing may be compared to the expected healing time calculated by the multiple time point measurements of wound radius reduction using the equation $R=\sqrt{A/\pi}$ (R, radius; A, planimetric wound area; $\pi$, constant 3.14). This quantitative information about the wound may be used to track and monitor changes in the wound appearance over time, in order to evaluate and determine the degree of wound healing caused by natural means or by any therapeutic intervention. This data may be stored electronically in the health record of the patient for future reference. White light imaging may be performed during the initial clinical assessment of the patient by the operator.

Use in Autofluorescence Imaging

Devices in accordance with the present disclosure may also be designed to detect all or a majority of tissue autofluorescence (AF). For example, using a multi-spectral band filter, the device may image tissue autofluorescence emanating from the following tissue biomolecules, as well as blood-associated optical absorption, for example under 405 nm excitation: collagen (Types I, II, III, IV, V and others) which appear green, elastin which appears greenish-yellow-orange, reduced nicotinamide adenine dinucleotide (NADH), flavin adenine dinucleotide (FAD), which emit a blue-green autofluorescence signal, and bacteria/microorganisms, most of which appear to have a broad (e.g., green and red) autofluorescence emission.

Image analysis may include calculating a ratio of red-to-green AF in the image. Intensity calculations may be obtained from regions of interest within the wound images. Pseudo-coloured images may be mapped onto the white light images of the wound.

Examples in Wound Healing

Figure 12:
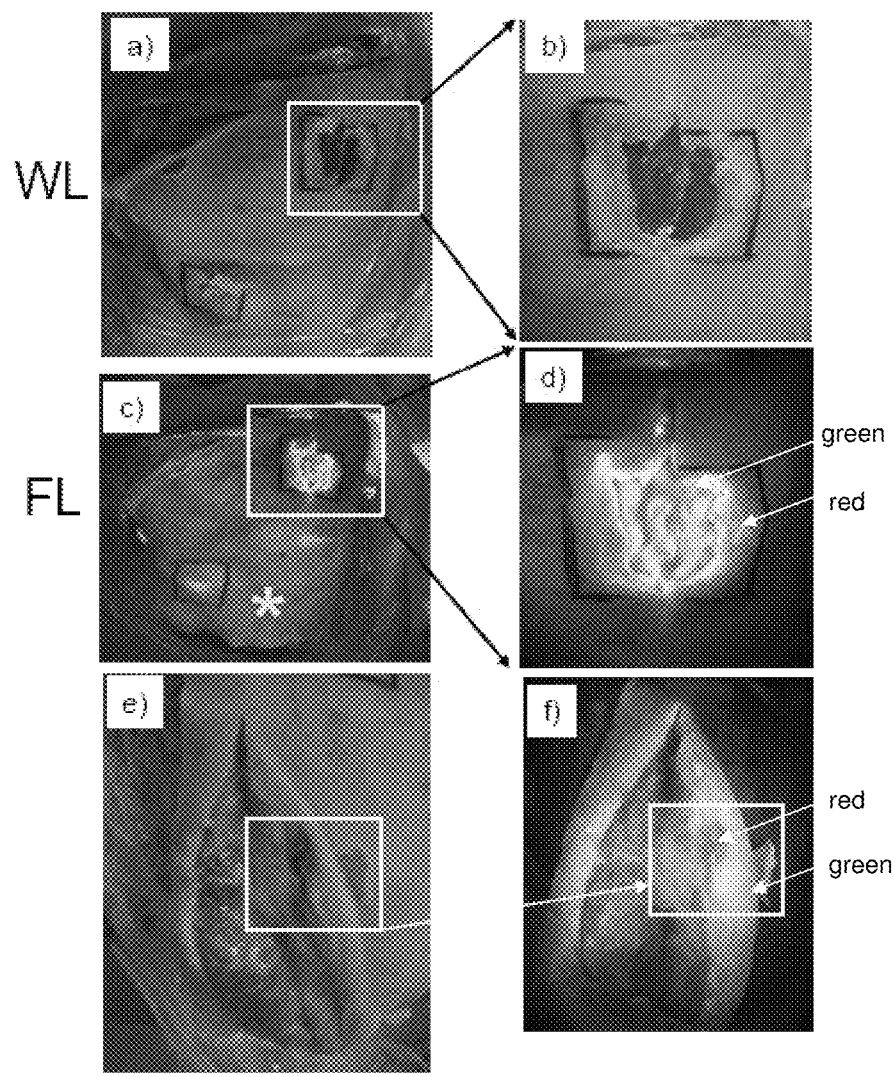
FIG. 12 shows images of a simulated animal wound model, demonstrating non-invasive autofluorescence detection of bacteria using a device for fluorescence-based monitoring in accordance with the present disclosure.

Reference is now made to FIG. 12. A handheld device in accordance with the present disclosure was tested in a model of wounds contaminated with bacteria. For this, pig meat, with skin, was purchased from a butcher. To simulate wounds, a scalpel was used to make incisions, ranging in size from 1.5 cm$^2$ to 4 cm$^2$ in the skin, and deep enough to see the muscle layer. The device was used to image some meat samples without (exogenous) addition of bacteria to the simulated wounds. For this, the meat sample was left at room temperature for 24 h in order for bacteria on the meat to grow, and then imaging was performed with the device using both white light reflectance and autofluorescence, for comparison.

To test the ability of the device to detect connective tissues and several common bacteria present in typical wounds, a sample of pig meat with simulated wounds was prepared by applying six bacterial species to each of six small 1.5 cm$^2$ wound incision sites on the skin surface: *Streptococcus pyogenes, Serratia marcescens, Staphylococcus aureus, Staphylococcus epidermidis, Escherichia coli,* and *Pseudomonas aeruginosa*. An additional small incision was made in the meat skin, where no bacteria were added, to serve as a control. However, it was expected that bacteria from the other six incisions sites would perhaps contaminate this site in time. The device was used to image the bacteria-laden meat sample using white light reflectance and violet/blue light-induced tissue autofluorescence emission, using both a dual emission band (450-505 nm and 590-650 nm) emission filter and a single band (635+/−10 nm) emission filter, on the left and a single band filter over the course of three days, at 24 h time intervals, during which the meat sample was maintained at 37° C. Imaging was also performed on the styrofoam container on which the meat sample was stored during the three days.

FIG. 12 shows the results of the device being used for non-invasive autofluorescence detection of bacteria in a simulated animal wound model. Under standard white light imaging, bacteria were occult within the wound site, as shown in inset a) of FIG. 12 and magnified in inset b) of FIG. 12. However, under violet/blue excitation light, the device was capable of allowing identification of the presence of bacteria within the wound site based on the dramatic increase in red fluorescence from bacterial porphyrins against a bright green fluorescence background from connective tissue (e.g., collagen and elastins) as seen in inset c) of FIG. 12 and magnified in inset d) of FIG. 12. Comparison of inset b) and inset d) shows a dramatic increase in red fluorescence from bacterial porphyrins against a bright green fluorescence background from connective tissue (e.g., collagen and elastins). It was noted that with autofluorescence, bacterial colonies were also detected on the skin surface based on their green fluorescence emission causing individual colonies to appear as punctuate green spots on the skin. These were not seen under white light examination. Fluorescence imaging of connective tissues aided in determining the wound margins as seen in inset e) and inset f) of FIG. 12, and some areas of the skin (marked '*' in inset c)) appeared more red fluorescent than other areas, potentially indicating subcutaneous infection of porphyrin-producing bacteria. Insets e) and f) also show the device detecting red fluorescent bacteria within the surgical wound, which are occult under white light imaging.

The device mapped biodistribution of bacteria within the wound site and on the surrounding skin and thus may aid in targeting specific tissue areas requiring swabbing or biopsy for microbiological testing. Furthermore, using the imaging device may permit the monitoring of the response of the bacterially-infected tissues to a variety of medical treatments, including the use of antibiotics and other therapies, such as antibiotics, wound debridement, wound cleaning, photodynamic therapy (PDT), hyperbaric oxygen therapy (HOT), low level light therapy, or anti-matrix metalloproteinase (MMP). The device may be useful for visualization of bacterial biodistribution at the surface as well as within the tissue depth of the wound, and also for surrounding normal tissues. The device may thus be useful for indicating the spatial distribution of an infection.

Additional Examples

Figure 13:
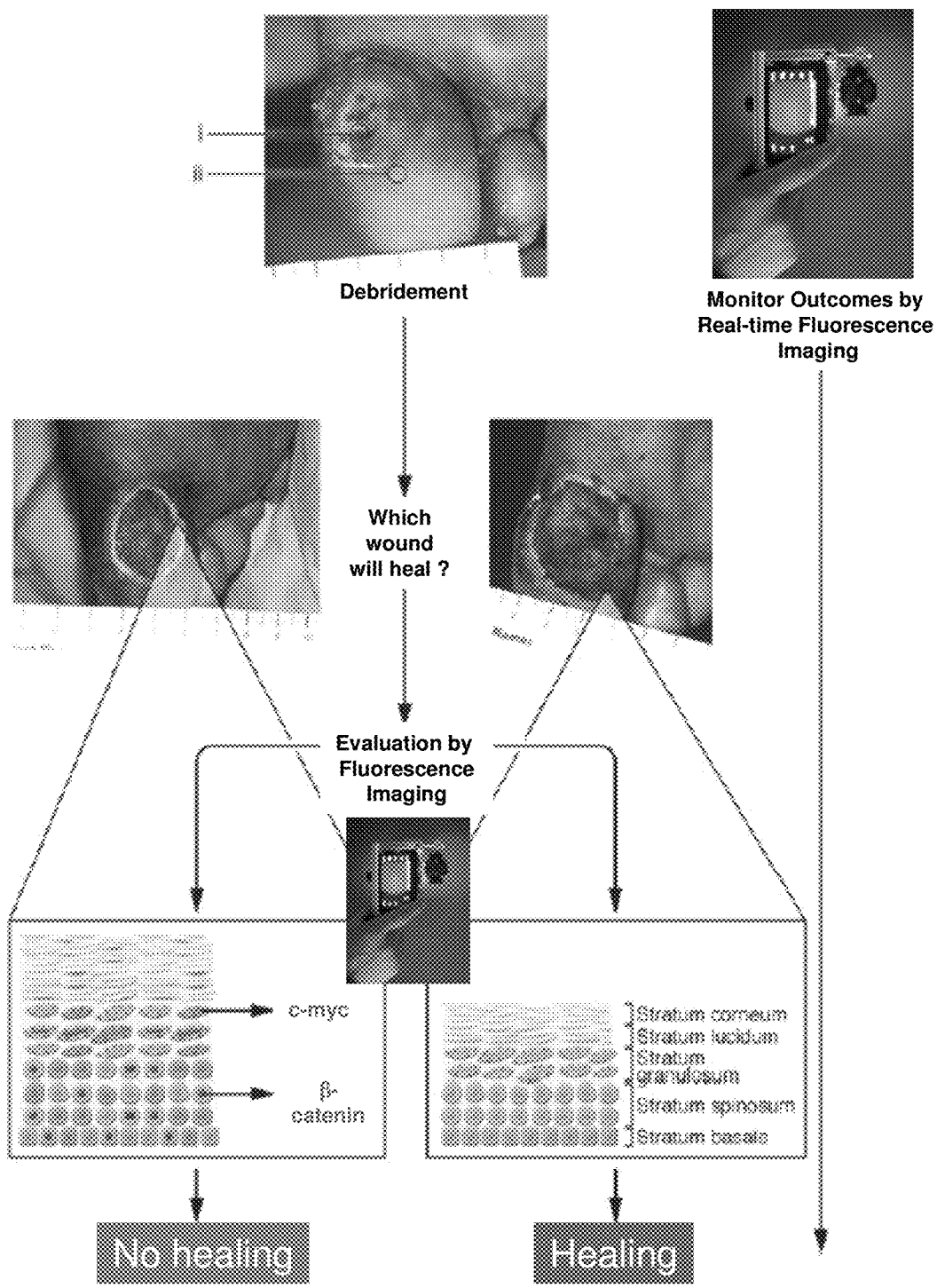
FIG. 13 illustrates an example of monitoring of a chronic wound.

Reference is now made to FIG. 13. As an example, imaging devices in accordance with the present disclosure and as discussed above may be used clinically to determine the healing status of a chronic wound and the success of wound debridement. For example, a typical foot ulcer in a person with diabetes is shown in the figure, with: (i) the nonhealing edge (i.e., callus) containing ulcerogenic cells with molecular markers indicative of healing impairment and (ii) phenotypically normal but physiologically impaired cells, which can be stimulated to heal. Despite a wound's appearance after debridement, it may not be healing and may need to be evaluated for the presence of specific molecular markers of inhibition and/or hyperkeratotic tissue (e.g., c-myc and β-catenin). Using the imaging device of the present disclosure in combination with exogenous fluorescently labeled molecular probes against such molecular targets, the clinician may be able to determine the in-situ expression of molecular biomarkers. With the device of the present disclosure, once a wound is debrided, fluorescence imaging of the wound area and image analyses may allow biopsy targeting for subsequent immunohistochemistry and this may determine whether the extent of debridement was sufficient. If the extent of debridement was insufficient, as shown in the lower left diagram, cells positive for c-myc (which appears green) and nuclear β-catenin (which appears purple) may be found based on their fluorescence, indicating the presence of ulcerogenic cells, which may prevent the wound from healing properly and indicate that additional debridement is necessary. Lack of healing may also be demarcated by a thicker epidermis, thicker cornified layer, and presence of nuclei in the cornified layer. If the debridement was successful, as in the lower right lower diagram, no staining for c-myc or β-catenin may be found, indicating an absence of ulcerogenic cells and successful debridement. These markers of inhibition may be useful, but the goal is actual healing as defined by the appearance of new epithelium, decreased area of the wound, and no drainage. This information may be collected using the fluorescence imaging device and stored electronically in the patient's medical record, which may provide an objective analysis coupled with pathology and microbiology reports. By comparing expected healing time with actual healing (i.e., healing progress) time using the imaging device, adaptive treatment strategies may be implemented on a per-patient basis.

Figure 14:
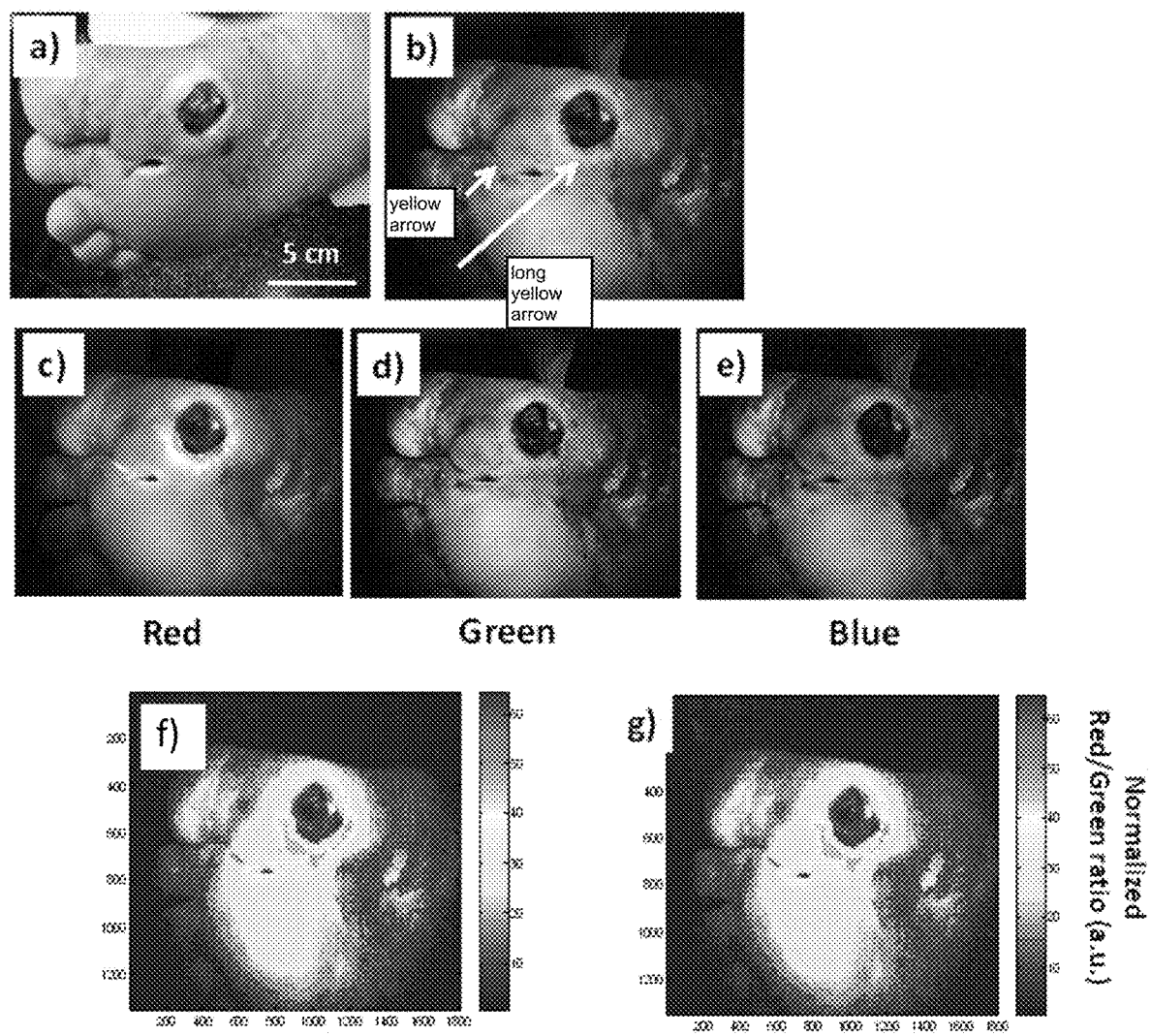
FIGS. 14-28 show examples of the use of a device for fluorescence-based monitoring in accordance with the present disclosure for imaging wounds and conditions in clinical patients.

FIG. 14 shows an example of the use of a device in accordance with the present disclosure for imaging wound healing of a pressure ulcer. Inset a) of FIG. 14 shows a white light image taken with the device of the present disclosure of the right foot of a diabetic patient with a pressure ulcer. Inset b) of FIG. 14 shows the corresponding fluorescence image, which shows the bright red fluorescence of bacteria (bacteriology results confirmed presence of heavy growth of *Staphylococcus aureus*) which are invisible under standard white light examination (yellow arrows). Note the heavy growth of *Staphylococcus aureus* bacteria around the periphery of the non-healing wound (long yellow arrow). Insets c-d) of FIG. 14 show the spectrally-separated (unmixed) red-green-blue images of the raw fluorescence image in inset b), which are used to produce spectrally-encoded image maps of the green (e.g. collagen) and red (e.g. bacteria) fluorescence intensities calculated using mathematical algorithms and displayed in false color with color scale. Insets f-g) of FIG. 14 show examples of image-processing methods used to enhance the contrast of the endogenous bacterial autofluorescence signal by calculating the red/green fluorescence intensity ratio to reveal the presence and biodistribution of bacteria (red-orange-yellow) within and around the open wound. This data illustrates the ability to use custom or commercially-available image-analysis software to mathematically analyze the fluorescence images obtained by devices in accordance with the present disclosure and display them in a meaningful way for clinical use, and this may be done in real-time. (Scale bar 1 cm).

Figure 15:
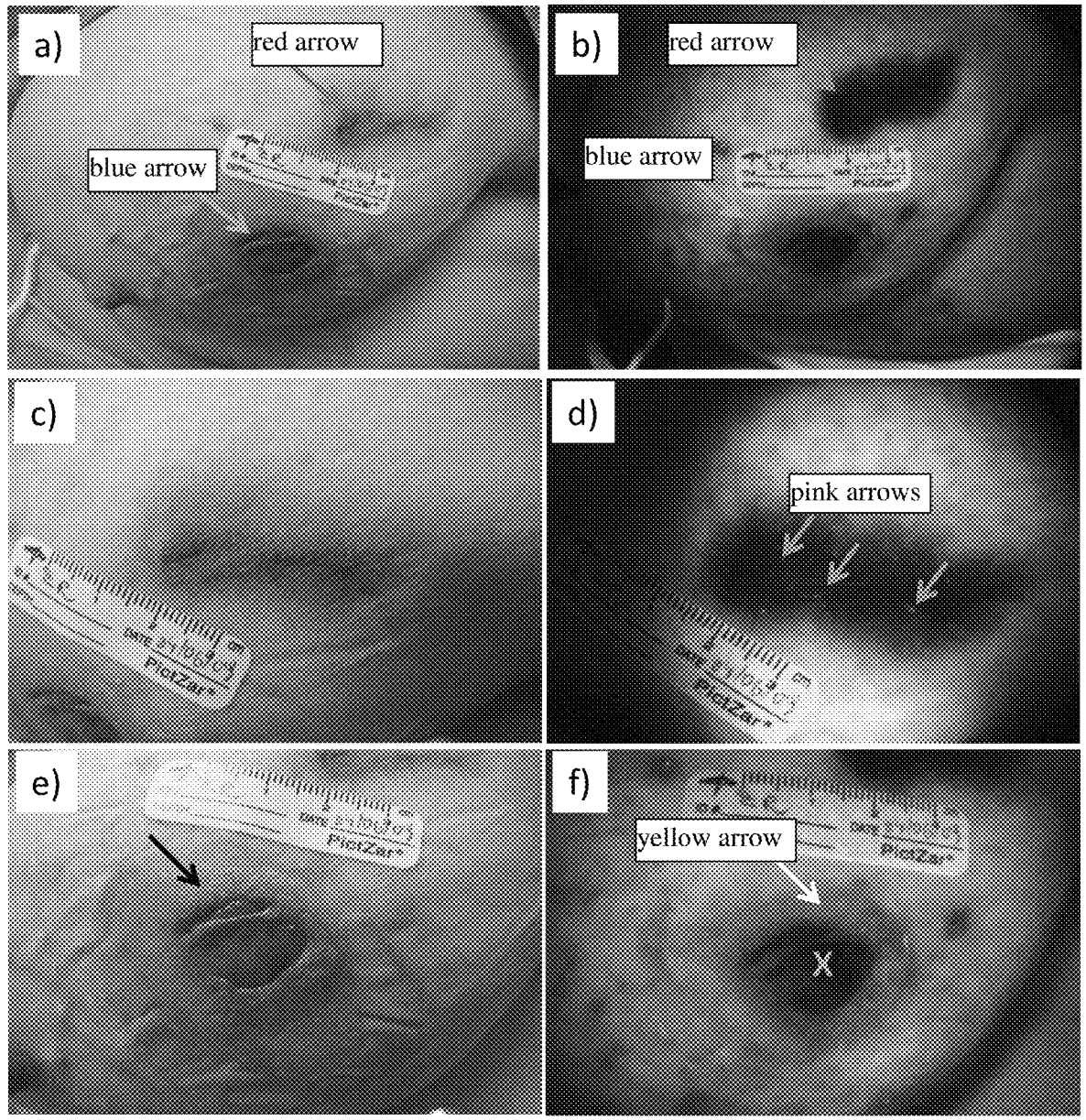

FIG. 15 shows an example of the use of a device in accordance with the present disclosure for imaging a chronic non-healing wound. Inset a) of FIG. 15 shows a white light image taken with the device of the present disclosure of the left breast of a female patient with *Pyoderma gangrenosum*, shows a chronic non-healing wound (blue arrow) and a healed wound (red arrow). Bacteria typically cannot be visualized by standard white light visualization used in conventional clinical examination of the wounds. Inset b) of FIG. 15 shows the corresponding fluorescence image of the same wounds (in this example, using 405 nm excitation, 500-550 nm emission (green), >600 nm emission (red)). Note that the non-healed wound appears dark colored under fluorescence (mainly due to blood absorption of the excitation and fluorescence emission light), while bacteria appear as punctuate bright red spots in the healed wound (red arrow). Under fluorescence, normal surrounding skin appears cyan-green due to endogenous collagen fluorescence (405 nm excitation). By contrast, the non-healed wound (blue arrow) appears to have a band of very bright red fluorescence around the wound border, confirmed with swab cultures (bacteriology) to contain a heavy growth of *Staphylococcus aureus* (with few Gram positive bacilli and rare Gram positive cocci, confirmed by microscopy). Inset c) of FIG. 15 shows a white light image of the healed wound in insets a) and b) and inset d) of FIG. 15 shows the corresponding fluorescence image showing bright red fluorescence from bacteria (pink arrows), which are occult under white light. Inset e) of FIG. 15 shows a white light image and inset f) of FIG. 15 shows a corresponding fluorescence image of the non-healed breast wound. Note that bacteria (*Staphylococcus aureus*) appear to be mainly localized around the edge/boundary of the wound (yellow arrow), while less bacteria are located within the wound (X), determined by the biodistribution of bacteria directly visualized using fluorescence imaging, but invisible under white light (black arrow, e). (Scale bar in cm).

Figure 16:
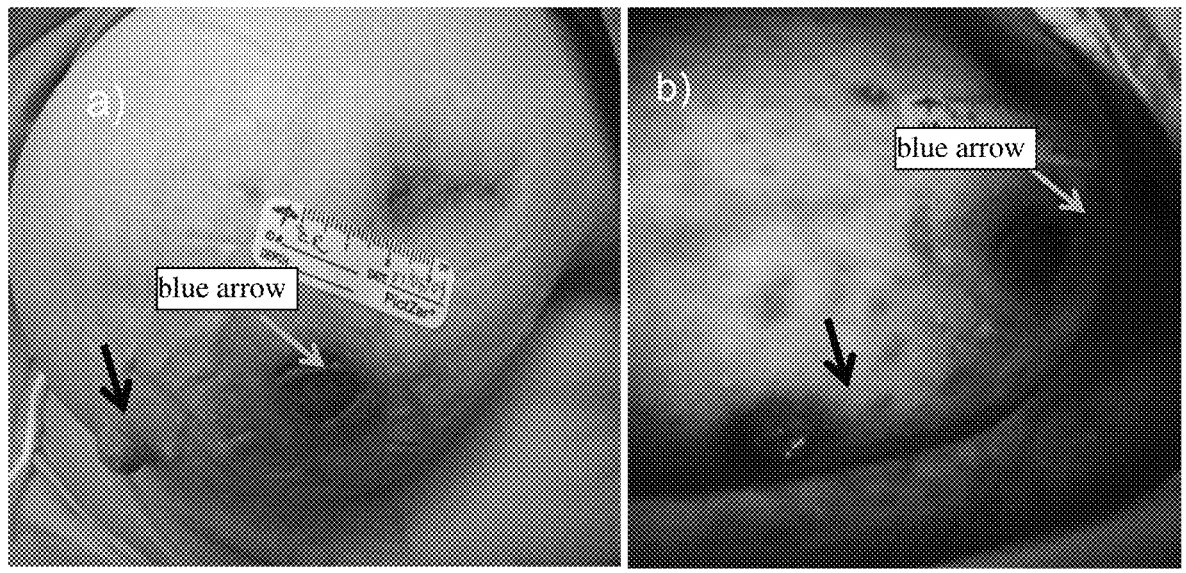

FIG. 16 further illustrates imaging of a chronic non-healing wound using an exemplary imaging device in accordance with the present disclosure. Inset a) of FIG. 16 shows a white light image taken with the device of the present disclosure of a left breast of a female patient with *Pyoderma gangrenosum*, showing chronic non-healing wound (blue arrow) and healed wound (blue arrow). Bacteria cannot be visualized by standard white light visualization used in clinical examination of the wounds. Inset b) of FIG. 16 shows a corresponding fluorescence image of the same wounds (405 nm excitation, 500-550 nm emission (green), >600 nm emission (red)). While the nipple appears to be normal under white without obvious contamination of bacteria, fluorescence imaging shows the presence of bacteria emanating from the nipple ducts. Swabs of the nipple showed bacteria were *Staphylococcus epidermidis* (Occasional growth found on culture). (Scale bar in cm)

Figure 17:
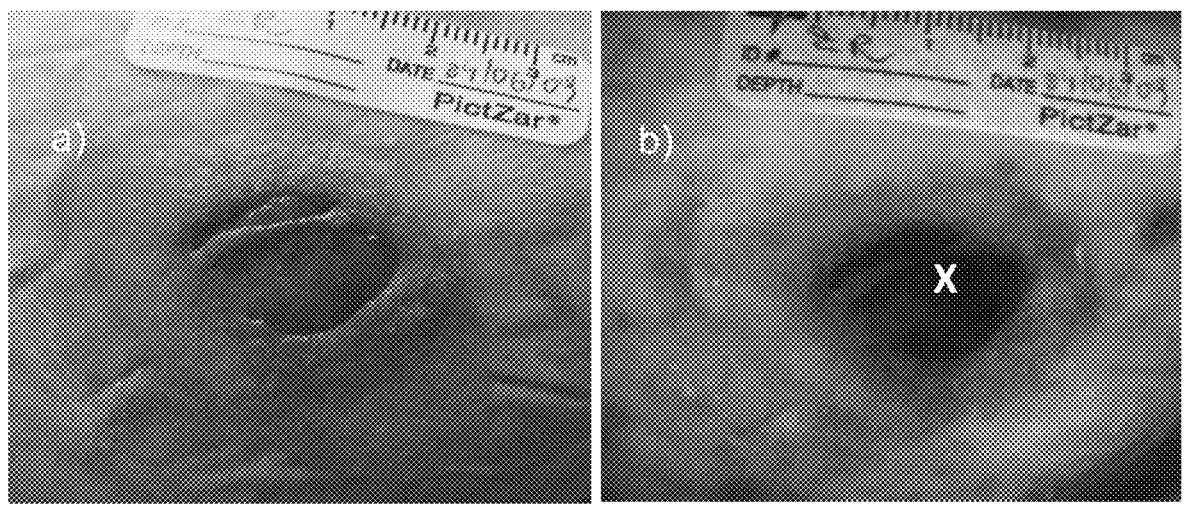

FIG. 17 shows a central area and border of a chronic non-healing wound imaged using an imaging device in accordance with the present disclosure. Inset a) of FIG. 17 shows a white light image taken with the device of the present disclosure of a left breast of a female patient with *Pyoderma gangrenosum*, showing the central area and border of a chronic non-healing wound. Inset b) of FIG. 17 shows a corresponding fluorescence image of the non-healed breast wound (405 nm excitation, 500-550 nm emission (green), >600 nm emission (red)). Note that bacteria (*Staphylococcus aureus*; shown by bacterial swabbing) appear to be mainly localized around the edge/boundary of the wound, while less bacteria are located within the wound (X), determined by the biodistribution of bacteria directly visualized using fluorescence imaging, but invisible under white light. (Scale bar in cm).

Figure 18:
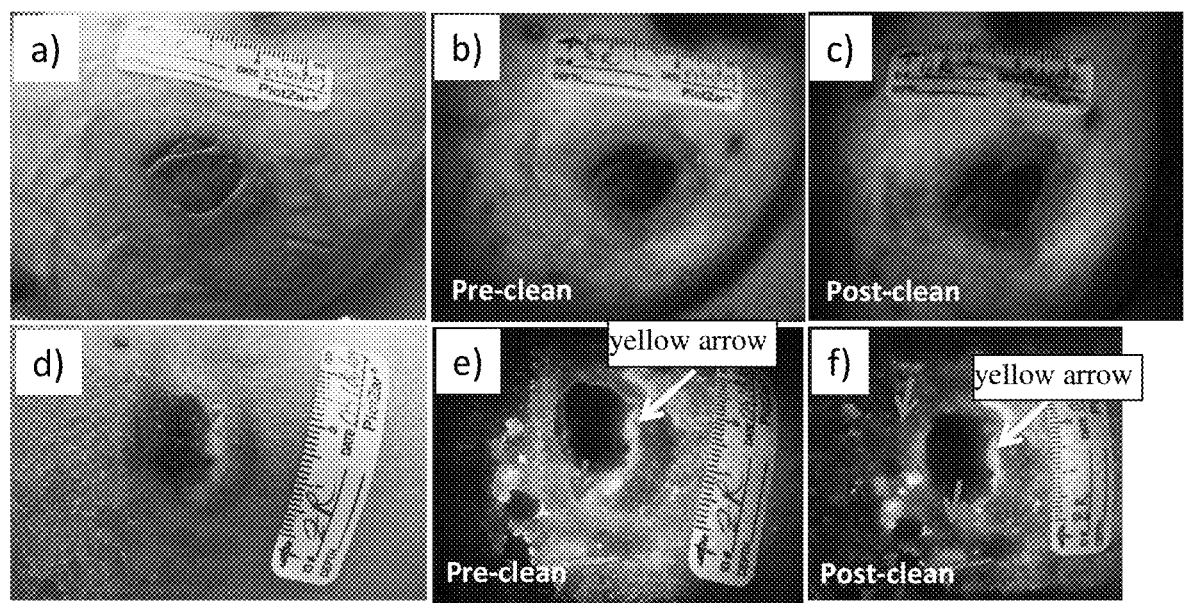

FIG. 18 shows further images of a chronic non-healing wound using an imaging device in accordance with the present disclosure. Inset a) of FIG. 18 shows a white light image taken with the device of the present disclosure of a left breast of a female patient with *Pyoderma gangrenosum*, showing chronic non-healing wound. Bacteria cannot be visualized by standard white light visualization used in clinical examination of the wounds. Inset b) of FIG. 18 shows a corresponding fluorescence image of the same wound (405 nm excitation, 500-550 nm emission (green), >600 nm emission (red)). Fluorescence imaging shows the presence of bacteria around the wound edge/border pre-cleaning (inset (b)) and post-cleaning (inset (c) of FIG. 18). In this example, cleaning involved the use of standard gauze and phosphate buffered saline to wipe the surface of the wound (within and without) for 5 minutes. After cleaning, the red fluorescence of the bacteria is appreciably decreased indicating that some of the red fluorescent bacteria may reside below the tissue surface around the edge of the wound. Small amounts of bacteria (red fluorescent) remained within the wound center after cleaning. This illustrates the use of the imaging device to monitor the effects of wound cleaning in real-time. As an additional example, inset d) of FIG. 18 shows a white light image of a chronic non-healing wound in the same patient located on the left calf. Inset e) of FIG. 18 shows the corresponding fluorescence image pre-cleaning (inset (e)) and post-cleaning (inset (f) of FIG. 18). Swabbing of the central area of the wound revealed the occasional growth of *Staphylococcus aureus*, with a heavy growth of *Staphylococcus aureus* at the edge (yellow arrow). Cleaning resulted in a reduction of the fluorescent bacteria (*Staphylococcus aureus*) on the wound surface as determined using the handheld optical imaging device. The use of the imaging device resulted in the real-time detection of white light-occult bacteria and this allowed an alteration in the way the patient was treated such that, following fluorescence imaging, wounds and surrounding (bacteria contaminated) were either re-cleaned thoroughly or cleaned for the first time because of de novo detection of bacteria. Also, note that the use of a disposable adhesive measurement-calibration 'strip' for aiding in imaging-focusing and this "strip" may be adhered to any part of the body surface (e.g., near a wound) to allow wound spatial measurements. The calibration strip may also be distinctly fluorescent and may be used to add patient-specific information to the images, including the use of multiple exogenous fluorescent dyes for "barcoding" purposes—the information of which can be integrated directly into the fluorescence images of wounds. (Scale bar in cm).

Figure 19:
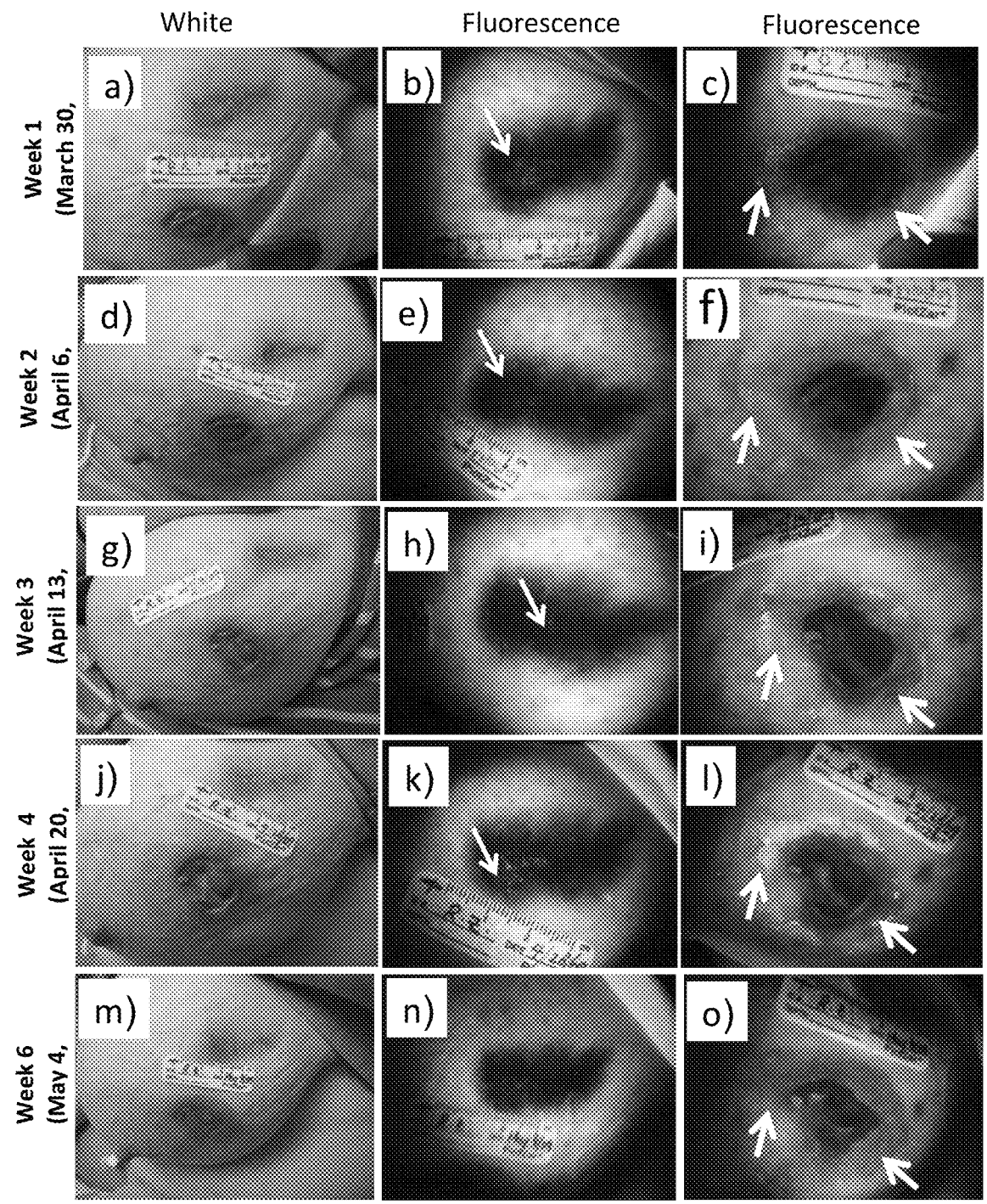

FIG. 19 illustrates use of an imaging devices in accordance with the present disclosure for monitoring wound healing over time. The imaging device of the present disclosure is used for tracking changes in the healing status and bacterial biodistribution (e.g. contamination) of a non-healing chronic wound from the left breast of a female patient with *Pyoderma gangrenosum*. White light images (see column showing insets a-m in FIG. 19) and corresponding fluorescence images of the healed wound (see column showing insets b-n in FIG. 19) and of the chronic non-healing wound (see column showing insets c-o in FIG. 19) are shown over the course of six weeks. (405 nm excitation, 500-550 nm emission (green), >600 nm emission (red)), taken using the imaging device under both white light and fluorescence modes. In the column of insets b-n, the presence of small bright red fluorescence bacterial colonies is detected (yellow arrows), and their localization changes over time within the healed wound. Bacterial swabs confirmed that no bacteria were detected on microscopy and no bacterial growth was observed in culture. In the column of insets c-o), by contrast, the non-healed wound has a band of very bright red fluorescence around the wound border, confirmed with swab cultures (bacteriology) to contain a heavy growth of *Staphylococcus aureus* (with few Gram positive bacilli and rare Gram positive cocci, confirmed by microscopy), which changes in biodistribution over time (i.e., see column of insets c-o). This data demonstrates that imaging devices in accordance with the present disclosure may yield real-time biological and molecular information as well as be used to monitor morphological and molecular changes in wounds over time.

Figure 20:
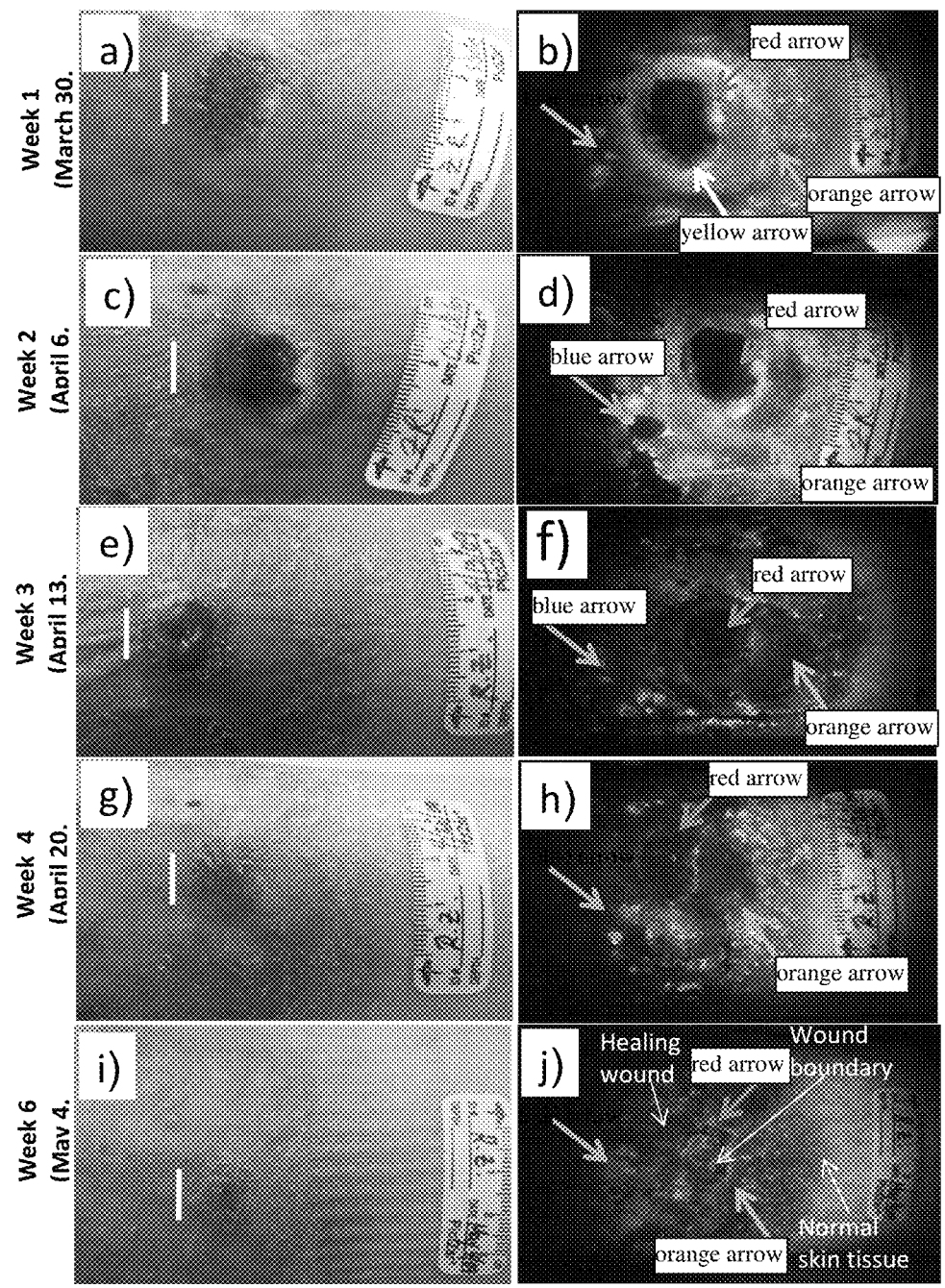

FIG. 20 shows another example of the use of the devices in accordance with the present disclosure for monitoring wound status over time. In FIG. 20, the imaging device was used to track changes in the healing status and bacterial biodistribution (e.g. contamination) of a wound from the left calf of 21 year old female patient with *Pyoderma gangrenosum*. White light images (see column of insets a-j in FIG. 20) and corresponding fluorescence images (see column of insets b-j in FIG. 20) of a wound being treated using hyperbaric oxygen therapy (HOT) are shown over the course of six weeks. (Fluorescence parameters: 405 nm excitation, 500-550 nm emission (green), >600 nm emission (red)). Column of insets a-i) White light images reveal distinct macroscopic changes in the wound as it heals, indicated by the reduction in size over time (e.g. closure) from week 1 (~2 cm long axis diameter) through to week 6 (~0.75 cm long axis diameter). In the column of insets b-j, the real-time fluorescence imaging of endogenous bacterial fluorescence (autofluorescence) in and around the wound can be tracked over time and correlated with the white light images and wound closure measurements (column of insets a-i). Inset b of FIG. 20 shows a distinct green band of fluorescence at the immediate boundary of the wound (yellow arrow; shown to be contaminated heavy growth of *Staphylococcus aureus*), and this band changes over time as the wound heals. Red fluorescence bacteria are also seen further away from the wound (orange arrow), and their biodistribution changes over time (see column of insets b-j). The wound-to-peri-wound-to-normal tissue boundaries can be seen clearly by fluorescence in image inset j of FIG. 20. Connective tissue (in this example, collagens) in normal skin appear as pale green fluorescence (inset j) and connective tissue remodeling during wound healing can be monitored over time, during various wound treatments including, as is the case here, hyperbaric oxygen therapy of chronic wounds.

Figure 21:
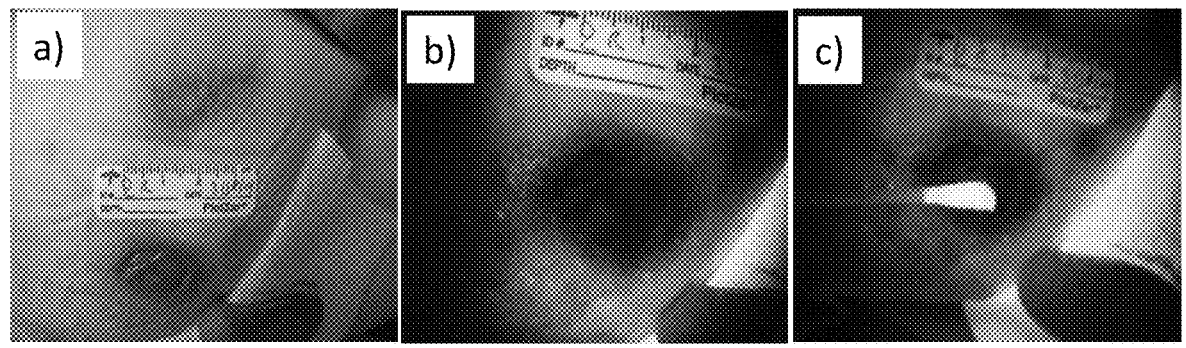

FIG. 21 illustrates use of imaging devices in accordance with the present disclosure for targeting bacterial swabs during routine wound assessment in the clinic. Under fluorescence imaging, the swab can be directed or targeted to specific areas of bacterial contamination/infection using fluorescence image-guidance in real-time. This may decrease the potential for contamination of non-infected tissues by reducing the spread of bacteria during routine swabbing procedures, which may be a problem in conventional wound swabbing methods. Swab results from this sample were determined to be *Staphylococcus aureus* (with few Gram positive bacilli and rare Gram positive cocci, confirmed by microscopy).

Figure 22:
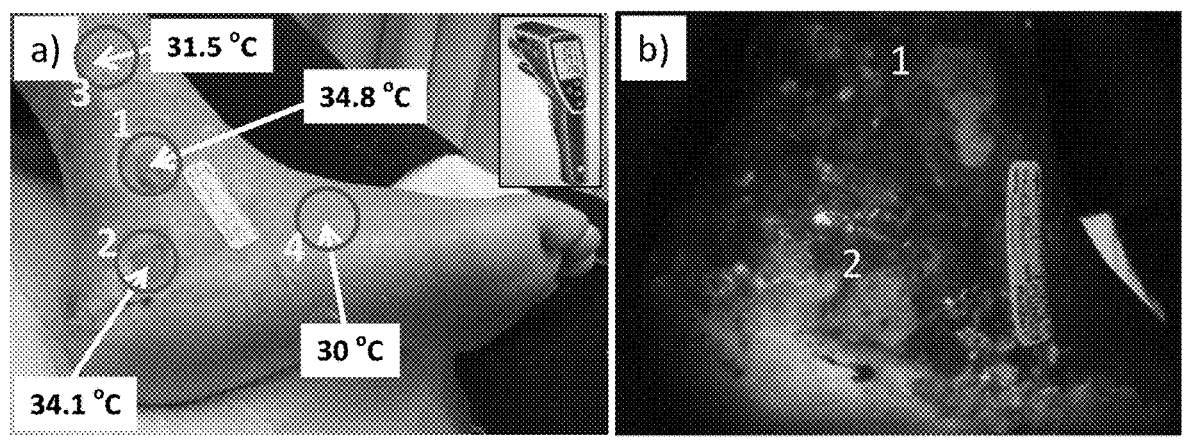

FIG. 22 shows an example of the co-registration of a) white light and b) corresponding fluorescence images made with an imaging device in accordance with the present disclosure in a patient with diabetes-associated non-healing foot ulcers. Using a non-contact temperature measuring probe (inset in a) with cross-laser sighting, direct temperature measurements were made on normal skin (yellow "3 and 4") and within the foot ulcers (yellow "1 and 2") (infected with *Pseudomonas aeruginosa*, as confirmed by bacteriological culture), indicating the ability to add temperature-based information to the wound assessment during the clinical examination. Infected wounds have elevated temperatures, as seen by the average 34.45° C. in the infected wounds compared with the 30.75° C. on the normal skin surface, and this data illustrates the possibility of multimodality measurements, which include white light, fluorescence and thermal information for wound health/infectious assessment in real-time. Note that both non-healing wounds on this patient's right foot contained heavy growth of *Pseudomonas aeruginosa* (in addition to Gram positive cocci and Gram negative bacilli), which in this example appear as bright green fluorescent areas within the wound (inset b) of FIG. 22).

Figure 23:
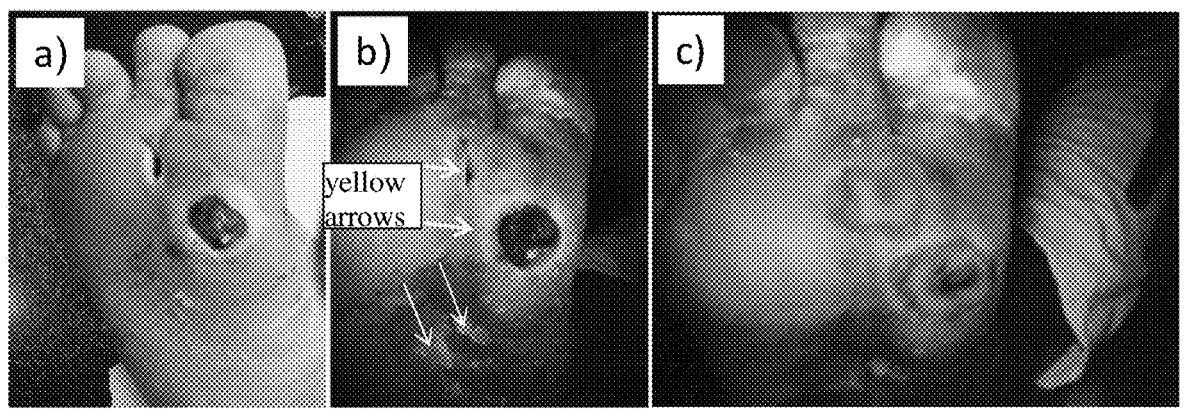

FIG. 23 shows an example of the use of an imaging device in accordance with the present disclosure for monitoring a pressure ulcer. Inset a of FIG. 23 shows a white light image taken with the imaging device in accordance with the present disclosure of the right foot of a Caucasian diabetic patient with a pressure ulcer. Inset b of FIG. 23 shows a corresponding fluorescence image showing the bright red fluorescence of bacteria (bacteriology results confirmed presence of heavy growth of *Staphylococcus aureus*), which are invisible under standard white light examination (yellow arrows). Dead skin appears as a white/pale light green color (white arrows). Note the heavy growth of *Staphylococcus aureus* bacteria around the periphery of the non-healing open wounds (yellow arrows). Inset c) of FIG. 23 shows the fluorescence imaging of a topically applied silver antimicrobial dressing. The imaging device in accordance with the present disclosure may be used to detect the endogenous fluorescence signal from advanced wound care products (e.g., hydrogels, wound dressings, etc.) or the fluorescence signals from such products that have been prepared with a fluorescent dye with an emission wavelength within the detection sensitivity of the imaging detector on the device. The device may be used for image-guided delivery/application of advanced wound care treatment products and to subsequently monitor their distribution and clearance over time.

Figure 24:
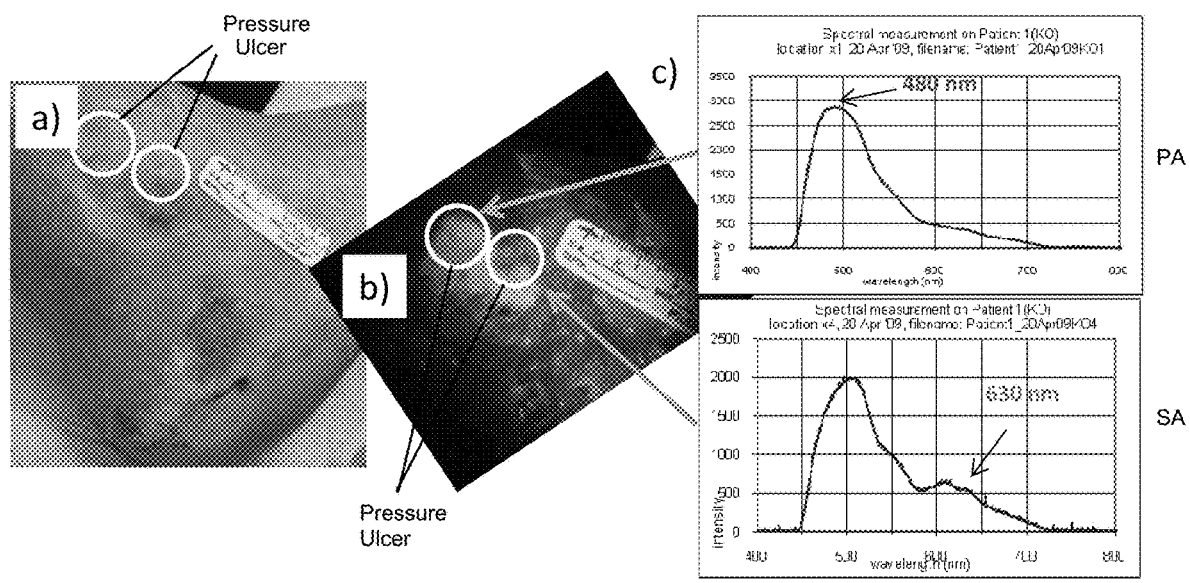

FIG. 24 shows another example of the use of a device in accordance with the present disclosure for monitoring a pressure ulcer. Inset a) of FIG. 24 shows a white light image taken with the device of the present disclosure of the right foot of a Caucasian diabetic patient with a pressure ulcer. Inset b) of FIG. 24 shows a corresponding fluorescence image showing the bright red fluorescent area of bacteria (bacteriology results confirmed presence of heavy growth of *Staphylococcus aureus*, SA) at the wound edge and bright green fluorescent bacteria (bacteriology results confirmed presence of heavy growth of *Pseudomonas aeruginosa*, PA) which are both invisible under standard white light examination. Inset c) of FIG. 24 shows fluorescence spectroscopy taken of the wound that revealed unique spectral differences between these two bacterial species: SA has a characteristic red (about 630 nm) autofluorescence emission peak, while PA lacks the red fluorescence but has a strong green autofluorescence peak at around 480 nm.

The handheld device in accordance with the present disclosure spectrally distinguishes bacteria from connective tissues and blood in vivo. Using $\lambda\text{exc}=405\_20$ nm and $\lambda\text{emiss}=500$ to 550 nm, 590 to 690 nm, the device detects AF signals of *S. aureus, Staphylococcus epidermidis, P. aeruginosa, Candida, Serratia marcescens, Viridans* streptococci ($\alpha$-hemolytic streptococci), *Streptococcus pyogenes* ($\beta$-hemolytic streptococci), *Corynebacterium diphtheriae, Enterobacter, Enterococcus*, and methicillin-resistant *S. aureus* (MRSA), as verified by microbiological swab cultures (data from a human clinical trial by our group to be published in a forthcoming paper). This is a representative of the major types of pathogenic bacteria commonly found in infected wounds. Clinical microbiology tests confirmed that *S. aureus, S. epidermidis, Candida, S. marcescens, Viridans streptococci, Corynebacterium diphtheriae, S. pyogenes, Enterobacter*, and *Enterococcus* produced red FL (from porphyrin) while *P. aeruginosa* produced a bluish-green FL (from pyoverdin) detected by the handheld device. These spectral characteristics differ significantly from connective tissues (collagen, elastin) and blood, which appear green and dark red, respectively. A representative image of these spectral characteristics is shown in FIG. 24.

Figure 25:
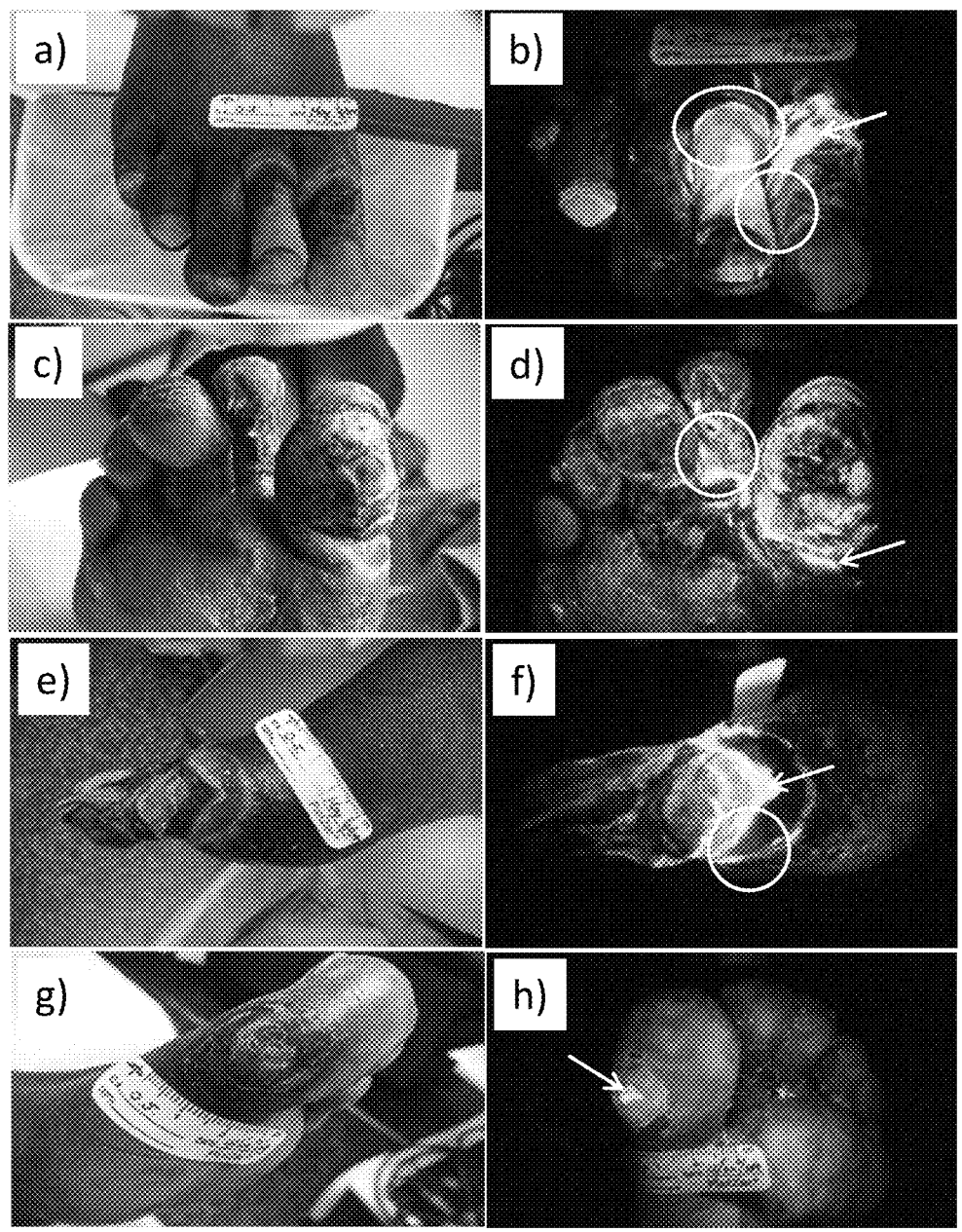

FIG. 25 shows an example of the use of a device in accordance with the present disclosure for monitoring a chronic non-healing wound. Inset a) of FIG. 25 shows a white light image taken with the imaging device of the present disclosure of chronic non-healing wounds in a 44 year old black male patient with Type II diabetes. Bacteria cannot be visualized by standard white light visualization (see column of insets α-g) of FIG. 25) used in conventional clinical examination of the wounds. Column of insets b-h) of FIG. 25 show corresponding fluorescence images of the same wounds (405 nm excitation, 500-550 nm emission (green), >600 nm emission (red)). This patient presented with multiple open non-healing wounds. Swab cultures taken from each wound area using the fluorescence image-guidance revealed the heavy growths of *Pseudomonas aruginosa* (yellow arrow), which appear bright green fluorescent, and *Serratia marcescens* (circles), which appear red fluorescent. (Scale bar in cm).

Figure 26:
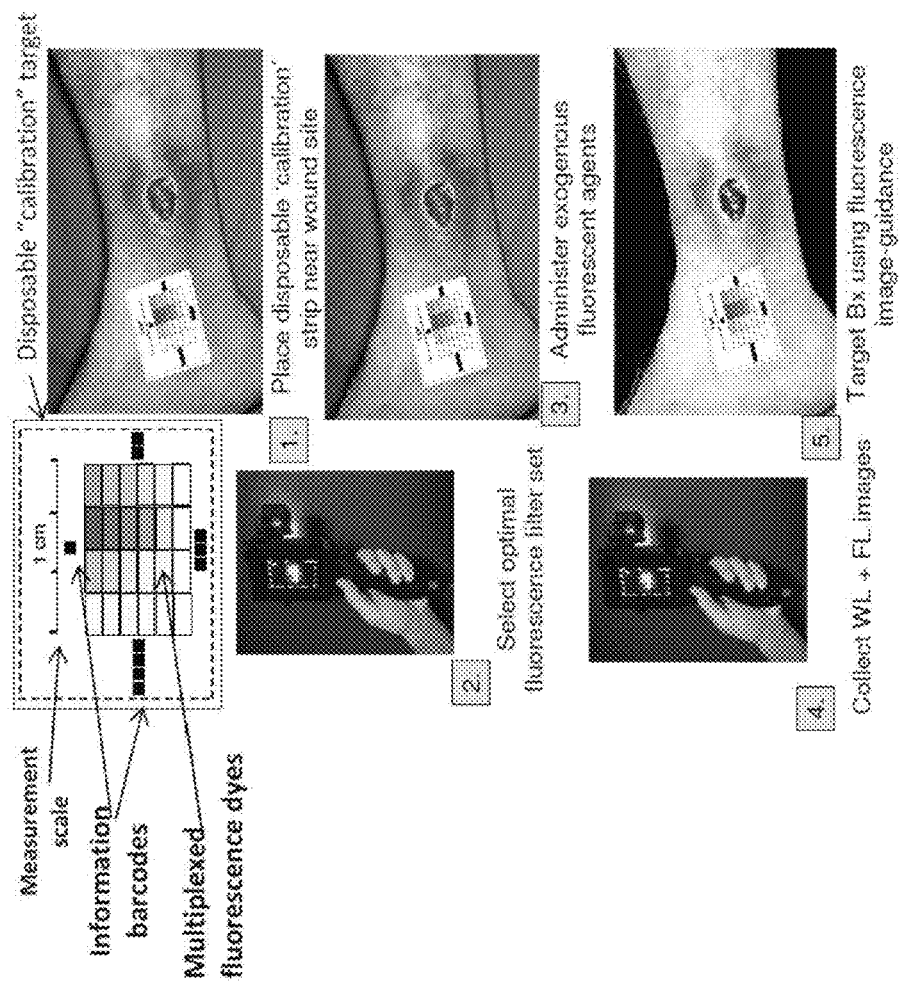

FIG. 26 is a schematic diagram illustrating an example of a use of "calibration" targets, which may be custom-designed, multi-purpose, and/or disposable, for use during wound imaging with imaging devices in accordance with the present disclosure. The strip, which in this example is adhesive, may contain a combination of one or more of: spatial measurement tools (e.g., length scale), information barcode for integrating patient-specific medical information, and impregnated concentration-gradients of fluorescent dyes for real-time fluorescence image calibration during imaging. For the latter, multiple concentrations of various exogenous fluorescent dyes or other fluorescence agents (e.g., quantum dots) may be used for multiplexed fluorescence intensity calibration, for example when more than one exogenous fluorescently-labeled probe is used for tissue/cell/molecular-targeted molecular imaging of wounds in vivo.

Figure 27:
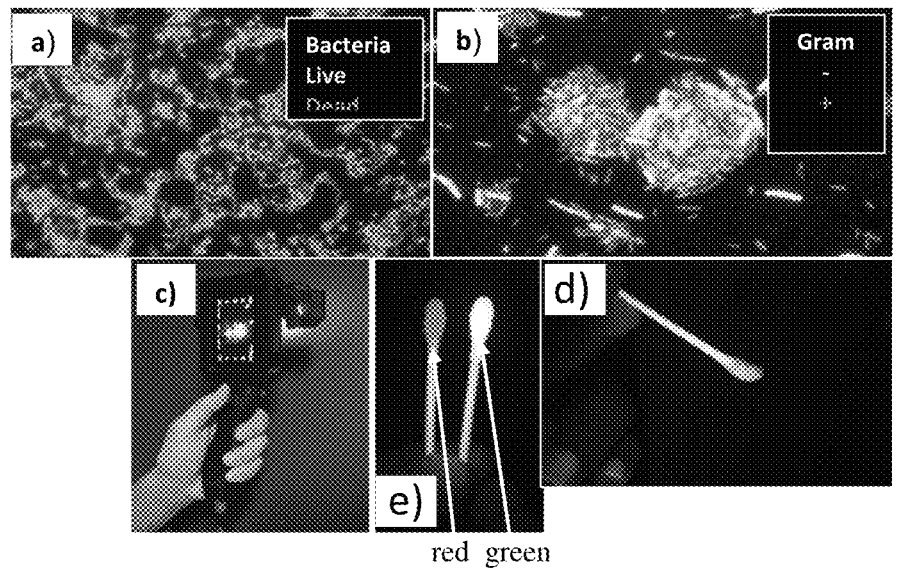

FIG. 27 shows an example of the use of an embodiment of the imaging device for monitoring bacteria, for example for monitoring a treatment response. Inset a) of FIG. 27 shows a fluorescence microscopy image of a live/dead bacteria stain sold by Invitrogen Corp. (i.e., BacLight product). Inset b) of FIG. 27 shows a fluorescence microscopy image of a Gram staining bacteria labeling stain sold by Invitrogen Corp. Using the imaging device, as shown in inset c) of FIG. 27, with such products, live (green) and dead (red) bacteria may be distinguished in real-time ex vivo (e.g., on the swab or tissue biopsy shown in inset e of FIG. 27) following bacterial swabbing of a wound, or other body surface, for example, in the swabbing of the oral buccal cheek, as in inset d of FIG. 27. This real-time bacterial Gram staining or live/dead image-based assessment may be useful for real-time or relatively rapid bacteriology results that may be used for refining treatments, such as antibiotic or other disinfective treatments, or for monitoring treatment response.

Figure 28:
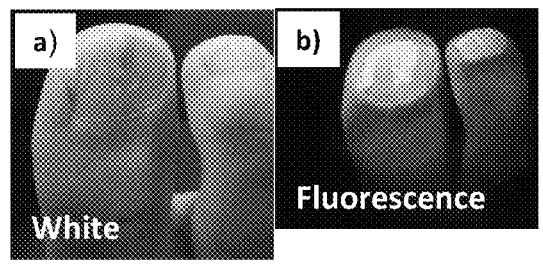

FIG. 28 shows an example of the use of a device in accordance with the present disclosure used for imaging of a toe nail infection. Inset a) of FIG. 28 shows a white light image and inset b) of FIG. 28 shows a corresponding autofluorescence image of the right toe of a subject demonstrating the enhanced contrast of the infection that fluorescence imaging provides compared to white light visualization (405 nm excitation, 500-550 nm emission (green), >600 nm emission (red)).

Additional Examples

Figure 29:
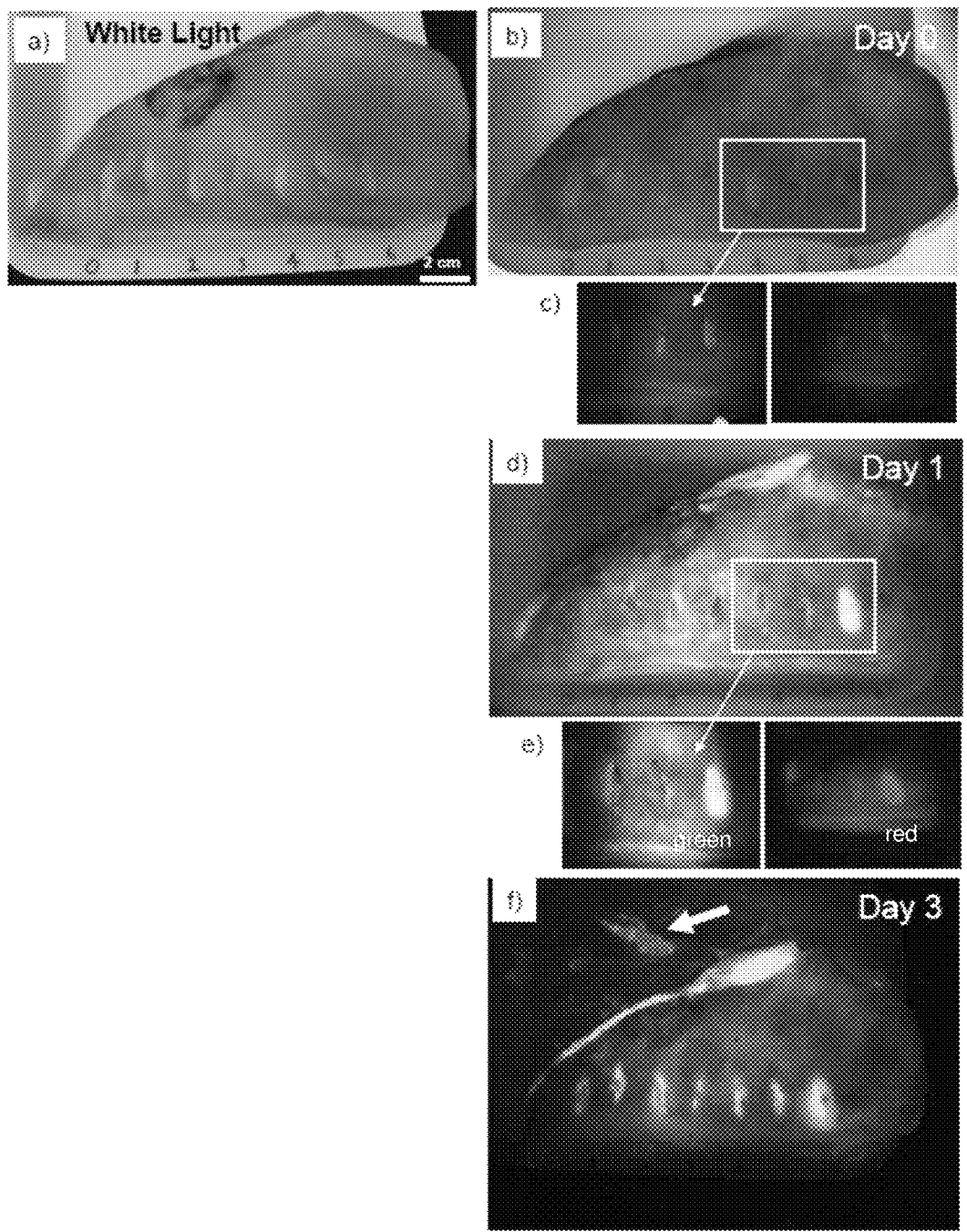
FIG. 29 shows images of a skin surface of a pig meat sample, demonstrating non-invasive autofluorescence detection of collagen and various bacterial species using a device for fluorescence-based monitoring in accordance with the present disclosure.

FIG. 29 shows an example of a device in accordance with the present disclosure being used for non-invasive autofluorescence detection of collagen and varies bacterial species on the skin surface of a pig meat sample. In contrast to white light imaging, autofluorescence imaging was able to detect the presence of several bacterial species 24 hours after they were topically applied to small incisions made in the skin (i.e., *Streptococcus pyogenes, Serratia marcescens, Staphylococcus aureus, Staphylococcus epidermidis, Escherichia coli*, and *Pseudomonas aeruginosa*). Inset a) of FIG. 29 shows a white light image of pig meat used for testing. Several bacterial species were applied to small incisions made in the skin at Day 0 and were labelled as follows: 1) *Streptococcus pyogenes,* 2) *Serratia marcescens,* 3) *Staphylococcus aureus,* 4) *Staphylococcus epidermidis,* 5) *Escherichia coli,* and 6) *Pseudomonas aeruginosa*. The imaging device was used to detect collagen and bacterial autofluorescence over time. Connective tissue fluorescence was intense and easily detected as well. Some bacterial species (e.g., *Pseudomonas aeruginosa*) produces significant green autofluorescence (450-505 nm) which saturated the device's camera. Inset b) of FIG. 29 shows an autofluorescence image at Day 0, magnified in inset c) of FIG. 29.

The device was also able to detect spreading of the bacteria over the surface of the meat over time. Inset d) of FIG. 29 shows an image at Day 1, and inset f) of FIG. 29 shows an image at Day 3, as the meat sample was maintained at 37° C. Red fluorescence can be seen in some of the wound sites (5, 6) in inset c) of FIG. 29. As shown in inset d) and magnified in inset e) of FIG. 29, after 24 h, the device detects a dramatic increase in bacterial autofluorescence from wound site 5) *Escherichia coli* and 6) *Pseudomonas aeruginosa*, with the latter producing significant green and red autofluorescence. Insets c) and e) of FIG. 29 show the device detecting fluorescence using a dual band (450-505 nm green and 590-650 nm) on the left and a single band filter (635+/−10 nm) on the right, of the wound surface. As shown in inset f), by Day 3, the device detects the significant increase in bacterial autofluorescence (in green and red) from the other wound sites, as well as the bacterial contamination (indicated by the arrow in inset f) on the styrofoam container in which the meat sample was kept. The device was also able to detect spreading of the bacteria over the surface of the meat. This demonstrates the real-time detection of bacterial species on simulated wounds, the growth of those bacteria over time, and the capability of the device to provide longitudinal monitoring of bacterial growth in wounds. The device may provide critical information on the biodistribution of the bacteria on the wound surface which may be useful for targeting bacterial swabbing and tissue biopsies. Note, in insets d) and f), the intense green fluorescence signal from endogenous collagen at the edge of the pig meat sample.

This example demonstrates the use of devices in accordance with the present disclosure for real-time detection of biological changes in connective tissue and bacterial growth based on autofluorescence alone, suggesting a practical capability of the device to provide longitudinal monitoring of bacterial growth in wounds.

Figure 3:
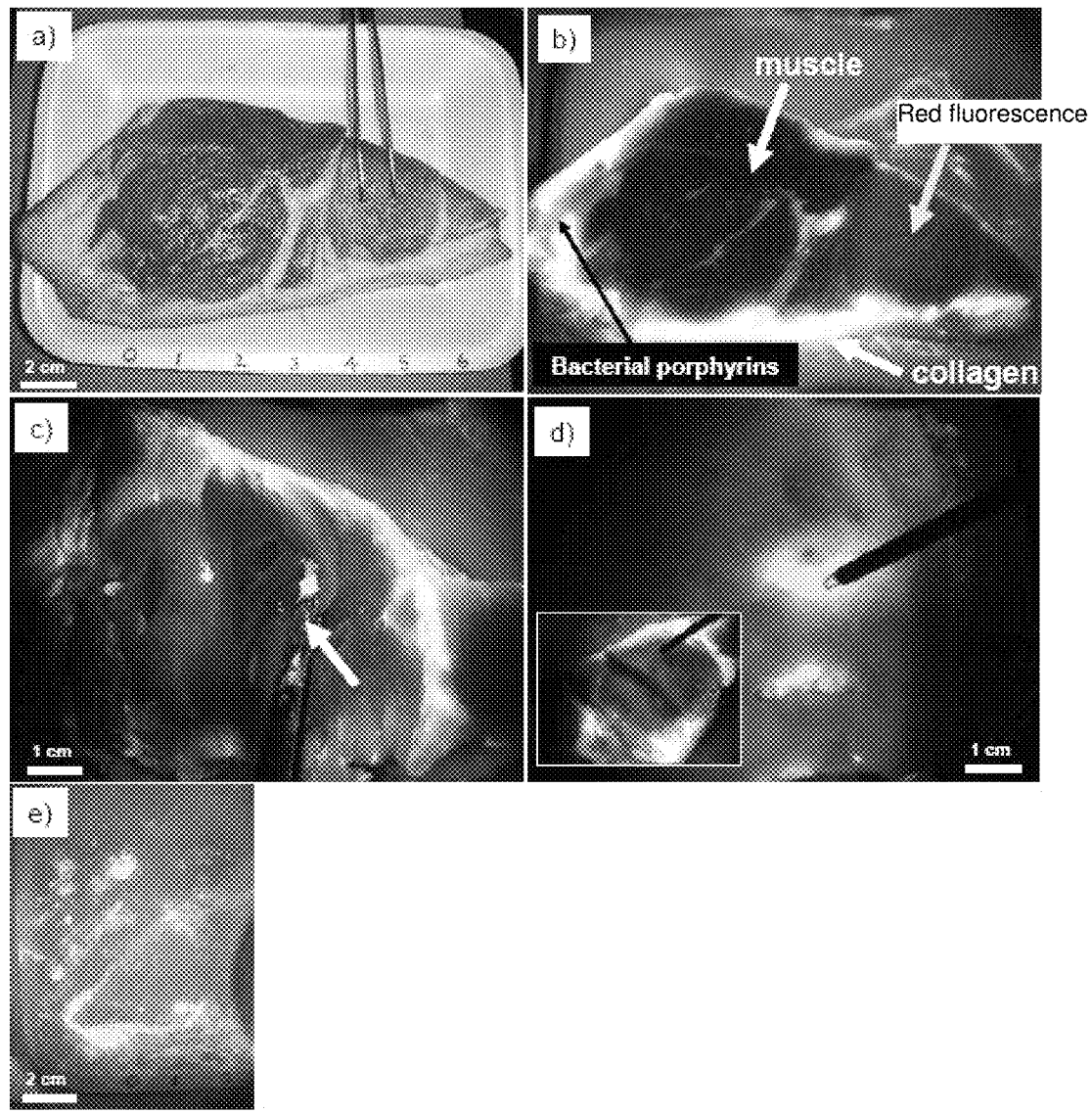
FIG. 3 shows images of a muscle surface of a pig meat sample, demonstrating the exemplary use of a device for fluorescence-based monitoring in accordance with the present disclosure for autofluorescence detection of connective tissues and bacteria.

Referring again to FIG. 3, the images show examples of a device in accordance with the present disclosure used for autofluorescence detection of connective tissues (e.g., collagen, elastin) and bacteria on the muscle surface of a pig meat sample. Inset a) of FIG. 3 shows that white light image of pig meat used for testing shows no obvious signs of bacterial/microbial contamination or spoilage. However, as seen in inset b) of FIG. 3, imaging of the same area with the device under blue/violet light excitation revealed a bright red fluorescent area of the muscle indicating the potential for bacterial contamination compared with the adjacent side of muscle. Extremely bright green autofluorescence of collagen can also be seen at the edge of the skin. In inset c) of FIG. 3, the device was used to surgically interrogate suspicious red fluorescence further to provide a targeted biopsy for subsequent pathology or bacteriology. Note also the capability of the device to detect by fluorescence the contamination (arrow) of the surgical instrument (e.g., forceps) during surgery. In inset d) of FIG. 3, the device was used to target the collection of fluorescence spectroscopy using a fibre optic probe of an area suspected to be infected by bacteria (inset shows the device being used to target the spectroscopy probe in the same area of red fluorescent muscle in insets b) and c). Inset e) of FIG. 3 shows an example of the device being used to detect contamination by various thin films of bacteria on the surface of the Styrofoam container on which the meat sample was kept. Autofluorescence of the bacteria appears as streaks of green and red fluorescence under violet/blue excitation light from the various bacterial species previously applied to the meat. Thus, the device is capable of detecting bacteria on non-biological surfaces where they are occult under standard white light viewing (as in inset a)).

In addition to detection of bacteria in wounds and on the skin surface, the device was also able to identify suspicious areas of muscle tissue, which may then be interrogated further by surgery or targeted biopsy for pathological verification, or by other optical means such as fluorescence spectroscopy using a fiber optic probe. Also, it detected contamination by various bacteria on the surface of the Styrofoam container on which the meat sample was kept. Autofluorescence of the bacteria appears as streaks of green and red fluorescence under violet/blue excitation light from the various bacterial species previously applied to the meat.

Figure 30:
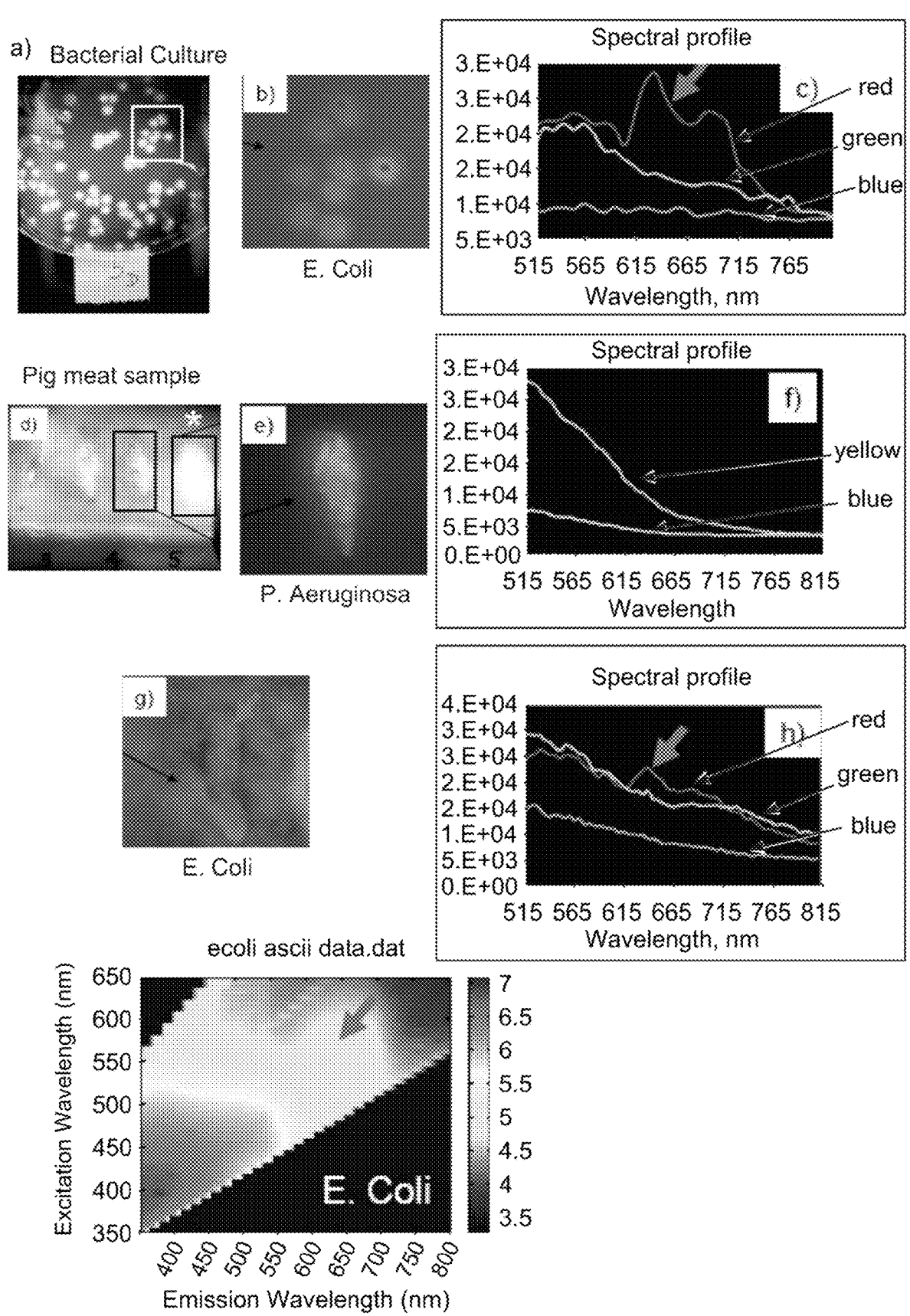
FIG. 30 shows images and spectral plots demonstrating the use of a device for fluorescence-based monitoring in accordance with the present disclosure to detect fluorescence from bacteria growing in agar plates and on the surface of a simulated wound on pig meat.

In order to determine the autofluorescence characteristics of bacteria growing in culture and in simulated skin wounds, hyperspectral/multispectral fluorescence imaging was used to quantitatively measure the fluorescence intensity spectra from the bacteria under violet/blue light excitation. Reference is now made to FIG. 30. In FIG. 30, a device in accordance with the present disclosure was used to detect fluorescence from bacteria growing in agar plates and on the surface of a simulated wound on pig meat, as discussed above for FIGS. 12 and 29. Bacterial autofluorescence was detected in the green and red wavelength ranges using the device in the culture (inset a) of FIG. 30) and meat samples (inset d) of FIG. 30). Hyperspectral/multispectral imaging was used to image the bacteria (*E. Coli*) in culture (inset b) of FIG. 30) and to measure the quantitative fluorescence intensity spectra from the bacteria (red line—porphyrins, green—cytoplasm, blue—agar background) (inset c) of FIG. 30). The red arrow shows the 635 nm peak of porphyrin fluorescence detected in the bacteria. Hyperspectral/multispectral imaging also confirmed the strong green fluorescence (*, right square in inset d) from *P. aruginosa* (with little porphyrin fluorescence, yellow line in inset f) of FIG. 30 compared to *E. coli* (left square in inset d) where significant porphyrin red fluorescence was detected. Insets e) and g) of FIG. 30 show the color-coded hyperspectral/multispectral images corresponding to *P. aeruginosa* and *E. coli*, respectively, from the meat surface after 2 days of growth (incubated at 37° C.); and insets f) and h) of FIG. 30 show the corresponding color-coded fluorescence spectroscopy. In inset i) of FIG. 30, excitation-emission matrices (EEM) were also measured for the various bacterial species in solution, demonstrating the ability to select the optimum excitation and emission wavelength bandwidths for use with optical filters in the imaging device. The EEM for *E. coli* shows strong green fluorescence as well as significant red fluorescence from endogenous bacterial porphyrins (arrow).

This example shows that bacteria emit green and red autofluorescence, with some species (e.g., *Pseudomonas aeruginosa*) producing more of the former. *Escherichia coli* produced significant red autofluorescence from endogenous porphyrins. Such intrinsic spectral differences between bacterial species are significant because it may provide a means of differentiating between different bacterial species using autofluorescence alone. Excitation-emission matrices (EEMs) were also measured for each of the bacterial species used in these pilot studies, which confirmed that under violet/blue light excitation, all species produced significant green and/or red fluorescence, the latter being produced by porphyrins. Spectral information derived from excitation-emission matrices may aid in optimizing the selection of excitation and emission wavelength bandwidths for use with optical filters in the imaging device to permit inter-bacterial species differentiating ex vivo and in vivo. In this way, the device may be used to detect subtle changes in the presence and amount of endogenous connective tissues (e.g. collagens and elastins) as well as bacteria and/or other microorganisms, such as yeast, fungus and mold within wounds and surrounding normal tissues, based on unique autofluorescence signatures of these biological components.

This device may be used as an imaging and/or monitoring device in clinical microbiology laboratories. For example, the device may be used for quantitative imaging of bacterial colonies and quantifying colony growth in common microbiology assays. Fluorescence imaging of bacterial colonies may be used to determine growth kinetics.

Imaging of Blood in Wounds

Angiogenesis, the growth of new blood vessels, is an important natural process required for healing wounds and for restoring blood flow to tissues after injury or insult. Angiogenesis therapies, which are designed to "turn on" new capillary growth, are revolutionizing medicine by providing a unified approach for treating crippling and life-threatening conditions. Angiogenesis is a physiological process required for wound healing. Immediately following injury, angiogenesis is initiated by multiple molecular signals, including hemostatic factors, inflammation, cytokine growth factors, and cell-matrix interactions. New capillaries proliferate via a cascade of biological events to form granulation tissue in the wound bed. This process may be sustained until the terminal stages of healing, when angiogenesis is halted by diminished levels of growth factors, resolution of inflammation, stabilized tissue matrix, and endogenous inhibitors of angiogenesis. Defects in the angiogenesis pathway impair granulation and delay healing, and these are evident in chronic wounds. By illuminating the tissue surface with selected narrow wavelength bands (e.g., blue, green and red components) of light or detecting the reflectance of white light within several narrow bandwidths of the visible spectrum (e.g., selected wavelengths of peak absorption from the blood absorption spectrum of white light), the device may also be used to image the presence of blood and microvascular networks within and around the wound, including the surrounding normal tissue, thus also revealing areas of erythema and inflammation.

Figure 31:
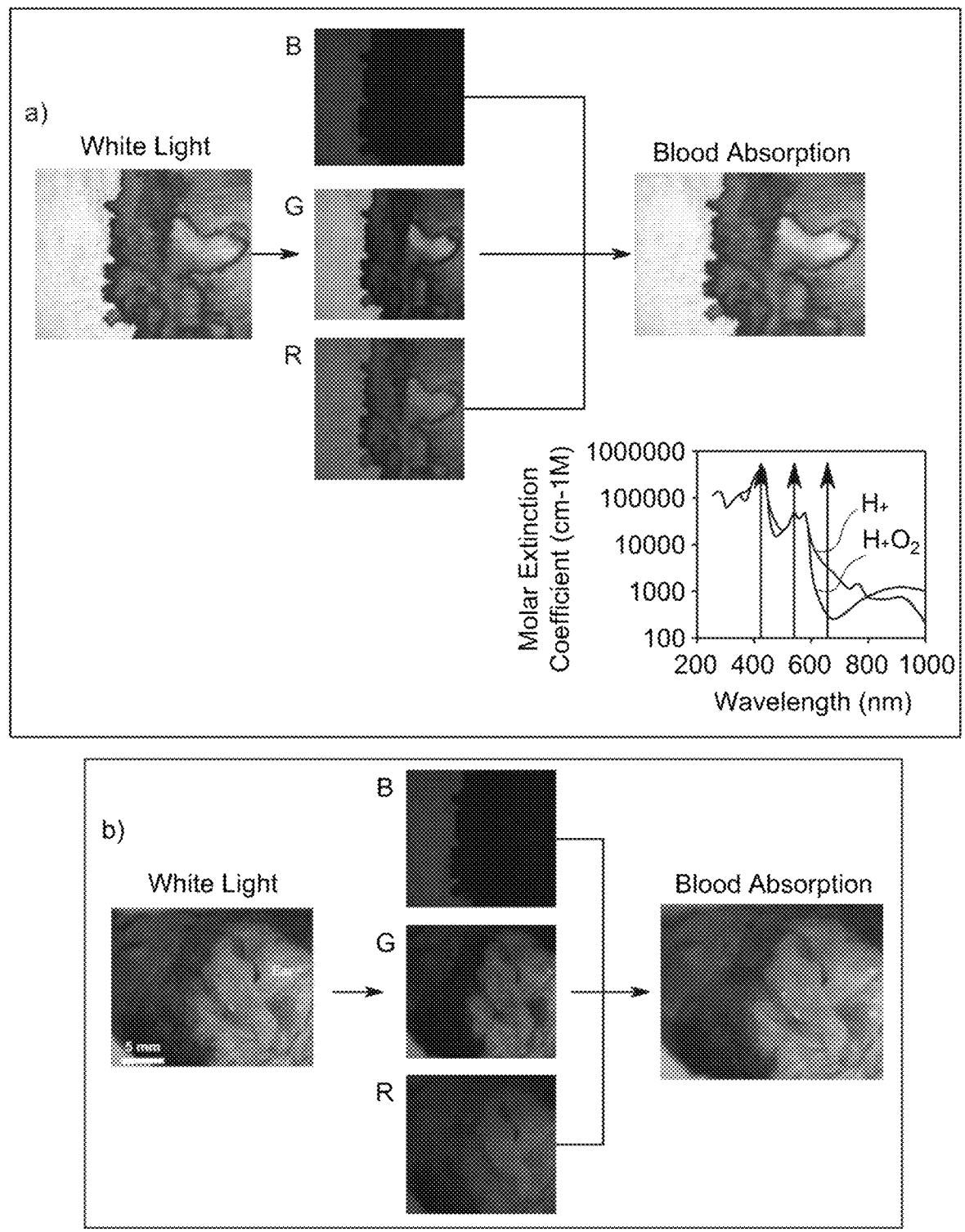
FIG. 31 shows images demonstrating use of a device for fluorescence-based monitoring in accordance with the present disclosure for imaging of blood and microvasculature.

Reference is now made to FIG. 31. In this example, a device in accordance with the present disclosure may use individual optical filters (e.g., 405 nm, 546 nm, 600 nm, +/−25 nm each) in order to demonstrate the possibility of imaging blood and microvasculature in wounds. White light images of a wound may be collected with the device and then the device, equipped with a triple band-pass filter (e.g., 405 nm, 546 nm, 600 nm, +/−25 nm each), placed in front of the imaging detector may image the separate narrow bandwidths of blue (B), green (G), and red (R) reflected light components from the wound. These wavelength bands may be selected based on the peak absorption wavelengths of blood, containing both oxygenated and deoxygenated hemoglobin, in the visible light wavelength range. The resulting images may yield the relative absorption, and thus reflectance, of visible light by blood in the field of view. The resulting 'blood absorption' image yields a high contrast image of the presence of blood and/or microvascular networks in the wound and surrounding normal tissues. The clinician may select the appropriate optical filter set for use with the device to obtain images of blood and/or microvascular distribution within the wound and then combine this information with one or both of autofluorescence imaging and imaging with exogenous contrast agents. This may provide a comprehensive information set of the wound and surrounding normal tissues at the morphological, topographical, anatomical, physiological, biological and molecular levels, which currently may not be possible within conventional wound care practice.

FIG. 31 shows examples of the device used for imaging of blood and microvasculature in wounds. The device was used to image a piece of filter paper stained with blood (inset a) of FIG. 31) and the ear of a mouse during surgery (inset b) of FIG. 31). White light images were collected of each specimen using the imaging device, in non-fluorescence mode, and then the device was equipped with a triple band-pass filter placed in front of the imaging detector (405 nm, 546 nm, 600 nm, +/−25 nm each) to image the separate narrow bandwidths of blue (B), green (G), and red (R) reflected light components from the specimens. These wavelength bands were selected based on the peak absorption wavelengths of blood in the visible light wavelength range. Inset a) shows the absorption spectral profile for oxy- and deoxygenated hemoglobin in blood. This shows that when using a simple multiband transmission filter, it is possible to combine the three B, G, R images into a single 'white light equivalent' image that measures the relative absorption of light by blood in the field of view. The resulting 'blood absorption' image yields a high contrast image of the presence of blood containing both oxy- and deoxygenated hemoglobin. The device may also be used with narrower bandwidth filters to yield higher contrast images of blood absorption in wounds, for example.

The regulation of angiogenesis over time during wound repair in vivo has been largely unexplored, due to difficulties in observing events within blood vessels. Although initial tests using an imaging device in accordance with the present disclosure were exploratory, simple modification of the device may allow longitudinal imaging of dynamic changes in blood supply and microvascular networks during the wound healing process in vivo.

In general, devices in accordance with the present disclosure may be used to image and/or monitor targets such as a skin target, an oral target, an ear-nose-throat target, an ocular target, a genital target, an anal target, and any other suitable targets on a subject.

Use in Clinical Care

Although current wound management practice aims to decrease the morbidity and mortality of wounds in patients, a limitation is the availability of health care resources. The potential of incorporating the technology of telemedicine into wound care needs is currently being explored. Wound care is a representation of the care of chronic and debilitating conditions that require long-term specialized care. The major effect of improved living conditions and advances in health care globally has led to people living longer. Therefore, the percentage of worlds' elderly and those with chronic medical conditions that would require medical attention is rising. With the escalating costs of health care, and the push of the industry towards outpatient care, this is a part of the health care crisis that is demanding immediate attention.

Devices in accordance with the present disclosure may provide biologically-relevant information about wounds and may exploit the emerging telemedicine (e.g., E-health) infrastructure to provide a solution for mobile wound care technology and may greatly impact wound health care treatment. Wound care accounts for a large percentage of home visits conducted by nurses and health care workers. Despite best practices some wounds do not heal as expected and require the services of a clinical specialist. The exemplary devices described herein may enable access to specialized clinical resources to help treat wounds from the convenience of the patient's home or chronic care facility, which decreases travel time for clients, increases availability to clinical wound specialists, and may reduce costs to the health care system.

Different uses of the imaging devices have been discussed for wound assessment, monitoring and care management. The devices may be used to detect and monitor changes in connective tissues (e.g., collagen, elastin) and blood/vascular supply during the wound healing process, monitor tissue necrosis and exudate in wounds based on fluorescence, detect and diagnose wound infections including potentially indicating critical 'clinically significant' categories of the presence of bacteria or micro-organisms (e.g., for detecting contamination, colonization, critical colonization and infection) at the surface and deep within wounds, provide topographic information of the wound, and identify wound margins and surrounding normal tissues. Tissue fluorescence and reflectance imaging data may be 'mapped' onto the white light images of the wound thereby permitting visualization within the wound and the surrounding normal tissues of essential wound biochemical and photobiological (e.g., fluorescence) information, which has not been possible to date. Real-time imaging of wounds may be performed over time to monitor changes in wound healing, and to potentially monitor the effectiveness of treatments by providing useful information about underlying biological changes that are occurring at the tissue/cellular level (e.g., matrix remodeling, inflammation, infection and necrosis). This may provide quantitative and objective wound information for detection, diagnosis and treatment monitoring in patients. In particular, such devices may be used to monitor and/or track the effectiveness of therapy at a biological level (e.g., on a bacterial level), which may provide more information than monitoring only the macroscopic/morphological appearance using white light.

The devices may provide real-time non-invasive image-guided biopsy targeting, clinical procedural guidance, tissue characterization, and may enable image-guided treatment using conventional and emerging modalities (e.g., PDT). In addition, use of the imaging devices may be used to correlate critical biological and molecular wound information obtained by fluorescence (e.g., endogenous tissue autofluorescence and/or administration of exogenous molecular-biomarker targeted fluorescence contrast agents) with existing and emerging clinical wound care assessment and treatment guides, such as the NERDS and STONES guidelines proposed by Sibbald et al. (Sibbald et al. Increased Bacterial Burden and Infection: The Story of NERDS and STONES. ADV SKIN WOUND CARE 2006; 19:447-61). The fluorescence imaging data obtained with the devices may be used to characterize, spatially and spectrally, bacterial balance and burden at the superficial and deep levels of wounds. The devices may provide real-time non-invasive image-guided biopsy targeting, clinical procedural guidance, tissue characterization, and may enable image-guided treatment using conventional and emerging treatment modalities (e.g., photodynamic therapy, PDT). The devices may be used within the clinical setting and integrated into conventional clinical wound care regimens, and may have a distinct role in areas of infectious diseases. It should be noted as well that such devices may also be used for real-time analysis, monitoring and care for chronic and acute wounds in animals and pets, via conventional veterinary care.

Devices in accordance with the present disclosure may allow real-time wound healing assessment for a large patient cohort base. In particular, elderly people, diabetics, immuno-suppressed and immobilized individuals have an increased incidence of chronic wounds and other dermal afflictions that result from poor circulation and immobility, e.g. pressure ulcers such as bed sores, venous stasis ulcers, and diabetic ulcers. These chronic conditions greatly increase the cost of care and reduce the patient's quality of life. As these groups are growing in number, the need for advanced wound care products will increase. Such devices may impact patient care by allowing a cost-effective means of monitoring chronic and acute wounds in a number of settings, including hospitals, ambulatory clinics, chronic care facilities, in-home-visit health care, emergency rooms and other critical areas in health care facilities. Further, such 'handheld' and portable imaging devices may be easily carried and used by nursing and ambulance staff. Early identification of scarring, which is related to connective tissue production and re-modeling of the wound, and bacterial infections may be detected and treated appropriately, something that is currently difficult. In addition, recent developments in advanced wound-care products including multiple dressing types (e.g., film, hydrocolloid, foam, antimicrobial, alginate, non-adherent, impregnated), hydrogels, wound cleansers and debriding agents, tissue engineered products (e.g., skin replacements, substitutes, and tissue-engineered products such as synthetic polymer-based biological tissue and growth factors), wound cleansers, pharmacological products, and physical therapies may also benefit from the device developed here as it may allow image-based longitudinal monitoring of the effectiveness of such treatments. Physical therapies may include hydrotherapy, electrical stimulation, electromagnetic stimulation devices, ultraviolet therapy, hyperbaric oxygen therapy, ultrasound devices, laser/light emitting diode (LED) devices, and wound imaging/documentation. Additional therapies may include, for example, antibiotics, wound debridement, application of wound dressings, and wound cleaning.

Wound tissue analysis is typically required for the assessment of the healing of skin wounds. Percentage of the granulation tissue, fibrin and necrosis in the wound, and their change during treatment may provide useful information that may guide wound treatment. Image analysis may include advanced statistical pattern recognition and classification algorithms to identify individual pixels within the fluorescence wound images collected with the device based on the optical information of the wound and surrounding normal tissue. Thus, image analysis may allow wound images to be mapped into various components of the wound, including total wound area, epithelialization, granulation, slough, necrotic, hypergranulation, infected, undermining, and surrounding tissue margins. This has an added advantage of providing relatively rapid determination of wound healing rates, as well as informing guide patient management decisions.

Figure 32:
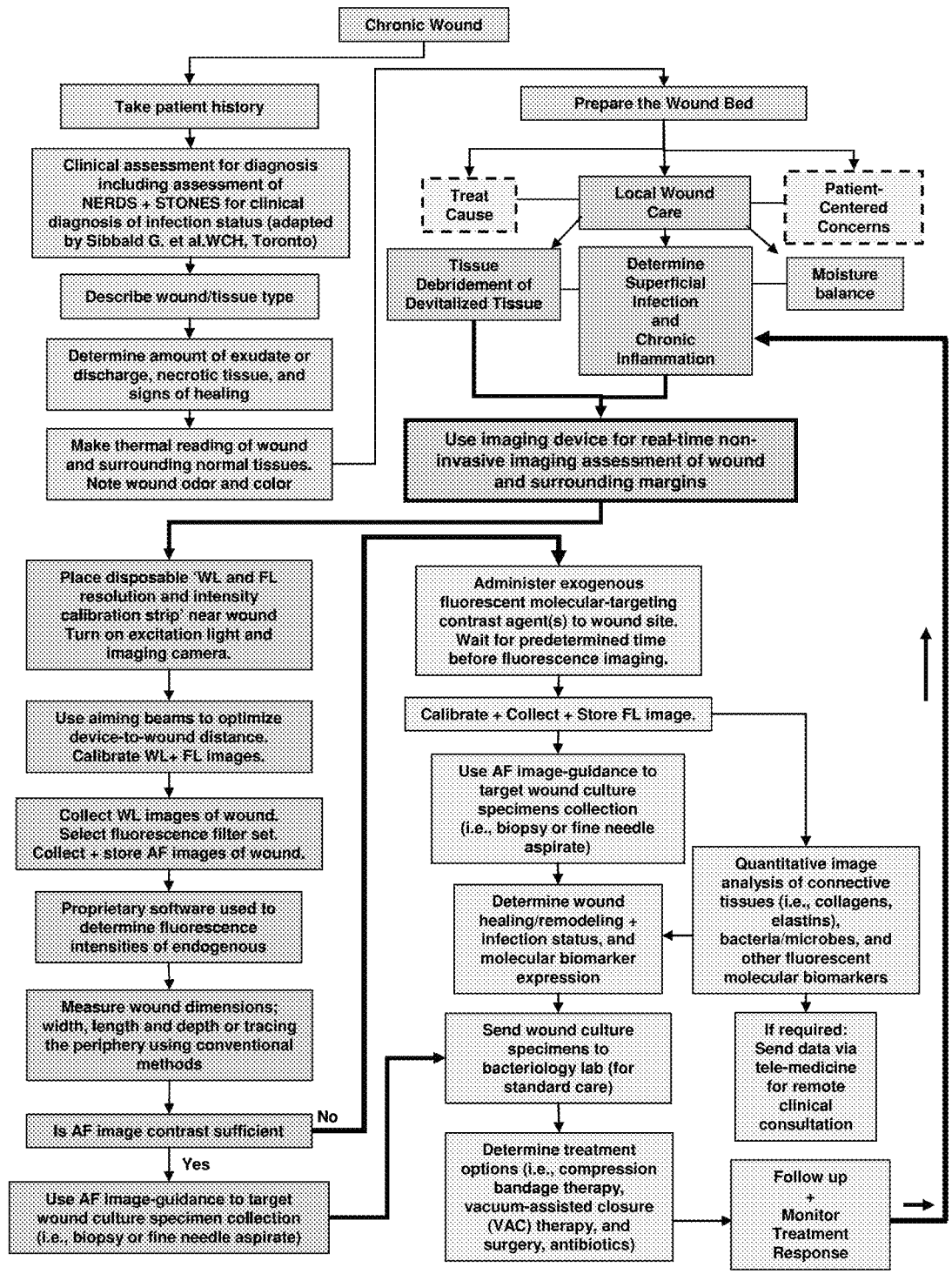
FIG. 32 is a flowchart illustrating the management of a chronic wound using a device for fluorescence-based monitoring in accordance with the present disclosure.

FIG. 32 illustrates the projected management workflow for an exemplary imaging device in a clinical wound care setting. The device may be easily integrated into routine wound assessment, diagnosis, treatment and longitudinal monitoring of response, and may provide critical biological and molecular information of the wound in real-time for rapid decision-making during adaptive interventions.

This device may be easily integrated into existing healthcare computer infrastructures (e.g., desktop and pocket PCs used by a growing number of physicians or other health care professionals) for longitudinal image cataloguing for patient wound management within the conventional clinical environment. The wireless receiving and transmission of data capabilities of the device may allow monitoring of wound care and healing remotely through existing and future wireless telemedicine infrastructure. The device may be used to transfer essential medical data (e.g., wound health status) via the internet or over wireless services, such as cellular telephone, PDA or Smartphone services, to remote sites which may permit remote medical interventions, with a further utility in military medical applications for battlefield wound management. The device may allow real-time surface imaging of wound sites and may be easily carried by point-of-care personnel in clinical settings. Using cost-effective highly sensitive commercially available digital imaging devices, such as digital cameras, cellular phones, PDAs, laptop computers, tablet PCs, webcams, and Smart phones, etc. as the image capture or recording component, the device may offer image-based documentation of wound healing and tracking of treatment effectiveness. Also, this technology may be adapted to also function in 'wireless' mode to permit remote medical interventions by potentially adapting it for use with high-resolution digital cameras embedded in commercially-available cellular telephones.

By using web-based telemedicine and remote medical monitoring infrastructure, the imaging device may be integrated into a 'store-and-forward' concept of wound assessment systems. In addition to providing digital images, such a system may present a comprehensive set of clinical data that meet the recommendations of clinical practice guidelines. The presently-disclosed devices may integrate into a computer-based wound assessment system (e.g., with image analysis software) to be used by a health care facility to enhance existing clinical databases and support the implementation of evidence—based practice guidelines. Such an integrated telemedicine infrastructure may be used for monitoring patients at home or in long-term-care facilities, who may benefit from routine monitoring by qualified clinicians but currently do not have access to this care. These devices may be further developed into a portable handheld pointof-care diagnostic system, which may represent a major advance in detecting, monitoring, treating, and preventing infectious disease spread in the developed and developing worlds. This knowledge may significantly improve the diagnostic tools available to practitioners who treat chronic wounds in settings where quantitative cultures are inaccessible.

Devices in accordance with the present disclosure may allow digital imaging with optical and digital zooming capabilities (e.g., those embedded in commonly available digital imaging devices). Still or video image quality may be in 'high-definition' format to achieve high spatial resolution imaging of the tissue surface. Images may be recorded as still/freeze frame and/or in video/movie format and printed using standard imaging printing protocols which do (e.g., connected via USB) or do not (e.g., PictBridge) require a personal computer. The images/video data may be transferred to a personal computer for data archival storage and/or image viewing and/or analysis/manipulation. Such devices may also transfer data to a printer or personal computer using wired or wireless capabilities (e.g., Bluetooth). Visualization may be performed on the handheld device screen and/or in addition to simultaneous viewing on a video screen/monitor (e.g., head-mounted displays and glasses) using standard output video cables. These devices may display, in combination or separately, optical wavelength and fluorescence/reflectance intensity information with spatial dimensions of the imaged scene to allow quantitative measurements of distances (e.g., monitoring changes tissue morphology/topography) over time. The devices may also allow digital image/video storage/cataloguing of images and related patient medical data, for example using dedicated software with imaging analysis capabilities and/or diagnostic algorithms.

Image Analysis

Figure 33:
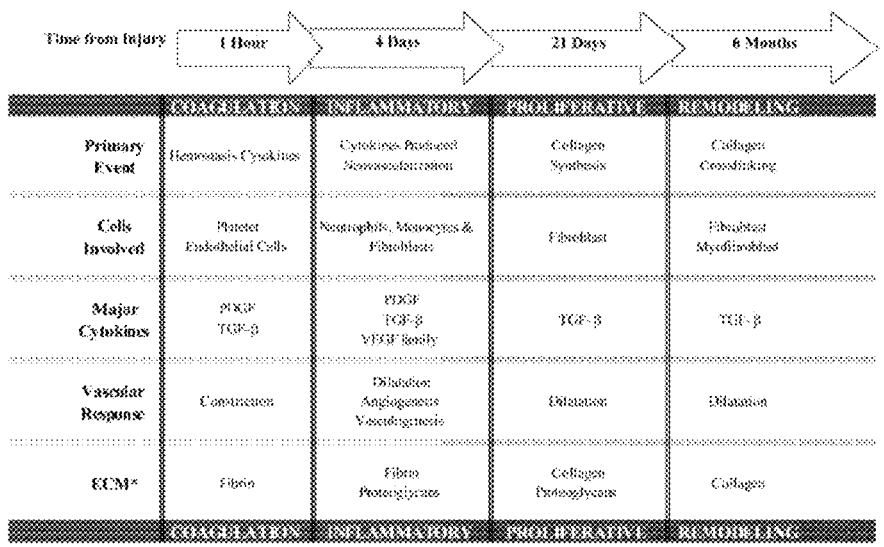
FIG. 33 illustrates the phases of wound healing with time.

Image analysis may be used together with the exemplary devices of the present disclosure to quantitatively measure fluorescence intensities and relative changes in multiple fluorescence spectra (e.g., multiplexed imaging) of the exogenous optical molecular targeting probes in the wound and surrounding normal tissues. The biodistributions of the fluorescent probes may be determined based on the fluorescence images collected and these may be monitored over time between individual clinical wound imaging sessions for change. By determining the presence and relative changes in abundance quantitatively, using the devices, of each and all of the spectrally-unique fluorescent probes, the clinical operator may determine in real-time or near real-time the health and/or healing status and response to treatment over time of a given wound, for example by using a look-up table in which specific tissue, cellular and molecular signals are displayed in correlation to wound health, healing and response status, an example of which is shown in FIG. 33. This may permit the clinician to determine whether a wound is healing based on biological and molecular information which may not be possible otherwise with existing technologies. Furthermore, the presence and abundance of bacteria/microorganisms and their response to treatment may offer a means to adapt the therapy in real-time instead of incurring delays in response assessment with conventional bacteriological testing of wound cultures.

Image analysis techniques may be used to calibrate the initial or first images of the wound using a portable fluorescent standard placed within the field of view during imaging with a device. The image analysis may also permit false or pseudo color display on a monitor for differentiating different biological (e.g., tissue, cellular, and molecular) components of the wound and surrounding normal tissues including those biomarkers identified by autofluorescence and those identified by the use of exogenous targeted or untargeted fluorescence/absorption contrast agents.

Figure 35:
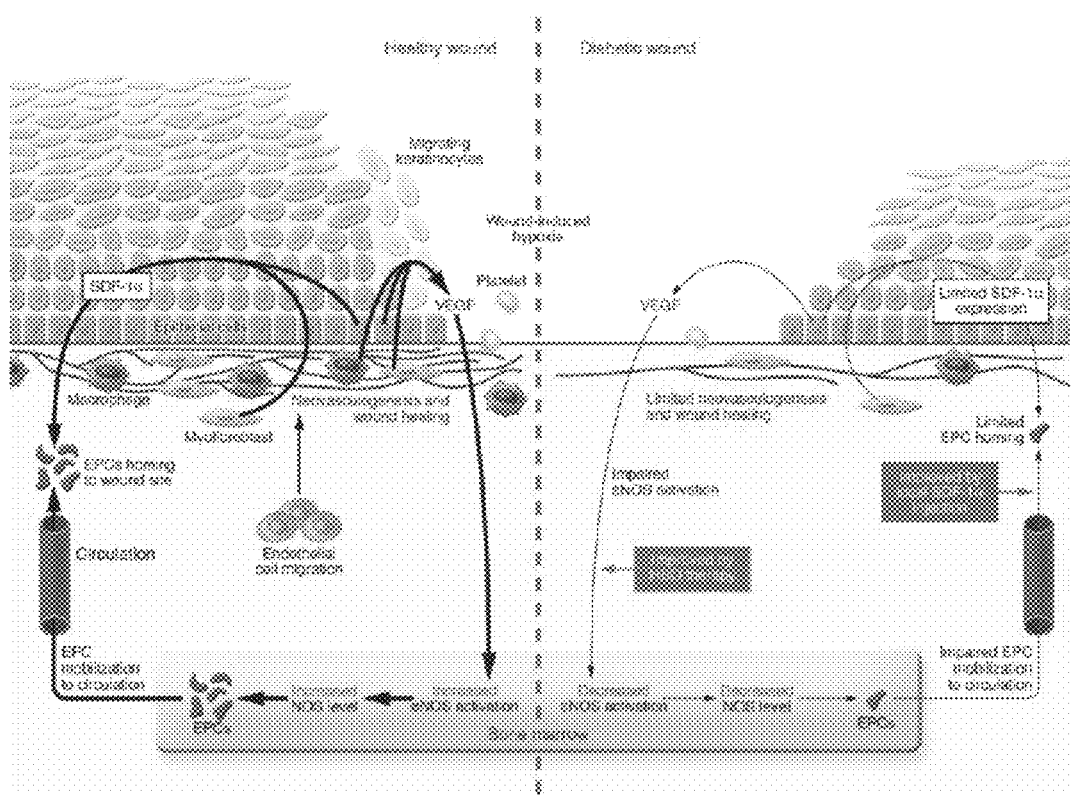
FIG. 35 is a diagram comparing a healthy wound to a chronic wound.

Examples of such biomarkers are listed in FIG. 34 and illustrated in FIG. 35. In FIG. 35, the diagram shows mechanisms of wound healing in healthy people versus people with diabetic wounds. In healthy individuals (left side of FIG. 35), the acute wound healing process is guided and maintained through integration of multiple molecular signals (e.g., in the form of cytokines and chemokines) released by keratinocytes, fibroblasts, endothelial cells, macrophages, and platelets. During wound-induced hypoxia, vascular endothelial growth factor (VEGF) released by macrophages, fibroblasts, and epithelial cells induces the phosphorylation and activation of eNOS in the bone marrow, resulting in an increase in NO levels, which triggers the mobilization of bone marrow EPCs to the circulation. For example, the chemokine SDF-1αpromotes the homing of these EPCs to the site of injury, where they participate in neovasculogenesis. In a murine model of diabetes (right side of FIG. 35), eNOS phosphorylation in the bone marrow is impaired, which directly limits EPC mobilization from the bone marrow into the circulation. SDF-1α expression is decreased in epithelial cells and myofibroblasts in the diabetic wound, which prevents EPC homing to wounds and therefore limits wound healing. It has been shown that establishing hyperoxia in wound tissue (e.g., via HBO therapy) activated many NOS isoforms, increased NO levels, and enhanced EPC mobilization to the circulation. However, local administration of SDF-1α was required to trigger homing of these cells to the wound site. These results suggest that HBO therapy combined with SDF-1α administration may be a potential therapeutic option to accelerate diabetic wound healing alone or in combination with existing clinical protocols.

Pre-assigned color maps may be used to display simultaneously the biological components of the wound and surrounding normal tissues including connective tissues, blood, microvascularity, bacteria, microorganisms, etc. as well as fluorescently labeled drugs/pharmacological agents. This may permit visualization in real-time or near real-time (e.g., less than 1 minute) of the health, healing and infectious status of the wound area.

The image analysis algorithms may provide one or more of the following features:

Patient Digital Image Management
    Integration of a variety of image acquisition devices
    Records all imaging parameters including all exogenous fluorescence contrast agents
    Multiple scale and calibrations settings
    Built-in spectral image un-mixing and calculation algorithms for quantitative determination of tissue/bacterial autofluorescence and exogenous agent fluorescence signals
    Convenient annotation tools
    Digital archiving
    Web publishing Basic Image Processing and Analysis
    Complete suite of image processing and quantitative analysis functions Image stitching algorithms will allow stitching of a series of panoramic or partially overlapping images of a wound into a single image, either in automated or manual mode.
    Easy to use measurement tools
    Intuitive set up of processing parameters
    Convenient manual editor Report Generation
    Powerful image report generator with professional templates which may be integrated into existing clinical report infrastructures, or telemedicine/e-health patient medical data infrastructures. Reports may be exported to PDF, Word, Excel, for example.
Large Library of Automated Solutions
    Customized automated solutions for various areas of wound assessment including quantitative image analysis.

Although image analysis algorithm, techniques, or software have been described, this description also extends to a computing device, a system, and a method for carrying out this image analysis.

Image-Guidance

Devices in accordance with the present disclosure may also be useful for providing fluorescent image-guidance, for example in surgical procedures, even without the use of dyes or markers. Certain tissues and/or organs may have different fluorescent spectra (e.g., endogenous fluorescence) when viewed using the imaging device, or example under certain excitation light conditions.

Figure 36:
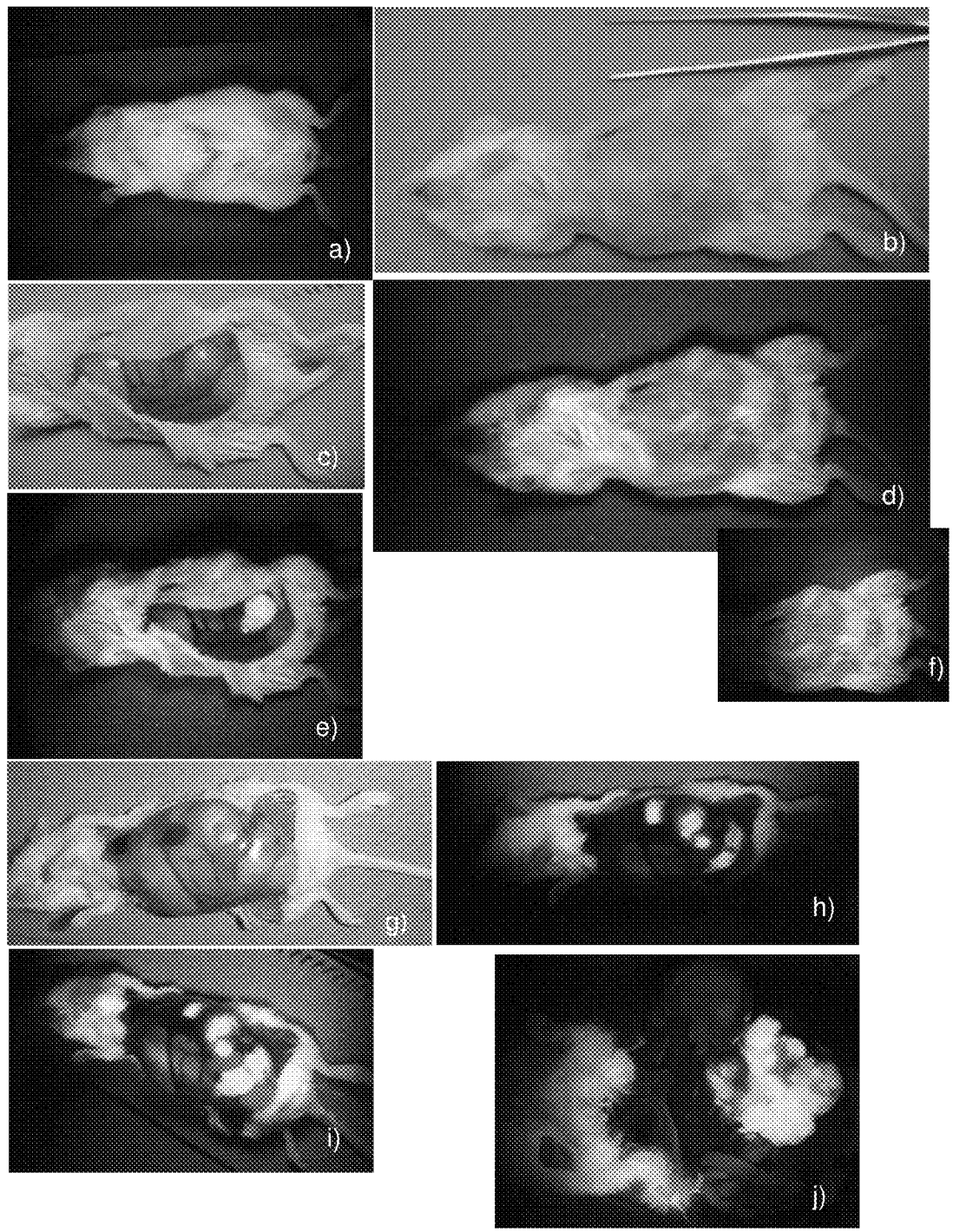
FIG. 36 shows images demonstrating the use of a device for fluorescence-based monitoring in accordance with the present disclosure in imaging a mouse model.

FIG. 36 demonstrates the usefulness of a device in accordance with the present disclosure for fluorescence imaging-assisted surgery. With the aid of fluorescence imaging using the device, different organs of a mouse model may be more clearly distinguishable than under white light. Insets b), c) and g) show the mouse model under white light. Insets a), d)-f), and h)-j) of FIG. 36 show the mouse model as imaged with the device.

Figure 37:
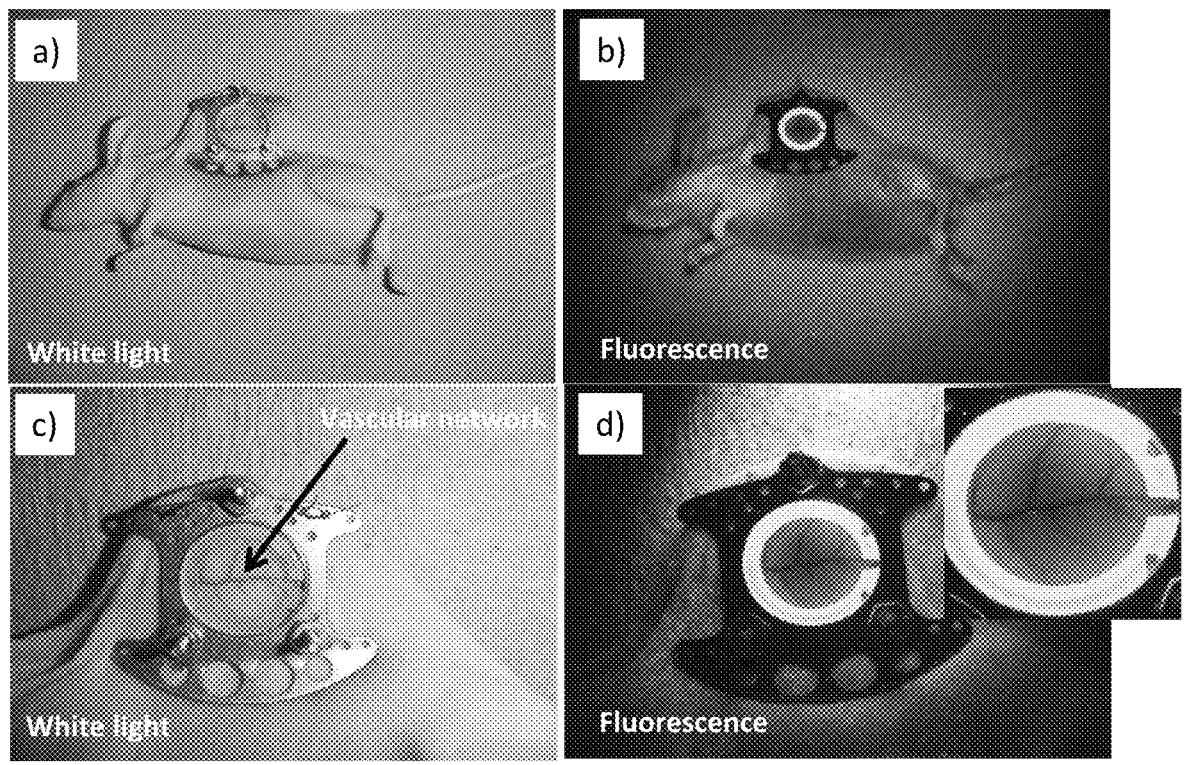
FIG. 37 shows an example of the use of a device for fluorescence-based monitoring in accordance with the present disclosure for imaging small animal models.

FIG. 37 shows an example of the use of a device in accordance with the present disclosure for imaging small animal models. Here, the mouse dorsal skin-fold window chamber is imaged under white light (insets a) and c) of FIG. 37) and fluorescence (insets b) and d) of FIG. 37). Note the high-resolution white light and fluorescence images obtained by the device. The feet and face appear bright red fluorescent due to endogenous autofluorescence from the cage bedding and food dust materials. (405 nm excitation; 490-550 nm and >600 nm emission channels).

Bioengineered Skin

Several bioengineered skin products or skin equivalents have become available commercially for the treatment of acute and chronic wounds, as well as burn wounds. These have been developed and tested in human wounds. Skin equivalents may contain living cells, such as fibroblasts or keratinocytes, or both, while others are made of acellular materials or extracts of living cells. The clinical effect of these constructs is 15-20% better than conventional 'control' therapy, but there is debate over what constitutes an appropriate control. Bioengineered skin may work by delivering living cells which are known as a 'smart material' because they are capable of adapting to their environment. There is evidence that some of these living constructs are able to release growth factors and cytokines. Exogenous fluorescent molecular agents may be used in conjunction with such skin substitutes to determine completeness of engraftment as well as biological response of the wound to the therapy. The healing of full-thickness skin defects may require extensive synthesis and remodeling of dermal and epidermal components. Fibroblasts play an important role in this process and are being incorporated in the latest generation of artificial dermal substitutes.

The exemplary imaging devices described herein may be used to determine the fate of fibroblasts seeded in skin substitute and the influence of the seeded fibroblasts on cell migration and dermal substitute degradation after transplantation to a wound site. Wounds may be treated with either dermal substitutes seeded with autologous fibroblasts or acellular substitutes. Seeded fibroblasts, labeled with a fluorescent cell marker, may then be detected in the wounds with a fluorescence imaging device and then quantitatively assessed using image analysis, for example as described above.

Polymer-Based Therapeutic Agents

There are a number of commercially available medical polymer products made for wound care. For example, Rimon Therapeutics produces Theramers™ (www.rimontherapeutics.com) which are medical polymers that have biological activity in and of themselves, without the use of drugs. Rimon Therapeutics produces the following wound care products, which can be made to be uniquely fluorescent, when excited by 405 nm excitation light: Angiogenic Theramer™, which induces new blood vessel development (i.e., angiogenesis) in wounds or other ischemic tissue; MI Theramer™, which inhibits the activity of matrix metalloproteases (MMPs), a ubiquitous group of enzymes that are implicated in many conditions in which tissue is weakened or destroyed; AM Theramer™, a thermoplastic that kills gram positive and gram negative bacteria without harming mammalian cells; and ThermaGel™, a polymer that changes from a liquid to a strong gel reversibly around body temperature. These can each be made to be fluorescent by addition of fluorescent dyes or fluorescent nanoparticles selected to be excited, for example, at 405 nm light with longer wavelength fluorescence emission.

By using the exemplary imaging devices of the present disclosure, the application of such fluorescent polymer agents may be guided by fluorescent imaging in real-time. This may permit the Theramer agent to be accurately delivered/applied (e.g., topically) to the wound site. Following application of the agent to the wound, a fluorescent imaging device may then be used to quantitatively determine the therapeutic effects of the Theramers on the wound as well as track the biodistribution of these in the wound over time, in vivo and non-invasively. It may also be possible to add a molecular beacon, possibly having another fluorescent emission wavelength, to the MI Theramer™ that can fluoresce in the presence of wound enzymes (e.g., MMPs), and this may indicate in real-time the response of the wound to the MI Theramer™. It may be possible to use one fluorescence emission for image-guided Theramer application to the wound site and another different fluorescence emission for therapeutic response monitoring, and other fluorescence emissions for other measurements. The relative effectiveness of MMP inhibition and antimicrobial treatments may be determined simultaneously over time. Using image analysis, real-time comparison of changes in fluorescence of these signals in the wound may be possible. This adds a quantitative aspect to the device and adds to its clinical usefulness.

It should be noted that other custom bio-safe fluorescence agents may be added to the following materials which are currently used for wound care. The fluorescent material may then be imaged and monitored using the disclosed devices.
    Moist Wound Dressings: This provides a moist conducive environment for better healing rates as compared to traditional dressings. The primary consumer base that manufacturers target for these dressings is people over the age of 65 years, suffering from chronic wounds such as pressure ulcers and venous stasis ulcers. Those suffering from diabetes and as a result, developed ulcers form a part of the target population.
    Hydrogels: This adds moisture to dry wounds, creating a suitable environment for faster healing. Their added feature is that they may be used on infected wounds. These are also designed to dry to lightly exudative wounds.

Hydrocolloid Dressings: Hydrocolloids seal the wound bed and prevent loss of moisture. They form a gel upon absorbing exudates to provide a moist healing environment. These are used for light to moderately exudative wounds with no infection.

Alginate Dressings: These absorb wound exudates to form a gel that provides a moist environment for healing. They are used mainly for highly exudative wounds.

Foam Dressing: These absorb wound drainage and maintain a moist wound surface, allowing an environment conducive for wound healing. They are used on moderately exudative wounds.

Transparent Film Dressing: These are non-absorptive, but allow moisture vapor permeability, thereby ensuring a moist wound surface. They are intended for dry to lightly exudative wounds. Examples include alginate foam transparent film dressings.

Antimicrobials: These provide antibacterial action to disinfect the wound. Of particular interest is the use of nanocrystalline silver dressings. The bio burden, particularly accumulated proteases and toxins released by bacteria that hampers healing and causes pain and exudation, is reduced significantly with the extended release of silver.

Active Wound Dressings: These comprise highly evolved tissue engineered products. Biomaterials and skin substitutes fall under this category; these are composed entirely of biopolymers such as hyaluronic acid and collagen or biopolymers in conjunction with synthetic polymers like nylon. These dressings actively promote wound healing by interacting either directly or indirectly with the wound tissues. Skin substitutes are bioengineered devices that impersonate the structure and function of the skin.

Hyaluronic Acid: This is a natural component of the extra cellular matrix and plays a significant role in the formation of granular tissue, re-epithelialization and remodeling. It provides hydration to the skin and acts as an absorbent.

Other wound care products that may be imaged using the disclosed devices include Theramers, silver-containing gels (e.g., hydrogels), artificial skin, ADD stem cells, anti-matrix metalloproteinases, and hyaluronic acid. Fluorescent agents may be added to other products to allow for imaging using the devices. In some cases, the products may already be luminescent and may not require the addition of fluorescent agents.

The exemplary disclosed devices may be used also to monitor the effects of such treatments over time.

Cosmetic Applications

Device in accordance with the present disclosure may be used to image a patient's skin surface. For example, the device may be used to obtain images of the patient's skin by detecting autofluorescence produced by violet/blue light excitation of the skin surface. Red fluorescence from *P. acnes* may be easily detected in regions of the patient's face. *P. acnes* is the causative agent of acne vulgaris (i.e., pimples) and is a common resident of the pilosebaceous glands of the human skin. Furthermore, *P. acnes* is occult under white light visualization. The auto fluorescent images of the patient's skin may be obtained without the need of exogenous agents/drugs and demonstrate the capability of the device to detect bacteria in single skin pores.

Figure 39:
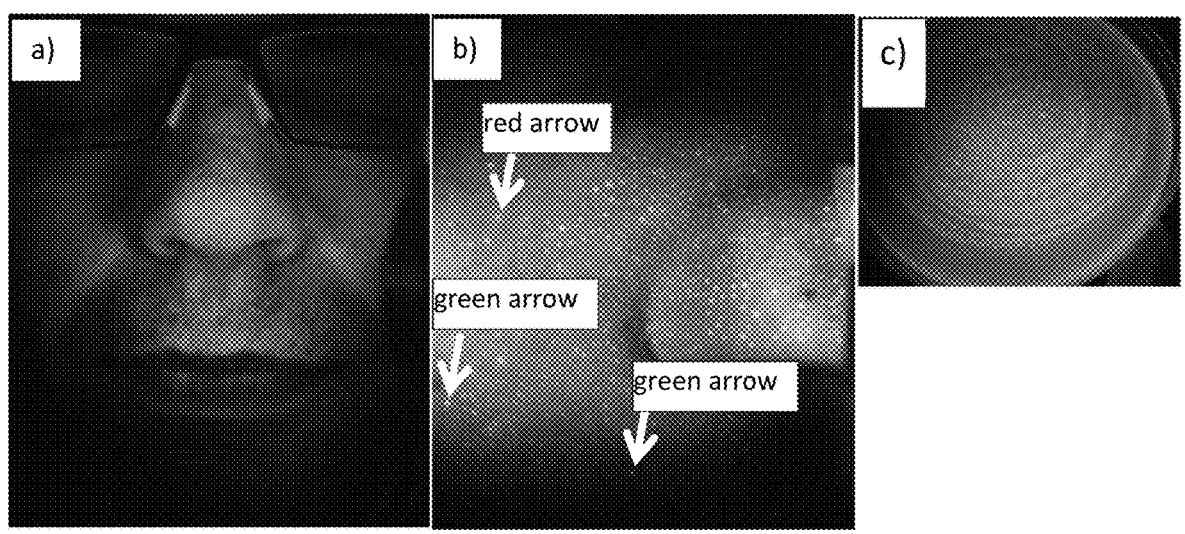
FIG. 39 shows an example of the use of a device for fluorescence-based monitoring in accordance with the present disclosure for imaging a skin surface.

FIG. 39 shows an example of the use of an imaging device in accordance with the present disclosure for real-time fluorescence detection of common bacterial flora on skin. Inset a) of FIG. 39 shows red fluorescence on and around the nose detected from *Propionibacterium acnes* (*P. acnes*) commonly found within skin pores. Inset b) shows that fluorescence imaging may also be used to detect and monitor more than one bacterial species on the skin at the same time, for example *Propionibacterium* acne appears as red fluorescent (red arrow) while *Pseudomonas Aeruginosa* appears bright green (green arrows). This data suggests the use of the device for distinguishing relative concentrations/levels of various bacterial species, determining their biodistributions on a body surface, and monitoring response to anti-bacterial treatments in dermatology and cosmetology applications. Inset c) of FIG. 39 shows an example of a fluorescence image of a culture grown on agar from a swab taken from normal skin on the nose of a healthy volunteer. Bacteriology results showed the presence of *Pseudomonas aeruginosa*.

Such a capability to image and document the presence and biodistribution of bacteria on the skin surface makes the device potentially useful in the dermatology and cosmetology fields. For example, fluorescence imaging may be performed prior to, during, and after application of dermatological treatment and/or pharmaceutical/cosmetic formulations (e.g., topical creams, drugs and other antibiotics, skin disinfecting agents, acne treatments, etc.) to the normal and abnormal skin conditions, including but not limited to scarring, hyper-pigmentation, acne, psoriasis, eczema, rashes, etc. Fluorescence/reflectance image-guided tattoo removal (e.g., using surgery or available laser treatments) may also be an option with the device.

Figure 40:
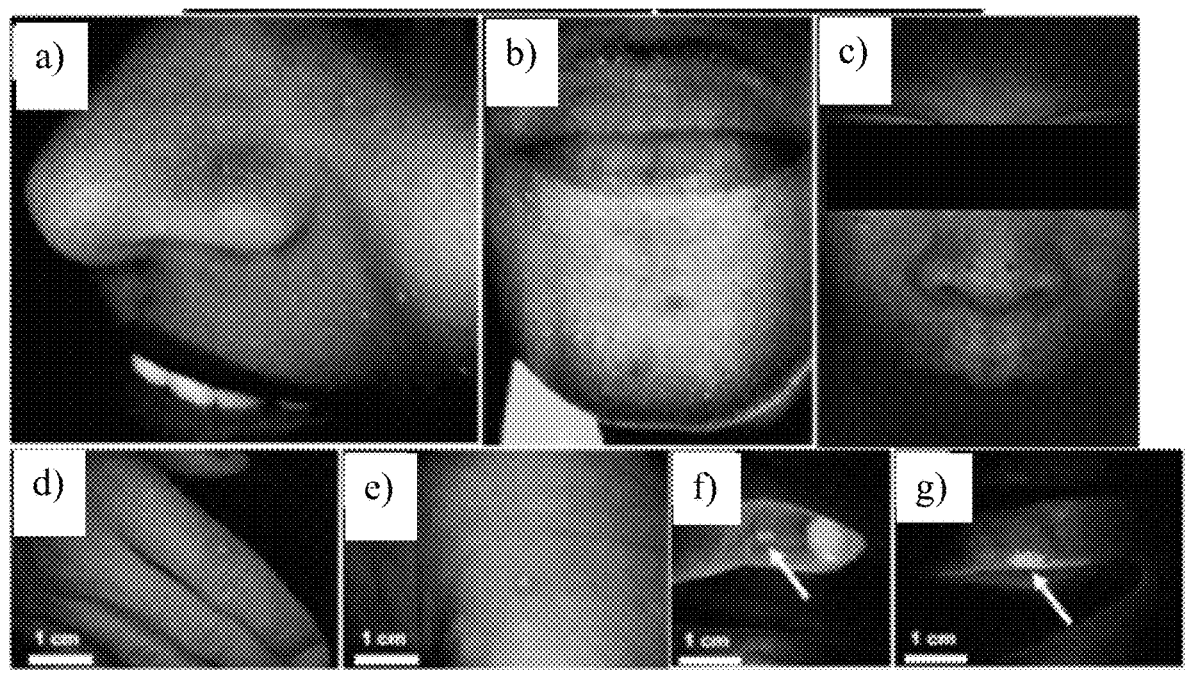
FIG. 40 shows images demonstrating additional exemplary uses of a device for fluorescence-based monitoring in accordance with the present disclosure for imaging a skin surface.

The device was also used to image minor cuts, scrapes, and abrasions on patients' skin and under violet/blue light. Tissue autofluorescence from connective tissue components (e.g., collagen and elastin) from the wound site and surrounding normal skin aided in detecting white light-occult changes in connective tissues during minor cutaneous wound healing (as seen in FIG. 40 insets f) and g)). In addition, the device may also serve as a practical, cost-effective and sensitive image-based tool for early detection of occult skin cancers and non-cancerous (i.e., benign) lesions in a non-invasive manner. The device may then be used to provide image-guidance for surgical excision of the lesions or for PDT. For the latter, fluorescence imaging may monitor PDT response and determine completeness of treatment over-time with multiple longitudinal image scans of the affected area. The device may be used in real-time for determining PDT photosensitizer localization and biodistribution and photobleaching, and this may be mapped onto the white light image of the area to be treated for anatomical comparison. Changes in the optical properties between normal and diseases or burned tissues may be detected using both then white light and fluorescence imaging capabilities of the device.

With reference now to FIG. 40 a device in accordance with the present disclosure was used to image various patient skin surfaces. In insets a)-c) of FIG. 40, the device was used to image the skin on patients' faces by detecting autofluorescence produced by violet/blue light excitation of the skin surface. Red fluorescence from *P. acnes* may easily be detected in regions of the face (inset (e) of FIG. 40). The device may be used to image and/or monitor the potential effects of dermatological interventions (e.g., topical creams, drugs and other antibiotics, etc.) on patients' skin. In insets d) and e) of FIG. 40, the device was also used to image minor cuts scrapes and abrasions on patients' skin, as well as psoriasis on a finger. Under violet/blue light, the device detected tissue autofluorescence from connective tissue components (e.g., collagen and elastin) from the wound site and surrounding normal skin to yield high-resolution images of subtle cutaneous lesions.

The devices may also be used to image, assess and longitudinally monitor the healing process in burns or determine the response of skin grafts or temporary skin substitutes in treatment of burn patients. The devices may also serve to detect and monitor late radiation-induced skin damage during treatment of patients with ionizing radiation.

Figure 41:
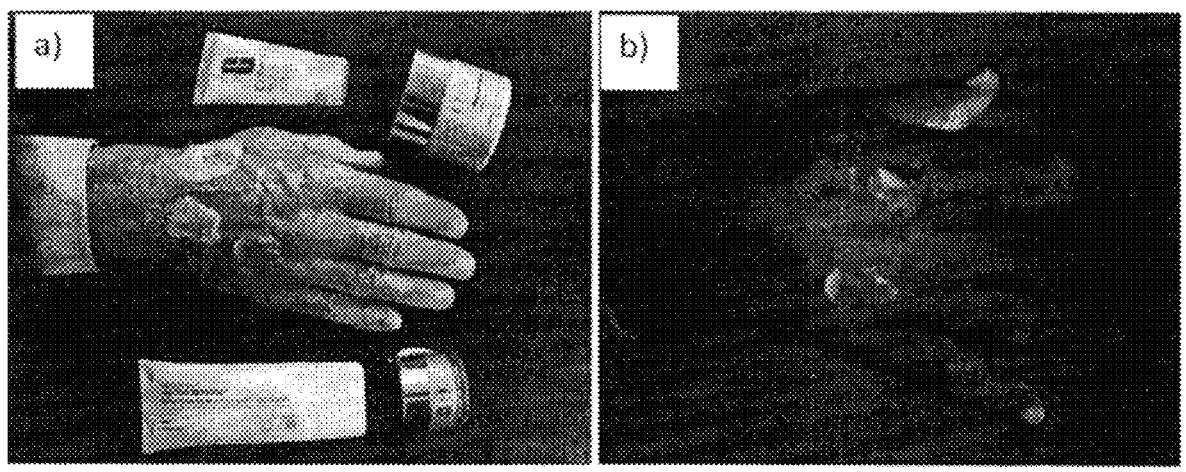
FIG. 41 shows an example of the use of a device for fluorescence-based monitoring in accordance with the present disclosure for imaging cosmetic or dermatological substances.

FIG. 41 shows an example of the use of a device in accordance with the present disclosure for imaging of cosmetic products. For example, four commercially available cosmetic creams are shown under white light (inset a) of FIG. 41) and fluorescence imaging modes (inset b) of FIG. 41), showing fluorescence contrast between the creams and the background skin. This data illustrates the potential use of the handheld imaging devices for use in imaging the presence and potential biological effects of cosmetic (e.g. rehydration of skin, collagen remodeling, repairing sunburn damage, skin exfoliation) and/or dermatological agents or drugs (405 nm excitation; 490-550 nm and >600 nm emission channels)).

Darkening Environment

In accordance with various embodiments of the present disclosure, it may be beneficial to use the disclosed imaging devices in a reduced lighting environment, such as a dimly lit environment or completely dark environment, to obtain FL images. In cases where ambient lighting cannot be dimmed, reduced sufficiently, or completely turned off, the optimal lighting conditions can be managed with optical accessories, such as a tent or drape. For example, when using the device of the present disclosure in a lit environment (such as in an operating room), a tent or drape may be used to create a darkened (dimly lit or complete dark) environment around the imaging target, for example around a limb of a patient. In some embodiments, the device includes a mechanism to allow for attachment of the tent or drape to the imaging device. The tent or drape may be disposable and may be packaged with the device as part of a system.

In some embodiments, the imaging device in accordance with the present disclosure may be used in a room (such as an operating room) and one or more lights in the room may be turned off to produce the dimly lit or completely dark environment required for fluorescence imaging. In this embodiment, the imaging device may also be used with the tent or drape.

In some exemplary embodiments, the device may also be configured to prompt a user to confirm that the lighting conditions in the environment are sufficient (i.e., dimmed/darkened) when enabling the FL functionality of the imaging device. In other exemplary embodiments, the device may also display an indicator, such as, for example a moon icon on the image, to denote that the image was taken in an appropriate environment (i.e., in a dimmed and/or darkened environment).

Figure 42:
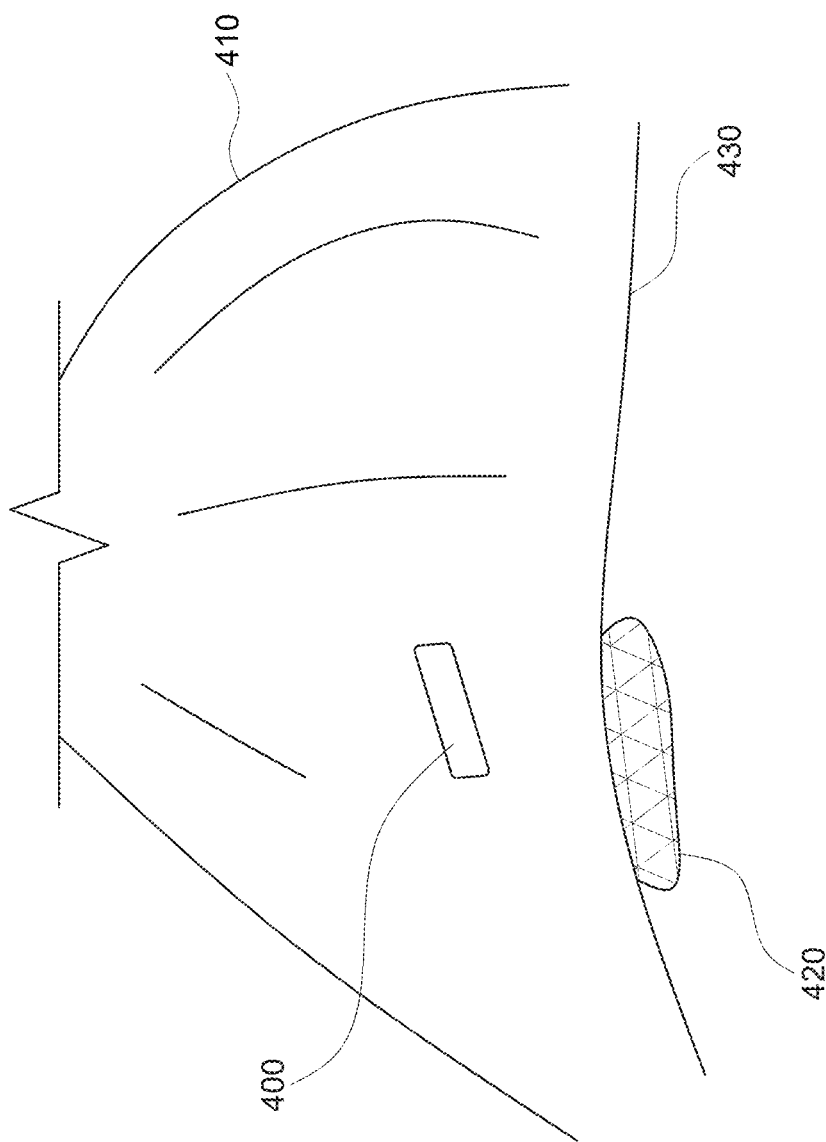
FIG. 42 shows an example of the use of a device for fluorescence-based monitoring in accordance with the present disclosure with an exemplary drape.

FIG. 42 shows an exemplary embodiment in which an imaging device 400 is used with a drape 410 for imaging a wound 420 on a patient 430 in accordance with the present disclosure. However, it is also contemplated that the device 400 and drape 410 may be used for other purposes, such as to image a patient's skin for cosmetic purposes, as discussed above. As shown in FIG. 42, the device 400 is connected to the drape to image a wound in the dimly lit or completely dark environment created by the drape 410. Thus, the drape or tent creates a darkened environment within which the target may be imaged. Those of ordinary skill in the art will understand, however, that the drape illustrated in FIG. 42 is exemplary only and that various types and/or configurations of drapes and/or tents may be used in conjunction with the disclosed imaging devices to produce the required dimly lit and/or darkened environment, without departing from the present disclosure and claims.

Kits for Device

Imaging devices in accordance with the present disclosure also may be provided in a kit, for example including the device and a fluorescing contrast agent. The contrast agent may be any one or more of those described above. For example, the contrast agent may be for labeling a biomarker in a wound, where the kit is for wound monitoring applications. Alternatively, the imaging device and a drape may be packaged or otherwise provided together.

Figure 38:
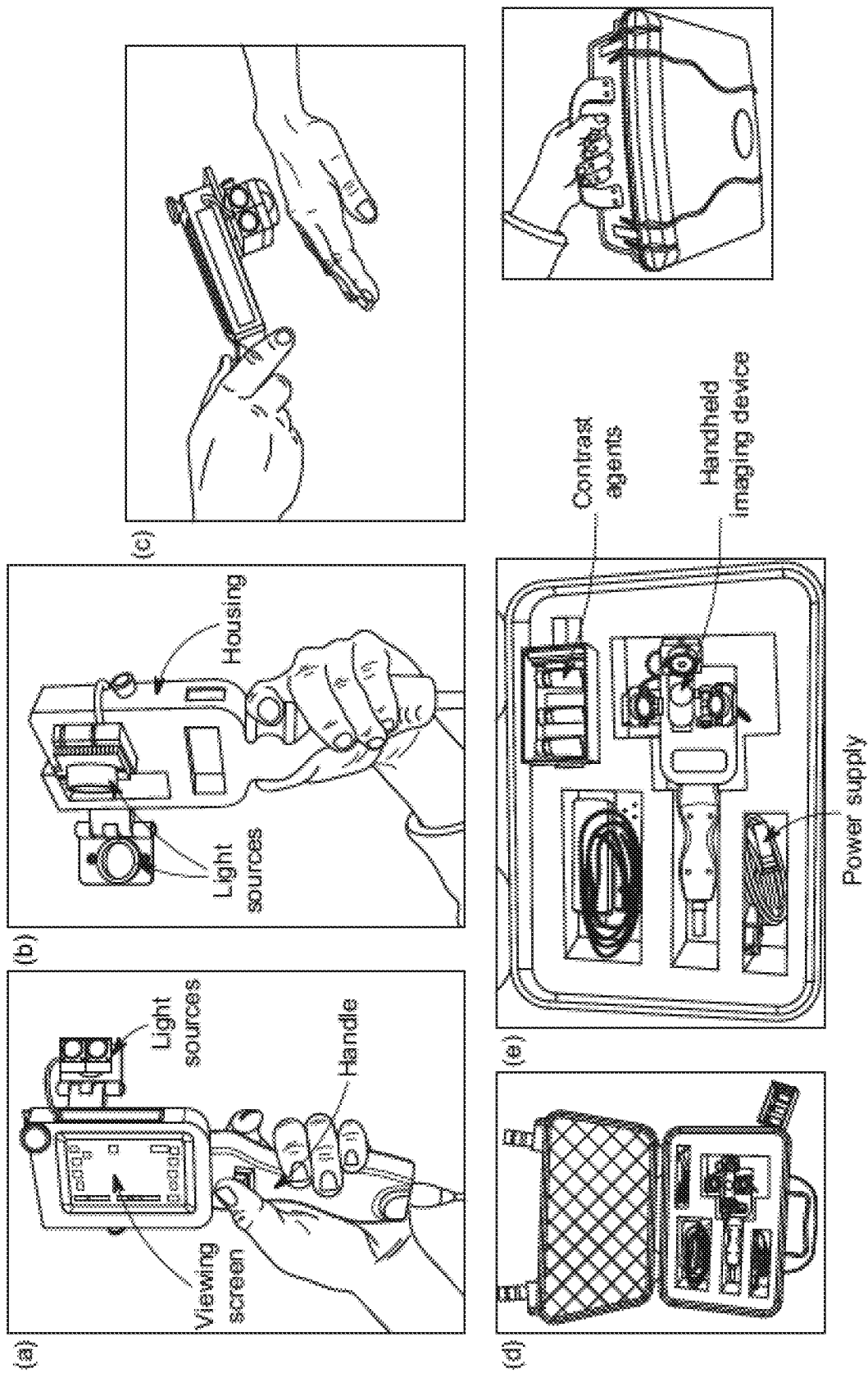
FIG. 38 shows an example of an exemplary kit including a device for fluorescence-based monitoring in accordance with the present disclosure.

FIG. 38 shows an example of a kit including an exemplary imaging device. Inset a) of FIG. 38 shows the handle and the touch-sensitive viewing screen, and inset b) of FIG. 38 shows an external housing and excitation light sources. The imaging device may be used to scan the body surface of both human and veterinary patients for image-based wound assessment, or for non-wound imaging applications. The device and any accessories (e.g., electrical/battery power supplies), potential exogenous fluorescence contrast agents, etc.) may be conveniently placed into hard-case containers for transport within clinical and non-clinical environments (including remote sites, home care and research laboratory settings).

The imaging device may be used in white light and fluorescence modes to improve the administration of these treatments as well as monitor their effectiveness over time non-invasively and quantitatively. The device may be used in combination with other imaging modalities, for example thermal imaging methods, among others.

While the present disclosure has been disclosed in terms of exemplary embodiments in order to facilitate better understanding of the disclosure, it should be appreciated that the disclosure can be embodied in various ways without departing from the principle of the disclosure. Therefore, the disclosure should be understood to include all possible embodiments which can be embodied without departing from the principle of the disclosure set out in the appended claims. Furthermore, although the present disclosure has been discussed with relation to wound imaging, monitoring, and analysis those of ordinary skill in the art would understand that the present teachings as disclosed would work equally well in various other applications such as, for example, clinically- and research-based imaging of small and large (e.g., veterinary) animals; detection and monitoring of contamination (e.g., bacterial contamination) in food/animal product preparation in the meat, poultry, dairy, fish, agricultural industries; detection of 'surface contamination' (e.g., bacterial or biological contamination) in public (e.g., health care) and private settings; multi-spectral imaging and detection of cancers in human and/or veterinary patients; as a research tool for multi-spectral imaging and monitoring of cancers in experimental animal models of human diseases (e.g., wound and cancers); forensic detection, for example of latent finger prints and biological fluids on non-biological surfaces; imaging and monitoring of dental plaques, carries and cancers in the oral cavity; periodontal disease; cancers in the tongue; imaging of an ear-nose-throat target, imaging of an ocular target; imaging of a genital target; imaging of an anal target; imaging of other suitable targets on a subject; burn wounds; imaging and monitoring device in clinical microbiology laboratories; and testing anti-bacterial (e.g., antibiotic), disinfectant agents. The use of a fluorescent imaging device in such environments is disclosed in U.S. Pat. No. 9,042,967 B2 to DaCosta et al., entitled "Device and Method for Wound Imaging and Monitoring," and issued on May 26, 2015, which is incorporated by reference herein. Additionally or alternatively, the device may be used for detecting and imaging of the presence of bacteria or microbes and other pathogens on a variety of surfaces, materials, instruments (e.g., surgical instruments) in hospitals, chronic care facilities, old age homes, and other health care settings where contamination may be the leading source of infection. The device may be used in conjunction with standard detection, identification and enumeration of indicator organisms and pathogens strategies.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the written description and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "a sensor" includes two or more different sensors. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the system and method of the present disclosure without departing from the scope its teachings. Other embodiments of the disclosure will be apparent to those skilled in the art from consideration of the specification and practice of the teachings disclosed herein. It is intended that the specification and embodiment described herein be considered as exemplary only.

The invention claimed is:

1. A system for obtaining diagnostic data of a target, the system comprising:
   an imaging device comprising:
      an adaptor configured to be removably coupled to a mobile communication device, the adaptor including at least one excitation light source configured to directly illuminate a portion of the target with excitation light;
      a mobile communication device having an optical sensor configured to detect signals responsive to illumination of the target with the excitation light;
      a processor configured to receive the detected signals, to analyze data from the detected signals using pixel intensity, and to output data regarding a bacterial load of the illuminated portion of the target; and
   a drape configured to reduce ambient light surrounding the target during imaging.

2. The system of claim 1, wherein the drape is connected to the imaging device.

3. The system of claim 1, wherein the imaging device further comprises a display for displaying the data output by the processor.

4. The system of claim 1, wherein the drape is disposable and the imaging device is configured to be attached, one at a time, to multiple disposable drapes.

5. The system of claim 1, wherein the adaptor comprises a power source for powering the at least one excitation light source.

6. The system of claim 1, wherein the adaptor comprises a filter for blocking passage of excitation light to the optical sensor.

7. The system of claim 6, wherein, when the adaptor is positioned on the mobile communication device, the filter is aligned with the optical sensor.

8. The system of claim 1, wherein the at least one excitation light source is a violet light source.

9. The system of claim 1, wherein the at least one excitation light source is configured to emit excitation light having a wavelength of between about 400 nm and about 450 nm.

10. The system of claim 9, wherein the at least one excitation light source is configured to emit excitation light having a wavelength of about 405 nm±15 nm.

11. The system of claim 1, wherein the at least one excitation light source is configured to emit excitation light having a wavelength of between about 400 nm and about 450 nm, about 450 nm to about 500 nm, about 500 nm to about 550 nm, 550 nm to about 600 nm, about 600 nm to about 650 nm, about 650 nm to about 700 nm, about 700 nm to about 750 nm, and combinations thereof.

12. The system of claim 11, wherein the at least one excitation light source is configured to emit blue/violet light.

13. The system of claim 12, wherein the at least one excitation light source is configured to emit excitation light having a wavelength of between about 400 nm and about 450 nm.

14. The system of claim 12, wherein the at least one excitation light source is configured to emit excitation light having a wavelength of about 405 nm±15 nm.

15. The system of claim 1, further comprising a filter configured to block passage of excitation light to the optical sensor.

16. The system of claim 1, further comprising a filter configured to permit passage of signals responsive to illumination of the target with the excitation light to the optical sensor.

17. The system of claim 16, wherein the filter is configured to permit passage of emissions having a wavelength of about 500 nm to about 550 nm and/or about 590 nm to about 690 nm.

18. The system of claim 16, wherein the filter is configured to permit passage of emissions having a wavelength of about 450 nm to about 505 nm and/or about 590 nm to about 650 nm.

19. The system of claim 16, wherein the filter is configured to permit passage of emissions having a wavelength of about 635+/−10 nm.

20. The system of claim 1, further comprising a white light source for illuminating the target with white light during imaging.

21. The system of claim 20, further comprising a filter configured to permit passage of signals responsive to illumination of the target with white light.

22. The system of claim 21, wherein the filter is configured to permit passage of emissions responsive to white light illumination of the target and having a wavelength of about 405+/−25 nm, 546+/−25 nm, and/or 600+/−25 nm.

23. A method of obtaining diagnostic data of a target, the method comprising:
positioning a drape around the target to reduce ambient light in an environment surrounding the target;
while the target is within the reduced ambient light environment:
directly illuminating the target with excitation light emitted by at least one excitation light source of a handheld imaging device, the at least one excitation light source emitting at least one wavelength or wavelength band configured to cause at least one biomarker in the target to fluoresce, and
collecting bacterial autofluorescence data regarding the illuminated target with the handheld imaging device by detecting, with an image sensor of the handheld imaging device, signals responsive to illumination of the target with the excitation light; and
analyzing the collected bacterial autofluorescence data with a processor of the handheld imaging device and using pixel intensity to determine bacterial load of the illuminated target.

24. The method of claim 23, wherein the target includes a wound in tissue.

25. The method of claim 23, wherein reducing the ambient light comprises turning off one or more lights in the environment.

26. The method of claim 23, wherein reducing the ambient light comprises creating a dimly lit environment.

27. The method of claim 23, wherein reducing the ambient light comprises creating a completely dark environment.

28. The method of claim 23, further comprising connecting a drape to the handheld imaging device.

29. The method of claim 23, further comprising blocking, with a filter of the handheld imaging device, passage of reflected excitation light to the image sensor.

30. The method of claim 23, further comprising collecting, with the handheld imaging device, tissue autofluorescence data regarding the illuminated target.

31. The method of claim 23, further comprising illuminating the target with a white light source for white light imaging of the target and collecting signals responsive to illumination of the target with the white light.

32. The method of claim 31, wherein white light imaging of the target is performed when the target is not in the reduced ambient light environment.

33. The method of claim 31, wherein white light imaging of the target is performed when the target is in the reduced ambient light environment.

34. A system for determining a bacterial load of a target, comprising:
an adaptor for configuring a mobile communication device for fluorescent imaging of a target, the adaptor comprising:
a housing configured to be removably coupled to a mobile communication device;
at least one excitation light source configured to emit excitation light selected to elicit emission of bacterial autofluorescence from bacteria in a target directly illuminated with the excitation light;
an emissions filter configured to permit signals responsive to illumination of the target with the excitation light and corresponding to bacterial autofluorescence of the target to pass through the emissions filter; and
a power source for the at least one excitation light source; and
a mobile communication device comprising:
an optical sensor, and
a processor configured to:
receive the signals responsive to illumination of the target with the excitation light and corresponding to bacterial autofluorescence of the target, analyze the signals using pixel intensity, and
output data regarding a bacterial load of the target.

35. The adaptor of claim 34, wherein the emissions filter is positioned to be aligned with an optical sensor of the mobile communication device when the adaptor is connected to the mobile communication device.

36. The adaptor of claim 34, further comprising a filter configured to block passage of excitation light to an optical sensor of the mobile communication device.

37. The adaptor of claim 36, wherein, when the adaptor is positioned on the mobile communication device, the filter configured to block excitation light is aligned with the optical sensor of the mobile communication device.

38. The adaptor of claim 34, wherein the at least one excitation light source is configured to emit excitation light having a wavelength of between about 400 nm and about 450 nm, about 450 nm to about 500 nm, about 500 nm to about 550 nm, 550 nm to about 600 nm, about 600 nm to about 650 nm, about 650 nm to about 700 nm, about 700 nm to about 750 nm, and combinations thereof.

39. The adaptor of claim 38, wherein the at least one excitation light source is configured to emit blue/violet light.

40. The adaptor of claim 39, wherein the at least one excitation light source is configured to emit excitation light having a wavelength of between about 400 nm and about 450 nm.

41. The adaptor of claim 40, wherein the at least one excitation light source is configured to emit excitation light having a wavelength of about 405 nm±15 nm.

42. The adaptor of claim 34, further comprising a dichroic mirror configured to be disposed in front of an optical sensor of the mobile communication device.

43. The adaptor of claim 34, further comprising a macro lens.

44. The adaptor of claim 34, further comprising a toggle switch configured switch the adaptor between a fluorescent imaging mode and a white light imaging mode.

45. The adaptor of claim 34, wherein the housing includes an opening configured to receive a portion of a mobile communication device.

46. The adaptor of claim 45, wherein the opening is configured to receive the mobile communication device in a manner that aligns an optical sensor of the mobile communication device with the emission filter.

47. The adaptor of claim 34, further comprising a heat sink.

48. The adaptor of claim 34, wherein the emissions filter is configured to permit passage of emissions having a wavelength of about 500 nm to about 550 nm and/or a wavelength of about 590 nm to about 690 nm.

49. The adaptor of claim 34, wherein the emissions filter is configured to permit passage of emissions having a wavelength of about 450 nm to about 505 nm and/or a wavelength of about 590 nm to about 650 nm.

50. The adaptor of claim 34, wherein the emissions filter is configured to permit passage of emissions having a wavelength of about 635+/−10 nm.

51. The adaptor of claim 34, wherein the emissions filter is configured to move between a first position and a second position.

52. The adaptor of claim 51, wherein, when the adaptor is removably coupled to the mobile communication device, the first position aligns the emissions filter with an optical sensor of the mobile communication device and the second position moves the emissions filter out of alignment with the optical sensor of the mobile communication device.

53. The adaptor of claim 34, wherein the at least one excitation light source configured to emit excitation light selected to elicit emission of bacterial autofluorescence from bacteria in a target is a first excitation light source configured to emit a first excitation light at a first wavelength or wavelength band and further comprising a second excitation light source configured to emit a second excitation light at a second wavelength or wavelength band, wherein the first wavelength or wavelength band is different than the second wavelength or wavelength band.

54. The adaptor of claim 53, wherein the first wavelength or wavelength band is between about 400 nm and 450 nm and the second wavelength or wavelength band is between about 450 nm to about 500 nm, about 500 nm to about 550 nm, 550 nm to about 600 nm, about 600 nm to about 650 nm, about 650 nm to about 700 nm, about 700 nm to about 750 nm, and combinations thereof.

55. The adaptor of claim 53, wherein the first excitation light source is configured to emit excitation light having a wavelength of about 405 nm±20 nm.

56. The adaptor of claim 53, further comprising at least one thermal sensor for detecting thermal information from the target.

57. The adaptor of claim 34, further comprising at least one thermal sensor for detecting thermal information from the target.

58. The system of claim 34, wherein the adaptor further comprises at least one thermal sensor for detecting thermal data regarding the target.

59. The system of claim 58, wherein the processor is further configured to receive the thermal data, correlate the thermal data with data based on the signals responsive to illumination of the target with the excitation light and corresponding to bacterial autofluorescence of the target, and provide an output based on the correlation of the data.

60. The system of claim 59, wherein the target is a wound in tissue and the output based on the correlation of the data includes one or more of an indication of wound status, an indication of wound healing, an indication of wound infection, bacterial load of the wound, temperature of the wound, and distribution of bacteria within the wound.

* * * * *